(12) United States Patent
Inaba et al.

(10) Patent No.: US 6,806,276 B2
(45) Date of Patent: *Oct. 19, 2004

(54) 2-OXOQUINOLINE COMPOUNDS AND PHARMACEUTICAL USES THEREOF

(75) Inventors: Takashi Inaba, Takatsuki (JP); Tetsudo Kaya, Takatsuki (JP); Hiroyuki Iwamura, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 56 days.

This patent is subject to a terminal disclaimer.

(21) Appl. No.: 10/245,861

(22) Filed: Sep. 16, 2002

(65) Prior Publication Data

US 2003/0191069 A1 Oct. 9, 2003

Related U.S. Application Data

(63) Continuation of application No. 09/869,895, filed as application No. PCT/JP99/07398 on Dec. 28, 1999, now Pat. No. 6,509,352.

(30) Foreign Application Priority Data

Jan. 8, 1999 (JP) ............................................ 11-003498

(51) Int. Cl.⁷ ...................... A61K 31/47; C07D 215/16; C07D 215/20
(52) U.S. Cl. ...................... 514/312; 546/154; 546/155; 546/157
(58) Field of Search ................................ 546/154, 155, 546/157; 514/312

(56) References Cited

U.S. PATENT DOCUMENTS

| 4,542,139 A | 9/1985 | Hitzel et al. |
| 4,710,507 A | 12/1987 | Campbell et al. |
| 6,329,525 B1 | 12/2001 | Nakazato |

FOREIGN PATENT DOCUMENTS

| EP | 059 698 B1 | 9/1985 |
| EP | 887 340 A1 | 12/1998 |
| FR | 2377400 | 8/1978 |
| JP | 47-14107 | 4/1972 |
| WO | WO 90/15052 | 12/1990 |
| WO | WO 92/18483 | 10/1992 |
| WO | WO 96/05166 | 2/1996 |
| WO | WO 99/02499 | 1/1999 |

OTHER PUBLICATIONS

"Pharmaprojects" (1981) PJB Publications, Ltd., Richmond, Surrey, UK, 2 pages.
El–Kerdawy et al. (1984) *J. Pharm. Sci.* 73(11):1652–1653.
Fernandez et al. (1995) *Synthesis* 11:1362–1364.
Inaba et al. (Jan. 1999) *Chem. Abstracts* 130:110167, Abstract of WO 99/02499.
Nakazato et al. (Jun. 1999) *Chem. Abstracts* 131:31882, Abstract of WO 99/28299.
Suzuki et al. (Feb. 1996) *Chem. Abstracts* 125:58298, Abstract of WO 96/05166.
Ukraintest IV et al. (1993) *Khim. Geterosikl Soedin* 8:1101–1104 with English Abstract.

*Primary Examiner*—D. Margaret Seaman
(74) *Attorney, Agent, or Firm*—Finnegan, Henderson, Farabow, Garrett & Dunner, LLP

(57) ABSTRACT

A 2-oxoquinoline compound or its pharmaceutically acceptable salt of general formula [I]:

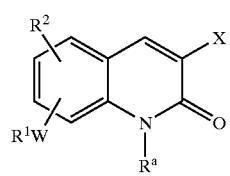

(wherein each symbol in the formula is as determined in the description), and its pharmaceutical use. The compound [I] of the present invention and its pharmaceutically acceptable salts selectively act on cannabinoid receptors, particularly on peripheral type cannabinoid receptors, and have fewer side effects on the central nervous system, having great immunosuppressive action, anti-inflammatory action or antiallergic action. Therefore, these compounds are useful as cannabinoid receptors (particularly peripheral type cannabinoid receptors) modulator, immunosuppressants, anti-inflammatory agents, and antiallergic agents.

7 Claims, No Drawings

2-OXOQUINOLINE COMPOUNDS AND PHARMACEUTICAL USES THEREOF

CROSS-REFERENCE TO RELATED APPLICATIONS

This application is a continuation of U.S. patent application 09/869,895 now U.S. Pat. No. 6,509,352 that was filed on Jul. 5, 2001 and fulfilled the requirements of 35 USC §371(c)(4) on Aug. 29, 2001, which application is a 35 USC §371 national phase application of PCT application serial number PCT/JP99/07398, filed Dec. 28, 1999, which application claims priority to Japanese patent application number JP11/003498, filed Jan. 8, 1999, each of which applications is herein incorporated by reference in their entirety.

TECHNICAL FIELD

The present invention relates to novel 2-oxoquinoline compounds and pharmaceutical uses thereof. In addition, the invention relates to novel uses of some types of 2-oxoquinoline compounds. More specifically, the invention relates to novel 2-oxoquinoline compounds that selectively act on cannabinoid receptors, particularly on peripheral cannabinoid receptors, and that have immunomodulating action, anti-inflammatory action, and antiallergic action with fewer side effects on the central nervous system and to pharmaceutical uses thereof.

BACKGROUND ART

So far, a series of compounds named cannabinoids, which comprise C, H, and O, are known as constituents of cannabis. It has also been known that, among them, tetrahydrocannabinol (THC) is a major hallucinogen, and that a principal ingredient contained in the cannabis plant is Δ9-THC. It has been reported that Δ9-THC has actions including ataxia, increased sensitivity to stimulation, antiemetic action, analgesic action, hypothermic action, respiratory depression, catalepsy-inducing action, vasodilator action, immunosuppressive action, etc.

The sites of these actions of Δ9-THC are roughly categorized into the central nervous system (Devane et al., Mol Pharmacol. 1988, 34, 605–613; Hollister et al., Pharmacol. Rev., 1986, 38, 1–20; Renu et al., Prog. Drug Res., 1991, 36, 71–114) and the peripheral tissues (Nye et al., J. Pharmacol. Exp. Ther., 1985, 234, 784–791; Flynn et al., Mol Pharmacol. 1992, 41, 736–742). There are reports suggesting that some of the actions on the central nervous system are medically applicable.

On the other hand, it has been found that there exists the peripheral type receptor, for example, the receptor on macrophages (Munnro et al., Nature, 1993, 365, 61–65). Based on this finding, research and development are being carried out with the objective of designing peripheral type receptor agonists capable of modulating immune reaction and having anti-inflammatory action, antiallergic action, as well as the original immunomodulating action.

Further, agents selectively acting on peripheral type cannabinoid receptors can be safe agents that have no side effects on the central nervous system such as hypothermic action, catalepsy, and such, and therefore modulators selective for the peripheral type receptor are expected to be developed in particular.

Known cannabinoid receptor agonists include pyrazole derivatives (Unexamined Published Japanese Patent Application (JP-A) No. Hei 6-73014; EP Nos. 656354 and 658546), THC derivatives (JP-A Hei 3-209377), benzox- azine derivatives (U.S. Pat. No. 5,112,820), indole derivatives (U.S. Pat. No. 5,081,122), and aliphatic acid derivatives (WO 94/12466). However, there have previously been no findings on 2-oxoquinoline compounds by which the compounds of the present invention are characterized.

On the other hand, a variety of quinoline derivatives have been reported in terms of chemical structure.

For example, a reference of J. Pharm. Sci., 73, 11, 1652–1653 (1984) describes 6,7-dimethoxy-2-oxo-1,2-dihydroquinoline-3-carboxylic acid benzylamide (compound A shown below), which is useful as a stimulant for the central nervous system. Another reference, Khim. Geterotsikl. Soedin., 8, 1101–1104 (1993), describes 4-hydroxy-2-oxo-1,2-dihydroquinoline-3-carboxylic acid (pyridine-2-yl)amide (compound B shown below), which is useful as an anti-inflammatory agent. In Pharmaproject and others, it has been reported that 4-hydroxy-2-oxo-1-methyl-1,2-dihydroquinoline-3-carboxylic acid N-methyl-N-phenylamide (compound C shown below) that is also called "roquinimex" can be used as agents for a variety of diseases, e.g., anti-inflammatory agent, immunosuppressant, and anti-rheumatic agent.

Further, Examined Japanese Patent Publication No. Sho 47-14107 discloses a method for synthesizing 3-benzoylamino-6,7-dimethoxy-2-(1H)quinolone (compound D shown below) that can be used as an agent acting on the central nervous system.

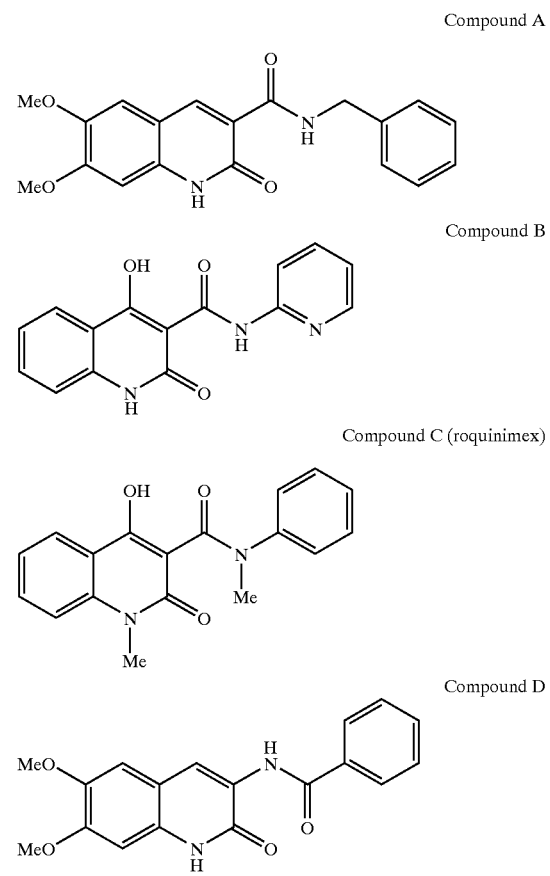

In addition, 2-oxo-1,2-dihydroquinoline-3-carboxylic acid cyclohexylamide has been disclosed in synthesis, 11, 1362–1364 (1995). Quinoline compounds which are useful as immunomodulators have been disclosed in Published Japanese Translation of International Publication No. Hei 4-500373. Quinoline compounds which are useful as analgesic agents have been disclosed in French Patent Publication No. 2377400. Quinoline compounds which are useful as 5-HT$_4$ receptor agonists have been disclosed in republished patent publication WO 96/05166.

Further, one of 2-oxoquinoline compounds having 3,4-methylenedioxyphenyl group, which is one of specific features of the compounds of the present invention, is N-(3,4-methylenedioxyphenyl)-1,2-dihydro-4-hydroxy-1-methyl-2-oxoquinoline-3-carboxamide (compound E shown below), which is a compound capable of enhancing immunological activities and has been disclosed in JP-A Sho 57-171975 (EP No. 59698). Yet further, 1-methyl-2-oxo-3-(N-(1,3-benzodioxole-5-yl)-N-methylcarbamoyl)-4-hydroxy-6-methylthio-1,2-dihydroquinoline (compound F shown below), which has immunomodulating action, anti-inflammatory action, and analgesic action, has been disclosed in Published Japanese Translation of International Publication No. Hei 6-506925 (WO 92/18483).

However, these references have no description suggesting the existence of 2-oxoquinoline compounds of the present invention nor suggestion of pharmacological action based on the cannabinoid receptor-mediated mechanism.

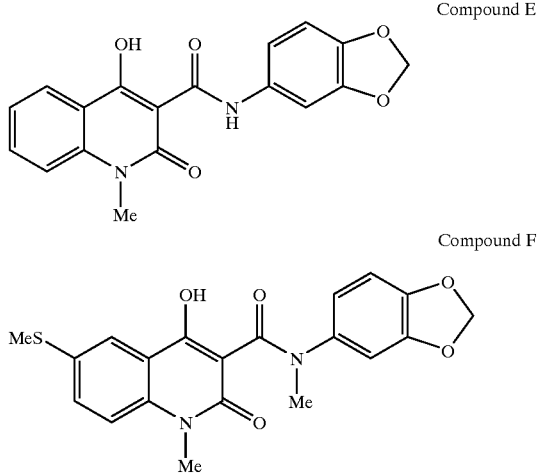

Compound E

Compound F

On the other hand, description found in the publication of WO 97/29079 is that some compounds having quinoline structure, functioning as cannabinoid receptor agonist or antagonist, are useful as immunomodulators, anti-inflammatory agents, antiallergic agents, or the like.

However, the quinoline compounds disclosed in the reference are merely quinolines that have been substituted with a hydroxy, and in the reference, there is no description suggesting the existence of the 2-oxoquinoline compounds of the present invention.

A reference of JP-A Hei 11-80124 (WO 99/02499) also describes immunomodulator, anti-inflammatory agent, and antiallergic agent comprising cannabinoid receptor agonist or antagonist as an active ingredient. The patent publication has also disclosed 7-methoxy-2-oxo-8-pentyloxy-1,2-dihydroquinoline-3-carboxylic acid (4-aminophenyl)amide (compound G) and such, which is one of compounds having the 2-oxoquinoline structure that is one of specific features of the compounds of the present invention.

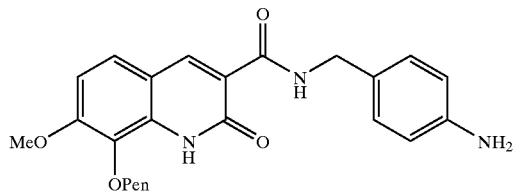

Compound G

In more detail, in the above-mentioned patent publication, for example, just merely the above-mentioned compound G and three other compounds are specifically disclosed, and the reference has no description of the inventive compounds that disclosed herein, which is represented by general formula [I], including compounds of which R$^a$ is alkyl; compounds of which X is —COOR$^b$, —CONH$_2$, —(CH$_2$)$_p$—OC(=Y)—NR$^d$-(Alk$^b$)$_g$—R, —(CH$_2$)$_q$—NR$^e$—C(=Z)—(NR$^f$)$_w$-(Alk$^c$)$_v$-R, —(CH$_2$)$_p$—OH, or —(CH$_2$)$_q$—NR$^e$R$^{e'}$ (where each symbol is as defined herein); compounds of which X is —CONR$^c$-(Alk$^a$)$_r$-R and R$^c$ is alkyl; or compounds of which R is represented by:

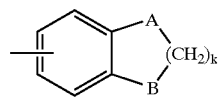

where each symbol is as defined herein.

It should be noted that, while the above-mentioned patent application was first laid open to public inspection on Jan. 21, 1999 (WO 99/02499), the priority date of the present application is Jan. 8, 1999, which is therefore earlier than the above publication date.

DISCLOSURE OF THE INVENTION

An objective of the present invention is to provide novel compounds selectively acting on cannabinoid receptors, particularly on peripheral cannabinoid receptors and to provide pharmaceutical compositions thereof.

More specifically, the objective of the present invention is to provide novel compounds and pharmaceutical compositions thereof that are capable of selectively acting on cannabinoid receptors, particularly on the receptors of peripheral tissues, and that have therapeutic effects including immunomodulating action, anti-inflammatory action, anti-allergic action, and such, but that hardly influence the central nervous system (specifically, side effects such as excitation, hallucination, ataxia, increased sensitivity to stimulation, hypothermicaction, respiratory depression, catalepsy-inducing action, hypotention, etc.) and that are less toxic.

In order to achieve the above-mentioned objective, the present inventors strenuously studied and then found 2-oxoquinoline compounds exhibiting selective affinity for cannabinoid receptors, particularly for the peripheral type receptors, and thus being pharmaceutically useful for diseases associated with cannabinoid receptors, particularly diseases associated with peripheral type tissues (immune disease, various types of inflammation, allergic diseases, etc.). Thus, the inventors completed the present invention.

Specifically, the present invention comprises the following items (1)–(27):

(1) A cannabinoid receptor modulator comprising, as an active ingredient, a 2-oxoquinoline compound represented by the following general formula [I] or its pharmaceutically acceptable salt:

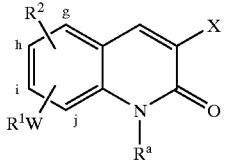

[I]

where W means —O—, —S(O)$_t$—, —CR$^3$R$^4$—, —NR$^5$—, —NR$^5$CO—, —CONR$^5$—, —COO—, or —OCO— (where R$^3$ and R$^4$ may be identical or different and represent hydrogen atom or alkyl; R$^5$ represents hydrogen atom or alkyl; and t indicates an integer, 0, 1 or 2);

R$^1$ represents hydrogen atom, alkyl, alkenyl, alkynyl, aryl, arylalkyl, heteroaryl, heteroarylalkyl, cycloalkyl, or cycloalkylalkyl; each group of R$^1$, except hydrogen atom, may be substituted or unsubstituted with alkylamino, amino, hydroxy, alkoxy, carboxy, alkoxycarbonyl, acyl, acyloxy, acylthio, mercapto, alkylthio, alkylsulfinyl or alkylsulfonyl; each group, except hydrogen atom and alkyl, may be substituted or unsubstituted with alkyl;

R$^2$ represents hydrogen atom, alkyl, —OR$^6$ (where R$^6$ represents hydrogen atom, alkyl, alkenyl, alkynyl, aryl, arylalkyl, heteroaryl, heteroarylalkyl, cycloalkyl or cycloalkylalkyl), —NR$^7$R$^8$ (where R$^7$ and R$^8$ may be identical or different and represent hydrogen atom, alkyl, alkenyl, alkynyl, acyl, aryl, arylalkyl, heteroaryl, heteroarylalkyl, cycloalkyl or cycloalkylalkyl; or R$^7$ and R$^8$, together with the adjacent nitrogen atom, can form a heteroaryl); or —(CH$_2$)$_u$'—S(O)$_u$R$^9$ (where R$^9$ represents hydrogen atom, alkyl, alkenyl or alkynyl, each of u and u' independently represents an integer, 0, 1 or 2); each group of R$^2$, except hydrogen atom, may be substituted or unsubstituted with alkylamino, amino, hydroxy, alkoxy, alkoxycarbonyl, acyl, acyloxy, acylthio, mercapto, alkylthio, alkylsulfinyl or alkyl sulfonyl; each group, except hydrogen atom and alkyl, may be substituted or unsubstituted with alkyl;

R$^a$ represents hydrogen atom or alkyl;

X represents —COOR$^b$, —CONH$_2$, —CONR$^c$-(Alk$^a$)$_r$-R, —(CH$_2$)$_p$—OC(=Y)—NR$^d$—(Alk$^b$)$_a$-R, —(CH$_2$)$_q$—NR$^e$—C(=Z)——(NR$^f$)$_w$-(Alk$^c$)$_v$-R, —(CH$_2$)$_p$—OH or —(CH$_2$)$_q$—NR$^e$R$^{e'}$ (where each of R$^b$, R$^c$, R$^d$, and R$^f$ independently represents hydrogen atom or alkyl; each of R$^e$ and R$^{e'}$ independently represents hydrogen atom or alkyl; or R$^e$ and R$^{e'}$, together with the adjacent nitrogen atom, can form a heteroaryl; each of Alk$^a$, Alk$^b$ and Alk$^c$ independently represents alkylene or alkenylene; each of the alkylene and alkenylene may be substituted or unsubstituted with hydroxy, carboxy, alkoxycarbonyl, alkyl (the alkyl may be substituted or unsubstituted with hydroxy, alkoxy or alkylthio) or —CONR$^{10}$R$^{11}$ (where R$^{10}$ and R$^{11}$ may be identical or different and represent hydrogen atom or alkyl; or R$^{10}$ and R$^{11}$, together with the adjacent nitrogen atom, can form a heteroaryl);

R represents aryl, heteroaryl, cycloalkyl, benzene-condensed cycloalkyl or

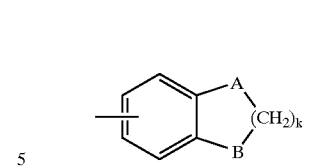

where A and B independently represent oxygen atom, nitrogen atom or sulfur atom; k indicates an integer of 1–3; each of the aryl and heteroaryl may be substituted or unsubstituted with an alkyl substituted or unsubstituted with hydroxy or may be substituted or unsubstituted with a hydroxy, alkoxy, alkenyloxy, acyl, acyloxy, halogen atom, nitro, amino, sulfonamide, alkylamino, aralkyloxy, pyridyl, piperidino, carboxy, alkoxycarbonyl, acylamino, aminocarbonyl, cyano or glucuronic acid residue; the cycloalkyl may be substituted or unsubstituted with a hydroxy, alkoxy or =O; the benzene-condensed cycloalkyl may be substituted or unsubstituted with a hydroxy or alkoxy; each of r, s, v and w independently represents 0 or 1; each of Y and Z independently represents a nitrogen atom, oxygen atom or sulfur atom; and each of p and q independently represents an integer of 1–4).

(2) A cannabinoid receptor modulator comprising, as an active ingredient, the 2-oxoquinoline compound of (1) or its pharmaceutically acceptable salt, wherein W represents —O—; R$^1$ is hydrogen atom or alkyl (the alkyl is as described above); R$^2$ represents —OR$^6$ (R$^6$ is as described above); and R is aryl, heteroaryl or

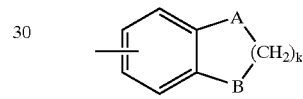

where aryl, heteroaryl, and each symbol in the formula are as defined above.

(3) A 2-oxoquinoline compound as represented by the following general formula [I'] or its pharmaceutically acceptable salt:

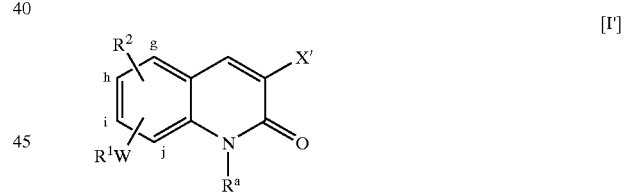

[I']

where W means —O—, —S(O)$_t$—, —CR$^3$R$^4$—, —NR$^5$—, —NR$^5$CO—, —CONR$^5$—, —COO— or —OCO— (where R$^3$ and R$^4$ may be identical or different and represent hydrogen atom or alkyl; R$^5$ represents hydrogen atom or alkyl; and t indicates an integer, 0, 1 or 2); R$^1$ represents hydrogen atom, alkyl, alkenyl, alkynyl, aryl, arylalkyl, heteroaryl, heteroarylalkyl, cycloalkyl or cycloalkylalkyl; each group of R$^1$, except hydrogen atom, may be substituted or unsubstituted with alkylamino, amino, hydroxy, alkoxy, carboxy, alkoxycarbonyl, acyl, acyloxy, acylthio, mercapto, alkylthio, alkylsulfinyl or alkylsulfonyl; each group, except hydrogen atom and alkyl, may be substituted or unsubstituted with alkyl; R$^2$ represents hydrogen atom, alkyl, —OR$^6$ (where R$^6$ represents hydrogen atom, alkyl, alkenyl, alkynyl, aryl, arylalkyl, heteroaryl, heteroarylalkyl, cycloalkyl or cycloalkylalkyl), —NR$^7$R$^8$ (where R$^7$ and R$^8$ may be identical or different and represent hydrogen atom, alkyl, alkenyl, alkynyl, acyl, aryl, arylalkyl, heteroaryl, heteroarylalkyl, cycloalkyl or cycloalkylalkyl; or R$^7$ and R$^8$, together with the adjacent nitrogen atom, can form a heteroaryl); or —(CH$_2$)$_u$'—S(O)$_u$R$^9$ (where R$^9$ represents hydrogen atom, alkyl, alkenyl or alkynyl, each of u and u' independently represents an integer, 0, 1 or 2) ; each group of R$^2$, except hydrogen atom, may be substituted or unsubstituted with alkylamino, amino, hydroxy, alkoxy, alkoxycarbonyl, acyl, acyloxy, acylthio, mercapto, alkylthio, alkylsulfinyl or alkyl sulfonyl; each group, except hydrogen atom and alkyl, may be substituted or unsubstituted with alkyl; R$^a$ represents hydrogen atom or alkyl; X' represents —CONR$^c$-(Alk$^a$)$_r$-R, —(CH$_2$)$_p$—OC(=Y)—NR$^d$-(Alk$^b$)$_s$-R or —(CH$_2$)$_q$—NR$^e$—C(=Z)—(NR$^f$)$_w$-(Alk$^c$)$_v$-R, where each of R$^c$, R$^d$, R$^e$ and R$^f$ independently represents hydrogen atom or alkyl; each of Alk$^a$, Alk$^b$ and Alk$^c$ independently represents alkylene or alkenylene; each of the alkylene and alkenylene may be substituted or unsubstituted with hydroxy, carboxy, alkoxycarbonyl, alkyl (the alkyl may be substituted or unsubstituted with a hydroxy, alkoxy or alkylthio); or —CONR$^{10}$R$^{11}$ (where R$^{10}$ and R$^{11}$ may be identical or different and represent hydrogen atom or alkyl; or R$^{10}$ and R$^{11}$, together with the adjacent nitrogen atom, can form a heteroaryl); R represents aryl, heteroaryl, cycloalkyl, benzene-condensed cycloalkyl or

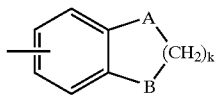

where A and B independently represent oxygen atom, nitrogen atom or sulfur atom; k indicates an integer of 1–3; each of the aryl and heteroaryl may be substituted or unsubstituted with an alkyl substituted or unsubstituted with hydroxy or may be substituted or unsubstituted with a hydroxy, alkoxy, alkenyloxy, acyl, acyloxy, halogen atom, nitro, amino, sulfonamide, alkylamino, aralkyloxy, pyridyl, piperidino, carboxy, alkoxycarbonyl, acylamino, aminocarbonyl, cyano or glucuronic acid residue; the cycloalkyl may be substituted or unsubstituted with a hydroxy, alkoxy or =O; the benzene-condensed cycloalkyl may be substituted or unsubstituted with a hydroxy or alkoxy; each of r, s, v and w independently represents 0 or 1; each of y and Z independently represents a nitrogen atom, oxygen atom or sulfur atom; and each of p and q independently represents an integer of 1–4, provided that:

(a) when R$^2$ is a hydrogen atom, then WR$^1$ is substituted at position-j of 2-oxoquinoline; and (b) 1,2-dihydro-6,7-dimethoxy-2-oxo-N-(phenylmethyl)-3-quinolinecarboxamide and N-(1,2-dihydro-6,7-dimethoxy-2-oxo-3-quinolyl)benzamide are excluded.

(4) The 2-oxoquinoline compound of (3) or its pharmaceutically acceptable salt, wherein R$^a$ is alkyl.

(5) The 2-oxoquinoline compound of (3) or its pharmaceutically acceptable salt, wherein X' is —CONR$^c$-(Alk$^a$)$_r$-R.

(6) The 2-oxoquinoline compound of (5) or its pharmaceutically acceptable salt, wherein R$^c$ is alkyl.

(7) The 2-oxoquinoline compound of (3) or its pharmaceutically acceptable salt, wherein X' is —(CH$_2$)$_p$—OC(=Y)—NR$^d$-(Alk$^b$)$_s$-R or —(CH$_2$)$_q$—NR$^e$—C(=Z)—(NR$^f$)$_w$-(Alk$^c$)$_v$-R.

(8) The 2-oxoquinoline compound of (3) or its pharmaceutically acceptable salt, wherein W is —O—; R$^1$ is hydrogen atom or alkyl having 1–3 carbons (the alkyl may be substituted or unsubstituted with alkylamino, amino, hydroxy, alkoxy, carboxy, alkoxycarbonyl, acyl, acyloxy, acylthio, mercapto, alkylthio, alkylsulfinyl or alkylsulfonyl); and R$^2$ is —OR$^6$ (where R$^6$ represents hydrogen atom or alkyl having 1–3 carbons (the alkyl may be substituted or unsubstituted with alkylamino, amino, hydroxy, alkoxy, alkoxycarbonyl, acyl, acyloxy, acylthio, mercapto, alkylthio, alkylsulfinyl or alkyl sulfonyl)).

(9) The 2-oxoquinoline compound of any one of (3)–(8) or its pharmaceutically acceptable salt, wherein R is aryl, heteroaryl or

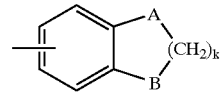

where aryl, heteroaryl, and each symbol in the formula are as defined above.

(10) The 2-oxoquinoline compound of any one of (3)–(8) or its pharmaceutically acceptable salt, wherein R is

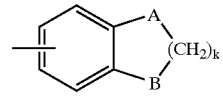

where each symbol is as defined above.

(11) The 2-oxoquinoline compound of any one of (3)–(10) or its pharmaceutically acceptable salt, wherein W is —O— and R$^2$ is —OR$^6$ (where R$^6$ is a hydrogen atom or alkyl).

(12) The 2-oxoquinoline compound of any one of (3)–(11) or its pharmaceutically acceptable salt, wherein the substitution position of WR$^1$ is position-j of the benzene ring, and the substitution position of R$^2$ is position-i of the benzene ring.

(13) The 2-oxoquinoline compound of any one of (3)–(6) and (8)–(12) or its pharmaceutically acceptable salt, wherein Alk$^a$ is alkylene and r=1.

(14) The 2-oxoquinoline compound of (3) or its pharmaceutically acceptable salt, wherein the 2-oxoquinoline compound excludes 7-methoxy-2-oxo-8-pentyloxy-1,2-dihydroquinoline-3carboxylic acid (2-pyridine-4-ylethyl) amide; 7-methoxy-2-oxo-8-pentyloxy-1,2-dihydroquinoline-3-carboxylic acid (4-aminobenzyl)amide; 7-methoxy-2-oxo-8-pentyloxy-1,2-dihydroquinoline-3-carboxylic acid [2-(4-aminophenyl)ethyl]amide; and 7-methoxy-2-oxo-8-pentyloxy-1,2-dihydroquinoline-3-carboxylic acid (4-aminophenyl)amide.

(15) The 2-oxoquinoline compound of (3) or its pharmaceutically acceptable salt, wherein the 2-oxoquinoline compound excludes compounds in which W is —O—; R$^1$ is alkyl; R$^2$ is —OR$^6$ (where R$^6$ is alkyl); R$^a$ is hydrogen; and X' is —CONR$^c$-(Alk$^a$)$_r$-R (where R$^c$ is a hydrogen atom; Alk$^a$ is methylene, ethylene or trimethylene; r is 0 or 1; and R is aryl or heteroaryl).

(16) The 2-oxoquinoline compound of (5) or its pharmaceutically acceptable salt, wherein R is aryl (the aryl may be substituted or unsustituted with hydroxy, alkoxy, alkenyloxy, acyloxy, halogen atom, aralkyloxy, or glucuronic acid residue).

(17) The 2-oxoquinoline compound of (3) or its pharmaceutically acceptable salt, wherein R is aryl except phenyl or is heteroaryl except pyridyl.

(18) The 2-oxoquinoline compound of any one of (3)–(17) or its pharmaceutically acceptable salt, wherein the 2-oxoquinoline compound is selected from the group consisting of 7-methoxy-2-oxo-8-pentyloxy-1,2-dihydroquinoline-3-carboxylic acid (2-pyridine-4-ylethyl) amide (Example 3-1); 7-methoxy-2-oxo-8-pentyloxy-1,2- dihydroquinoline-3-carboxylic acid (4-aminobenzyl)amide (Example 3-2); 7-methoxy-2-oxo-8-pentyloxy-1,2-dihydroquinoline-3-carboxylic acid [2-(4-aminophenyl)ethyl]amide (Example 3-3); 7-methoxy-2-oxo-8-pentyloxy-1,2-dihydroquinoline-3-carboxylic acid (4-aminophenyl)amide hydrochloride (Example 3-4); 7-methoxy-2-oxo-8-pentyloxy-1,2-dihydroquinoline-3-carboxylic acid (3,4-methylenedioxybenzyl) amide (Example 3-5); 8-ethoxy-7-methoxy-2-oxo-1,2-dihydroquinoline-3-carboxylic acid (2-pyridine-4-ylethyl)amide (Example 3-6); 7-methoxy-2-oxo-8-pentyloxy-1,2-dihydroquinoline-3-carboxylic acid [2-(4-hydroxyphenyl)ethyl]amide (Example 3-7); 7-methoxy-2-oxo-8-pentyloxy-1,2-dihydroquinoline-3-carboxylic acid [2-(4-fluorophenyl)ethyl]amide (Example 3-B); 7-methoxy-2-oxo-8-pentyloxy-1,2-dihydroquinoline-3-carboxylic acid (4-pyridyl methyl)amide (Example 3-9); 7-methoxy-2-oxo-S-pentyloxy-1,2-dihydroquinoline-3-carboxylic acid (2-piperidinoethyl)amide (Example 3-10); 7-methoxy-2-oxo-8-pentyloxy-1,2-dihydroquinoline-3-carboxylic acid (2-morpholinoethyl)amide (Example 3-11); 7-methoxy-2-oxo-8-pentyloxy-1,2-dihydroquinoline-3-carboxylic acid (3-pyridylmethyl)amide (Example 3-12); 7-methoxy-2-oxo-8-pentyloxy-1,2-dihydroquinoline-3-carboxylic acid (2-pyridylmethyl)amide (Example 3-13); 3-butoxy-7-methoxy-2-oxo-1,2-dihydroquinoline-3-carboxylic acid (2-phenylethyl)amide (Example 3-14); 8-butoxy-7-methoxy-2-oxo-1,2-dihydroquinoline-3-carboxylic acid [2-(4-fluorophenyl)ethyl]amide (Example 3-15); 8-butoxy-7-methoxy-2-oxo-1,2-dihydroquinoline-3-carboxylic acid (2-pyridine-4-ylethyl)amide (Example 3-16); 8-butoxy-7-methoxy-2-oxo-1,2-dihydroquinoline-3-carboxylic acid (2-pyridine-4-ylethyl)amide hydrochloride (Example 3-17); 8-ethoxy-7-methoxy-2-oxo-1,2-dihydroquinoline-3-carboxylic acid [2-(4-fluorophenyl)ethyl]amide (Example 3-18); 7-methoxy-2-oxo-8-pentyloxy-1,2-dihydroquinoline-3-carboxylic acid [2-(2-fluorophenyl)ethyl]amide (Example 3-19); 7-methoxy-2-oxo-8-pentyloxy-1,2-dihydroquinoline-3-carboxylic acid [2-(3-fluorophenyl)ethyl]amide (Example 3-20); 7-methoxy-2-oxo-8-pentyloxy-1,2-dihydroquinoline-3-carboxylic acid [2-(4-hydroxy-3-methoxyphenyl)ethyl]amide (Example 3-21); 7-methoxy-2-oxo-8-pentyloxy-1,2-dihydroquinoline-3-carboxylic acid [2-(4-chlorophenyl)ethyl]amide (Example 3-22); 7-methoxy-2-oxo-8-pentyloxy-1,2-dihydroquinoline-3-carboxylic acid (2-phenylethyl)amide (Example 3-23); 7-methoxy-2-oxo-8-pentyloxy-1,2-dihydroquinoline-3-carboxylic acid (4-methylbenzyl)amide (Example 3-24); 7-methoxy-2-oxo-8-pentyloxy-1,2-dihydroquinoline-3-carboxylic acid (4-fluorobenzyl)amide (Example 3-25); 7-methoxy-2-oxo-8-propoxy-1,2-dihydroquinoline-3-carboxylic acid (2-pyridine-4-ylethyl)amide (Example 3-26); 7-methoxy-2-oxo-8-propoxy-1,2-dihydroquinoline-3-carboxylic acid [2-(4-fluorophenyl) ethyl]amide (Example 3-27); 7-methoxy-2-oxo-8-propoxy-1,2-dihydroquinoline-3-carboxylic acid [2-(4-hydroxyphenyl)ethyl]amide (Example 3-28), 7-methoxy-2-oxo-8-propoxy-1,2-dihydroquinoline-3-carboxylic aid (3,4-methylenedioxybenzyl)amide (Example 3-29); 7-methoxy-2-oxo-8-propoxy-1,2-dihydroquinoline-3-carboxylic acid (2-phenylethyl)amide (Example 3-30); 7,8-dimethoxy-2-oxo-1,2-dihydroquinoline-3-carboxylic acid [2-(4-fluorophenyl)ethyl]amide (Example 3-31); 7-methoxy-2-oxo-6-pentyloxy-1,2-dihydroquinoline-3-carboxylic acid [2-(4-fluorophenyl)ethyl]amide (Example 3-32); 7-methoxy-2-oxo-6-pentyloxy-1,2-dihydroquinoline-3-carboxylic acid (3,4-methylenedioxybenzyl)amide (Example 3-33); 7-methoxy-2-oxo-6-pentyloxy-1,2-dihydroquinoline-3-carboxylic acid (2-morpholinoethyl)amide (Example 3-34); 8-ethoxy-7-methoxy-2-oxo-1,2-dihydroquinoline-3-carboxylic acid (3,4-methylenedioxybenzyl) amide (Example 3-35); 1-methyl-7-methoxy-2-oxo-8-pentyloxy-1,2-dihydroquinoline-3-carboxylic acid [2-(4-fluorophenyl)ethyl]amide (Example 3-36); 1-methyl-7-methoxy-2-oxo-8-pentyloxy-1,2-dihydroquinoline-3-carboxylic acid (2-pyridine-4-ylethyl)amide (Example 3-37); 1-methyl-7-methoxy-2-oxo-8-pentyloxy-1,2-dihydroquinoline-3-carboxylic acid (2-morpholinoethyl) amide (Example 3-38); 1-methyl-7-methoxy-2-oxo-8-pentyloxy-1,2-dihydroquinoline-3-carboxylic acid (4-pyridylmethyl) amide (Example 3-39); 1-methyl-7-methoxy-2-oxo-8-pentyloxy-1,2-dihydroquinoline-3-carboxylic acid (4-fluorobenzyl)amide (Example 3-40); 1-methyl-7-methoxy-2-oxo-8-pentyloxy-1,2-dihydroquinoline-3-carboxylic acid [2-(4-hydroxyphenyl)ethyl]amide (Example 3-41); 1-methyl-7-methoxy-2-oxo-8-pentyloxy-1,2-dihydroquinoline-3-carboxylic acid (3,4-methylenedioxybenzyl) amide (Example 3-42); 1-methyl-7-methoxy-2-oxo-6-pentyloxy-1,2-dihydroquinoline-3-carboxylic acid [2-(4-fluorophenyl)ethyl]amide (Example 3-43); 1-methyl-7-methoxy-2-oxo-6-pentyloxy-1,2-dihydroquinoline-3-carboxylic acid (2-morpholinoethyl) amide (Example 3-44); 1-methyl-7-methoxy-2-oxo-6-pentyloxy-1,2-dihydroquinoline-3-carboxylic acid (3,4-methylenedioxybenzyl)amide (Example 3-45), 7,8-dipentyloxy-2-oxo-1,2-dihydroquinoline-3-carboxylic acid [2-(4-fluorophenyl)ethyl]amide (Example 3-46); 8-hydroxy-7-methoxy-2-oxo-1,2-dihydroquinoline-3-carboxylic acid (3,4-methylenedioxybenzyl)amide (Example 3-47); 7-methoxy-2-oxo-8-pentyloxy-1,2-dihydroquinoline-3-carboxylic acid (3,4-dihydroxybenzyl)amide (Example 3-48); 7-methoxy-2-oxo-8-pentyloxy-1,2-dihydroquinoline-3-carboxylic acid (4-hydroxy-3-methoxybenzyl)amide (Example 3-49); 1-O-(2-hydroxy-5-[(7-methoxy-2-oxo-8-pentyloxy-1,2-dihydro-3-quinolyl)carbonylamino methyl]phenyl)glucosidouronic acid and 1-O-(2-hydroxy-4-[(7-methoxy-2-oxo-8-pentyloxy-1,2-dihydro-3-quinolyl)carbonylamino methyl]phenyl}glucosidouronic acid (Example 3-50); 5-[7-methoxy-3-{(3,4-methylenedioxybenzyl)carbamoyl}-2-oxo-1,2-dihydro-8-quinolyloxy]pentanoic acid (Example 3-51); 5-[7-methoxy-3-{(3-hydroxy-4-methoxybenzyl)carbamoyl}-2-oxo-1,2-dihydro-8-quinolyloxy]pentanoic acid (Example 3-52); 8-(5-hydroxypentyloxy)-7-methoxy-2-oxo-1,2-dihydroquinoline-3-carboxylic acid (3,4-methylenedioxybenzyl)amide (Example 3-53); 8-(5-hydroxypentyloxy)-7-methoxy-2-oxo-1,2-dihydroquinoline-3-carboxylic acid (4-hydroxy-3-methoxybenzyl)amide (Example 3-54); 8-(4-hydroxypentyloxy)-7-methoxy-2-oxo-1,2-dihydroquinoline-3-carboxylic acid (3,4-methylenedioxybenzyl)amide (Example 3-55); 7-methoxy-2-oxo-8-(4-oxopentyloxy)-1,2-dihydroquinoline-3-carboxylic acid (3,4-methylenedioxybenzyl)amide (Example 3-56); 8-(3-hydroxypentyloxy)-7-methoxy-2-oxo-1,2-dihydroquinoline-3-carboxylic acid (3,4-methylenedioxybenzyl)amide (Example 3-57); 7-methoxy-2-oxo-8-(3-oxopentyloxy)-1,2-dihydroquinoline-3-carboxylic acid (3,4-methylenedioxybenzyl)amide (Example 3-58); 8-(2-hydroxypentyloxy)-7-methoxy-2-oxo-1,2-dihydroquinoline-3-carboxylic acid (3,4-methylenedioxybenzyl)amide (Example 3-59); 7,8-dihydroxy-2-oxo-1,2-dihydroquinoline-3-carboxylic acid [2-(4-fluorophenyl)ethyl]amide (Example 4-1); 8-butoxy-3-hydroxy methyl-7-methoxy-2-oxo-1,2-dihydroquinoline (Example 5-1); 8-ethoxy-3-hydroxymethyl-7-methoxy-2-oxo-1,2-dihydroquinoline (Example 5-2); N-(4-fluorophenyl)carbamic acid (8-butoxy-7-methoxy-2-oxo-1,2-dihydroquinoline-3-yl)methyl ester (Example 6-1); N-pyridine-4-ylcarbamic acid (8-ethoxy-7-methoxy-2-oxo-1,2-dihydroquinoline-3-yl)methyl ester (Example 6-2); 3-dimethyl aminomethyl-8-ethoxy-7-methoxy-2-oxo-1,2-dihydroquinoline (Example 7-1); 8-butoxy-3-aminomethyl-7-methoxy-2-oxo-1,2-dihydroquinoline (Example 7-2); 8-ethoxy-7-methoxy-3-morpholinomethyl-2-oxo-1,2-dihydroquinoline (Example 7-3); N-[(8-butoxy-7-methoxy-2-oxo-1,2-dihydroquinoline-3-yl)methyl]-N'-(4-fluorophenyl)urea (Example 8-1) and N-[(8-butoxy-7-methoxy-2-oxo-1,2-dihydroquinoline-3-yl)methyl]-(4-hydroxyphenyl)acetamide (Example 8-2).

(19) A 2-oxoquinoline compound or its pharmaceutically acceptable salt, the 2-oxoquinoline compound being selected from the group consisting of 7-methoxy-2-oxo-8-pentyloxy-1,2-dihydroquinoline-3-carboxylic acid methyl ester (Example 1-1); 7-methoxy-2-oxo-6-pentyloxy-1,2-dihydroquinoline-3-carboxylic acid methyl ester (Example 1-2); 1-methyl-7-methoxy-2-oxo-8-pentyloxy-1,2-dihydroquinoline-3-carboxylic acid methyl ester (Example 1-3); and 1-methyl-7-methoxy-2-oxo-6-pentyloxy-1,2-dihydroquinoline-3-carboxylic acid methyl ester (Example 1-4),

(20) A 2-oxoquinoline compound or its pharmaceutically acceptable salt, the 2-oxoquinoline compound being selected from the group consisting of 7-methoxy-2-oxo-8-pentyloxy-1,2-dihydroquinoline-3-carboxylic acid (Example 2-1); 8-butoxy-7-methoxy-2-oxo-1,2-dihydroquinoline-3-carboxylic acid (Example 2-2); 8-ethoxy-7-methoxy-2-oxo-1,2-dihydroquinoline-3-carboxylic acid (Example 2-3); 7-methoxy-2-oxo-8-propoxy-1,2-dihydroquinoline-3-carboxylic acid (Example 2-4); 7-methoxy-2-oxo-6-pentyloxy-1,2-dihydroquinoline-3-carboxylic acid (Example 2-5); 1-methyl-7-methoxy-2-oxo-8-pentyloxy-1,2-dihydroquinoline-3-carboxylic acid (Example 2-6); and 1-methyl-7-methoxy-2-oxo-6-pentyloxy-1,2-dihydroquinoline-3-carboxylic acid (Example 2-7).

(21) 7-Methoxy-2-oxo-8-pentyloxy-1,2-dihydroquinoline-3-carboxamide (Example 3-60) or its pharmaceutically acceptable salt.

(22) A pharmaceutical composition comprising, as an active ingredient, the 2-oxoquinoline compound of any one of (3)–(21) or its pharmaceutically acceptable salt.

(23) A cannabinoid receptor modulator comprising, as an active ingredient, the 2-oxoquinoline compound of any one of (3)–(21) or its pharmaceutically acceptable salt.

(24) A peripheral cannabinoid receptor modulator comprising, as an active ingredient, the 2-oxoquinoline compound of any one of (3)–(21) or its pharmaceutically acceptable salt, the 2-oxoquinoline compound selectively acting on peripheral type cannabinoid receptors.

(25) The 2-oxoquinoline compound of any one of (3)–(21) or its pharmaceutically acceptable salt, wherein the 2-oxoquinoline compound is an immunomodulator, therapeutic agent for autoimmune diseases, antiallergic agent, or antiinflammatory agent.

(26) The 2-oxoquinoline compound of any of (3)–(21) or its pharmaceutically acceptable salt, wherein the 2-oxoquinoline compound is an antiinflammatory agent.

(27) An antiinflammatory agent comprising, as an active ingredient, the 2-oxoquinoline compound of (1) or (2) or its pharmaceutically acceptable salt.

Terminologies used herein are defined as follows:

The term "alkyl" means group having 1–10 carbon atoms, which may be linear or branched, and specifically includes methyl, ethyl, propyl, isopropyl, butyl, isobutyl, s-butyl, t-butyl, pentyl, isopentyl, neopentyl, t-pentyl, hexyl, isohexyl, neohexyl, heptyl, etc.

The group in $R^2$, $R^{2'}$, $R^5$, and $R^6$ preferably contains 1–7 carbon atoms; more preferred in $R^6$ is a linear alkyl containing 1–6 carbon atoms and still more preferred in $R^6$ is methyl. Preferably, the group in $R^3$ and $R^4$ has 1–4 carbon atoms. The group in $R^1$, $R^7$, $R^8$ and $R^9$ is preferably a linear alkyl having 1–6 carbon atoms; more preferred is ethyl, propyl, butyl or pentyl; still more preferred is propyl, butyl or pentyl; and particularly preferred is pentyl. The group in $R^{10}$, $R^{11}$, $R^{12}$ and $R^{13}$ preferably has 1–4 carbon atoms; preferred in $R^a$, $R^b$, $R^c$, $R^d$, $R^e$, $R^{e'}$ and $R^f$ is 1–4 carbon atoms; and more preferred is methyl.

The term "alkenyl" means the linear or branched group having 2–10 carbon atoms, and is specifically exemplified by vinyl, allyl, crotyl, 2-pentenyl, 3-pentenyl, 2-hexenyl, 3-hexenyl, heptenyl, etc.

The group in $R^6$, $R^7$, $R^8$ and $R^9$ preferably contains 2–7 carbon atoms. Preferably $R^1$ contains 4–7 carbon atoms.

The term "alkynyl" means a linear or branched group having 2–10 carbon atoms, and is specifically exemplified by ethynyl, propynyl, butynyl, 2-pentynyl, 3-pentynyl, 2-hexynyl, 3-hexynyl, hepynyl, etc.

The group in $R^6$, $R^7$, $R^8$ and $R^9$ preferably contains 2–7 carbon atoms. Preferably $R^1$ contains 4–7 carbon atoms.

The "alkylene" in $Alk^a$, $Alk^b$ and $Alk^c$ means a linear or branched chain having 1–4 carbon atoms, which is specifically exemplified by methylene, ethylene, trimethylene, tetramethylene, etc., and more preferred is methylene or ethylene. Particularly preferred is methylene for $Alk^a$; and particularly preferred is methylene for each of $Alk^b$ and $Alk^c$.

The "alkenylene" in $Alk^a$, $Alk^b$ and $Alk^c$ means a linear or branched chain having 2–4 carbon atoms, which is specifically exemplified by vinylene, propenylene, butenylene, etc.

The term "alkoxy" means the group of which alkyl portion corresponds to that having 1–4 carbon atoms among the above-defined alkyl groups, which is specifically exemplified by methoxy, ethoxy, propoxy, iospropyloxy, butyloxy, t-butyloxy, etc.

The term "cycloalkyl" means a saturated monocyclic alkyl having 3–8 carbon atoms, which is specifically exemplified by cyclopropyl, cyclobutyl, cyclopentyl, cyclohexyl, cycloheptyl, etc.

Preferably the group in $R^1$, $R^6$, $R^7$ and $R^8$ contains 3–6 carbon atoms; preferably R contains 3–7 carbon atoms and particularly preferred is cyclohexyl.

The "cycloalkylalkyl" in $R^1$, $R^6$, $R^7$ and $R^8$ means the group in which the cycloalkyl portion is the above-defined cycloalkyl containing 3–6 carbon atoms and the alkyl portion is the above-defined alkyl containing 1–4 carbon atoms. Specifically, the group is exemplified by cyclopropylmethyl, cyclobutylmethyl, cyclopentylmethyl, cyclohexylmethyl, cyclopropylethyl, cyclopropylpropyl, cyclopropylbutyl, etc.

The "aryl" in $R^1$, $R^6$, $R^7$, $R^8$ and R means an aromatic hydrocarbon having 6–16 carbon atoms and is specifically exemplified by phenyl, naphthyl, biphenyl, anthracenyl, indenyl, azulenyl, fluorenyl, phenanthrenyl, pyrenyl, etc.; preferred is phenyl or naphthyl; and particularly preferred is phenyl.

The "arylalkyl" in $R^1$, $R^6$, $R^7$, $R^8$, $R^{12}$ and $R^{13}$ means the group in which the aryl portion corresponds to the above-defined aryl and the alkyl portion is the above-defined alkyl having 1–4 carbon atoms. Specifically, the group is exemplified by benzyl, phenethyl, phenylpropyl, phenylbutyl, naphthylmethyl, biphenylmethyl, etc.; and preferred is benzyl.

The "heteroaryl" in $R^1$, $R^6$, $R^7$, $R^8$ and R may be saturated or unsaturated with hydrogen atom and is specifically exemplified by pyridyl, pyrimidyl, pyrazinyl, pyridazinyl, pyrazolyl, imidazolyl, thiazolyl, isothiazolyl, oxazolyl, isooxazolyl, tetrazolyl, thiadiazolyl, oxadiazolyl, triazinyl, triazolyl, thienyl, pyrrolyl, pyrrolinyl, furyl, azepinyl, benzopyranyl, benzothienyl, benzotriazolyl, indolyl, isoindolyl, quinolyl, isoquinolyl, cinnolinyl, phthalazinyl, quinazolinyl, quinoxalinyl, 1,8-naphthyridyl, 1,7-naphthyridyl, 1,6-naphthyridyl, 1,5-naphthyridyl, pyrido[2,3-d]pyrimidyl, thieno [2,3-b]pyridyl, pyrrolidinyl, imidazolidinyl, piperidyl, piperazinyl, morpholyl, hydroazepinyl, hydroindolyl, hydroisoindolyl, hydroquinolyl, hydroisoquinolyl, etc; preferred is pyridyl, thienyl, piperidyl, piperidino, imidazolyl, or morpholyl; more preferred is pyridyl, piperidyl, or morpholyl; and particularly preferred is pyridyl.

The expression, $R^e$ and $R^{e'}$ "together with the adjacent nitrogen atom, form a heteroaryl," means a heteroaryl having one or more nitrogen atoms among above heteroaryl groups; specifically, the group includes pyrrolidinyl, imidazolidinyl, piperidino, piperazinyl, morpholino, pyrazolyl, imidazolyl, tetrazolyl, triazolyl, pyrrolyl, pyrrolinyl, indolyl, hydroazepinyl, hydroindolyl, hydroisoindolyl, hydroquinolyl, hydroisoquinolyl, etc.; preferred is morpholino, piperidino or piperazinyl; and particularly preferred is morpholino.

The expression, $R^7$ and $R^8$, or $R^{10}$ and $R^{11}$, "together with the adjacent nitrogen atom, form a heteroaryl" has the same meaning as the above-defined expression, $R^e$ and $R^{e'}$ "together with the adjacent nitrogen atom, form a heteroaryl."

The "heteroarylalkyl" in $R^1$, $R^6$, $R^7$ and $R^a$ means the group in which the heteroaryl portion is the same as the above-defined one and the alkyl portion corresponds to the above-defined alkyl having 1–4 carbon atoms; specifically, the group is exemplified by 2-thienylmethyl, 3-furylmethyl, 4-pyridylmethyl, 2-quinolylmethyl, 3-isoquinolylmethyl, etc.; and preferred is 4-pyridylmethyl.

The "benzene-condensed cycloalkyl" in R means the group of which cycloalkyl portion is the above-defined cycloalkyl; specifically, the group is exemplified by tetrahydronaphthalene, indan, etc.; and preferred is tetrahydronaphthalene.

The "acyl" in $R^7$ and $R^8$ means a group in which carbonyl has been substituted with the above-defined alkyl or the above-defined aryl; specifically, the group is exemplified by formyl, acetyl, propionyl, butyryl, valeryl, benzoyl, naphthoyl, etc.

Further, each of substituted or unsustituted groups may be substituted or unsustituted with one or more substituents, preferably with 1 or 2 substituents Groups to be used as the substituents are described below.

The term "halogen atom" means fluorine, chlorine, bromine and iodine; and preferred are fluorine and chlorine.

The terms "alkyl", "alkoxy" and "acyl" indicate the same meanings as the above-defined "alkyl", "alkoxy" and "acyl," respectively.

The "alkoxycarbonyl" means the group of which alkyl portion is the above-defined alkyl having 1–4 carbon atoms; specifically, the group is exemplified by methoxycarbonyl, ethoxycarbonyl, propoxycarbonyl, butoxycarbonyl, etc.; and preferred is ethoxycarbonyl.

The "alkylamino" means the group of which alkyl portion corresponds to the above-defined alkyl having 1–4 carbon atoms; specifically, the group is exemplified by methylamino, ethylamino, propylamino, butylamino, dimethylamino, diethylamino, etc.

The "alkylthio" means the group of which alkyl portion is the above-defined alkyl having 1–4 carbon atoms; specifically, the group is exemplified by methylthio, ethylthio, propylthio, butylthio, etc.

The "alkylsulfinyl" means the group of which alkyl portion corresponds to the above-defined alkyl having 1–4 carbon atoms; specifically, the group is exemplified by methylsulfinyl, ethylsulfinyl, propylsulfinyl, butylsulfinyl, etc.

The "alkylsulfonyl" means the group of which alkyl portion is the above-defined alkyl having 1–4 carbon atoms; specifically, the group is exemplified by methylsulfonyl, ethylsulfonyl, propylsulfonyl, butylsulfonyl, etc.

The "alkenyloxy" means the group of which alkenyl portion corresponds to the above-defined alkyl having 2–4 carbon atoms; specifically, the group is exemplified by ethenyloxy, propenyloxy, butenyloxy, etc.

The "acyloxy" means the group of which acyl portion is as defined above and is specifically exemplified by formyloxy, acetyloxy, propionyloxy, butyryloxy, isobutyryloxy, etc.; and preferred is acetyloxy.

The "acylthio" means the group of which acyl portion is as defined above and is specifically exemplified by formylthio, acetylthio, propionylthio, butyrylthio, isobutyrylthio, etc.; and preferred is acetylthio.

The "acylamino" means the group of which acyl portion is as defined above and is specifically exemplified by formylamino, acetylamino, propionylamino, butyrylamino, etc.; and preferred is acetylamino.

The "aralkyloxy" means the group of which aralkyl portion is the above-defined arylalkyl; and the group is specifically exemplified by benzyloxy, phenethyloxy, phenylpropyloxy, phenylbutyloxy, naphthylmethyloxy, biphenylmethyloxy, etc.

Preferred for $R^a$ is hydrogen atom.

Substitution positions for the pair of $WR^1$ and $R^2$ are selected from the group consisting of position-g, position-h, position-i and position-j of 2-oxoquinoline but the respective substitution positions are different from each other. Preferred combination of the substitution positions is the combination of positions-h and -i, or that of positions-i and -j on the ring of 2-oxoquinoline; particularly preferred is the combination of positions-i and -j. It is preferable that $R^2$ is substituted at position-i.

Preferred for W is —O—, —S(O)$_t$— or —NR$^5$—; more preferred is —O—. When W is —S(O)$_t$—, then t is preferred to be 0; when W is —NR$^5$—, then it is preferable that $R^5$ is a hydrogen atom Preferred for $R^1$ is a hydrogen atom or alkyl; more preferred is alkyl; and particularly preferred is unsubstituted alkyl.

Preferred substituents of alkyl include alkylamino, amino, hydroxy, alkoxy, alkoxycarbonyl, acyl, acyloxy, acylthio, mercapto, alkylthio, alkylsulfinyl and alkylsulfonyl; particularly preferred is hydroxy, carboxy or acyl. Alkyl, which has been substituted with any of hydroxy, carboxy, and acyl, is preferred to have 5 carbon atoms in total.

Specific examples of particularly preferred substituted alkyl include 2-hydroxypentyl, 3-hydroxypentyl, 4-hydroxypentyl, 5-hydroxypentyl, 2-oxopentyl, 3-oxopentyl, 4-oxopentyl, and 4-carboxybutyl.

Preferred for $R^2$ are the respective groups except hydrogen atom; specifically, such groups are alkyl, —OR$^6$, —NR$^7$R$^8$ and —(CH$_2$)$_u$'—S(O)$_u$R$^9$ (where each symbol is as defined above); more preferred are —OR⁶, —NR⁷R⁸ and —(CH₂)ᵤ'—S(O)ᵤR₉; and particularly preferred is —OR⁶.

When R² is —OR⁶, then preferred for R⁶ is hydrogen atom or alkyl; particularly preferred is alkyl. When R² is —NR⁷R⁸, then it is preferable that one of R⁷ and R⁸ is hydrogen atom and the other is alkyl. When R² is —(CH₂)ᵤ'—S(O)ᵤR⁹, preferred for u' and u is 0, and preferred for R⁹ is alkyl.

Preferred for X are —COORᵇ, —CONRᶜ-(Alkᵃ)ᵣ-R, —(CH₂)ₚ—OC(=Y)—NRᵈ-(Alkᵇ)ₛ-R, —(CH₂)_q—NRᵉ—C(=Z)—(NRᶠ)_w-(Alkᶜ)ᵥ-R, —(CH₂)ₚ—OH and —(CH₂)_q—NRᵉRᵉ'
(where each symbol has the same meaning as defined above); particularly preferred is —COORᵇ or —CONRᶜ(Alkᵃ)ᵣ-R; and more preferred for X and X' is —CONRᶜ-(Alkᵃ)ᵣ-R; in this case, preferred for Rᶜ is hydrogen atom.

When X and X' are —(CH₂)ₚ—OC(=Y)—NRᵈ-(Alkᵇ)ₛ-R and —(CH₂)_q—NRᵉ—C(=Z)—(NRᶠ)_w-(Alkᶜ)ᵥ-R, then preferred for Y and Z is oxygen atom; preferred for p and q is 1; preferred for w is 1; preferred for s and v is 0; and preferred for Rᵉ, Rᵈ and Rᶠ is hydrogen atom.

Preferred for R is aryl, heteroaryl or

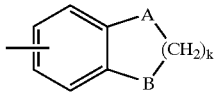

(where each symbol has the same meaning as defined above); more preferred is

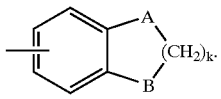

In the above general formula, preferred for both A and B is oxygen atom and k is preferably 1.

Preferably, R is unsubstituted or has substituent of alkyl substituted or unsubstituted with hydroxy or of hydroxy, alkoxy, alkenyloxy, acyl, acyloxy, halogen atom, nitro, amino, sulfonamide, alkylamino, aralkyloxy, pyridyl, piperidino, carboxy, alkoxycarbonyl, acylamino, aminocarbonyl, cyano or glucuronic acid residue; and when R has substituents, then the number of substituents is preferably 1 or 2. More preferred is alkyl that may be substituted or unsubstituted with hydroxy or is a hydroxy, alkoxy, halogen atom or glucuronic acid residue; further preferred is alkyl that may be substituted or unsubstituted with hydroxy or is a hydroxy, alkoxy or halogen atom; particularly preferred is methyl group, hydroxy or methoxy. When R is phenyl group, substitution position(s) of the substituent(s) is preferably located at the 4-position in the case of monosubstitution or the 3- and 4-positions in the case of di-substitution.

Specifically, preferred for R is 4-methylphenyl, 4-hydroxyphenyl, 3,4-dihydroxyphenyl, 4-hydroxy-3-methoxyphenyl, 2-fluorophenyl, 3-fluorophenyl, 4-fluorophenyl, 4-chlorophenyl, 3-(6-carboxy-3,4,5-trihydroxy-2-pyranyloxy)-4-hydroxyphenyl or 4-(6-carboxy-3,4,5-trihydroxy-2-pyranyloxy)-3-hydroxyphenyl; and particularly preferred are 3,4-dihydroxy phenyl and 4-hydroxy-3-methoxyphenyl.

The "pharmaceutically acceptable salt" specifically includes but is not limited to salts of alkaline metals such as sodium salts, potassium salts, cesium salts, etc; salts of alkaline earth metals such as calcium salts, magnesium salts, and such; organic amine salts such as triethylamine salts, pyridine salts, picoline salts, ethanolamine salts, triethanolamine salts, dicyclohexylamine salts, N,N'-dibenzylethylenediamine salts, and such; salts of inorganic acids such as hydrochloride, hydrobromide, sulfate, phosphate, etc.; salts of organic acids such as formate, acetate, trifluoroacetate, maleate, tartrate, etc.; sulfonates such as methanesulfonate, benzenesulfonate, p-toluenesulfonate, and such; salts of amino acids such as arginine salts, aspartates, glutamates, etc.

Diseases associated with the cannabinoid receptor include autoimmune diseases (e.g., systemic lupus erythematosus, rheumatoid arthritis, ulcerative colitis, etc.) and inflammatory diseases (e.g., acute and chronic pancreatites, etc.). Particularly, the inventive compound can preferably be used to treat chronic pancreatitis that is hard to be treated with commonly used anti-inflammatory agents.

The "cannabinoid receptor modulator" means an agent capable of regulating the biological activity of cannabinoid receptors, or an agent capable of regulating the expression of cannabinoid receptors; the former includes agonist, antagonist, inverse agonist, and agent capable of enhancing or reducing the sensitivity of cannabinoid receptors; and the latter includes agents capable of enhancing or suppressing the expression of cannabinoid receptors.

The present invention also includes a variety of isomers, prodrugs, metabolites, hydrates, and solvates of the respective compounds.

The term "prodrug" means derivatives of the inventive compounds having chemically or metabolically decomposable groups therein and thus capable of being converted to the original compounds having the inherent drug effects after administered into the living body, and which also includes non-covalent complexes and salts thereof.

Compound [I] can be produced, for example, as follows, but the method is not limited thereto.

Production method 1

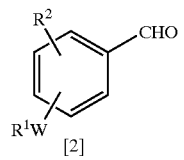

[2]

1st step ↓

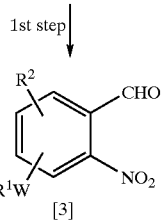

[3]

2nd step ↓

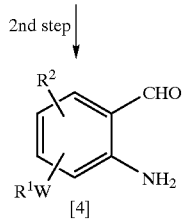

[4]

3rd step 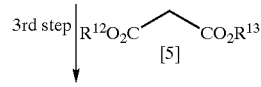

[5]

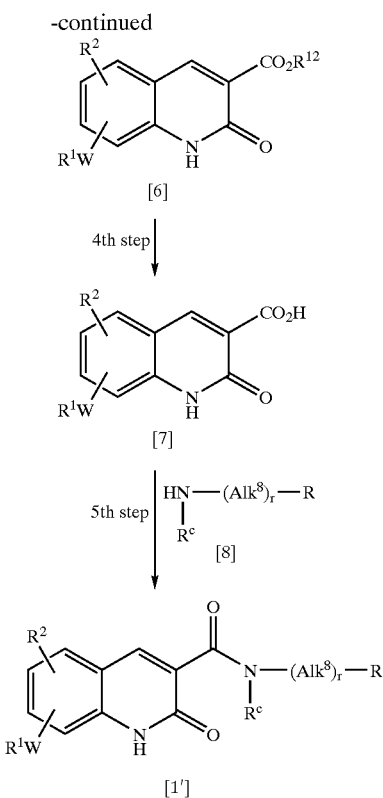

In this formula, $R^{12}$ and $R^{13}$ may be identical or different and represent hydrogen, alkyl, arylalkyl or cyano; other symbols have the same meaning as defined above.

(Step 1)

Shown in this step is a method to obtain compound [3] by nitrating the ortho-position of formyl group on the benzene ring of compound [2].

It is possible to obtain a nitro compound by reacting compound [2] with fuming nitric acid in the presence of concentrated sulfuric acid in a solvent.

Such a solvent includes, for example, ether solvents such as diethyl ether, 1,2-dimethoxyethane, tetrahydrofuran, diglyme, and such; halogen solvents such as dichloromethane, chloroform, carbon tetrachloride, 1,2-dichloroethane, and such; ester solvents such as ethyl acetate, methyl acetate, butyl acetate, and such; alcohol solvents such as methanol, ethanol, isopropyl alcohol, t-butanol, etc.; and acid solvents such as acetic acid, acetic anhydride, and such; and preferred is acetic acid.

The reaction temperature is generally −50–200° C., and preferably −10–60° C. The reaction time is generally 15 minutes–48 hours, preferably 1–8 hours. The resulting nitro compound can further be reacted with an alkyl bromide such as bromopentane, etc. in the presence of a base in an adequate solvent to give compound [3].

The suitable base includes, for example, sodium carbonate, potassium carbonate, lithium carbonate, sodium bicarbonate, potassium bicarbonate, sodium hydroxide, potassium hydroxide, lithium hydroxide, sodium hydride, n-butyllithium, s-butyllithium, t-butyllithium, and lithium diisopropylamide; and preferred is potassium carbonate.

The adequate solvent includes, for example, hydrocarbon solvents such as benzene, toluene, xylene, hexane, etc.; ether solvents such as diethyl ether, 1,2-dimethoxyethane, tetrahydrofuran, diglyme, and such; halogen solvents such as dichloromethane, chloroform, carbon tetrachloride, 1,2-dichloroethane, and such; ester solvents such as ethyl acetate, methyl acetate, butyl acetate, and such; polar solvents such as dimethylformamide, dimethyl sulfoxide, acetonitrile, acetone, etc.; alcohol solvents such as methanol, ethanol, isopropyl alcohol, t-butanol, and such; and preferred is dimethylformamide.

The reaction temperature is generally −10–200° C., preferably 0–60° C. The reaction time is generally 15 minutes–48 hours, preferably 1–8 hours.

(Step 2)

Compound [4] can be obtained by reducing the nitro group of compound [3] according to a commonly used method.

(Step 3)

Compounds [4] can be condensed with a malonic acid derivative [5] in the presence of an adequate acid or base to give compound [6]. The malonic acid derivative includes, for example, diethyl malonate, dimethyl malonate, dibenzyl malonate, ethyl cyanoacetate, methyl cyanoacetate, and such; and preferred is dimethyl malonate. The adequate acid includes, for example, benzoic acid, p-toluenesulfonic acid, acetic acid, methanesulfonic acid, hydrochloric acid, sulfuric acid, nitric acid, and such; benzoic acid is preferably used. The base includes, for example, sodium hydride, potassium t-butoxide, sodium ethoxide, sodium methoxide, ammonium acetate, sodium acetate, piperidine, pyridine, pyrrolidine, n-methylmorpholine, morpholine, triethylamine, and such; and preferred is piperidine.

The solvent includes, for example, hydrocarbon solvents such as benzene, toluene, xylene, hexane, heptane, etc.; ether solvents such as diethyl ether, 1,2-dimethoxyethane, tetrahydrofuran, diglyme, etc; ester solvents such as ethyl acetate, methyl acetate, butyl acetate, etc.; polar solvents such as dimethylformamide, dimethylsulfoxide, acetonitrile, acetone, etc.; and alcohol solvents such as methanol, ethanol, isopropyl alcohol, t-butanol, etc.; and preferred is toluene.

The reaction temperature is generally 0–150° C., and preferably 120° C. The reaction time is generally 2–48 hours, and preferably 24 hours.

(Step 4)

Compound [6] can be hydrolyzed in the presence of an adequate base in a solvent to give compound [7].

The solvent includes alcohol solvents such as methanol, ethanol, isopropyl alcohol, t-butanol, and such; water; or a mixed solvent thereof.

The suitable base includes, for example, sodium carbonate, potassium carbonate, lithium carbonate, sodium bicarbonate, potassium bicarbonate, sodium hydroxide, potassium hydroxide, lithium hydroxide, sodium hydride, n-butyllithium, s-butyllithium, t-butyllithium, lithium diisopropylamide, and such; and preferred is lithium carbonate.

(Step 5)

Compound [7] that has been converted to an activated carboxylic acid derivative is allowed to react to compound [8] to yield compound [I] of interest.

The activated carboxylic acid derivative includes, for example, acid halide that can be obtained by treating carboxylic acid with thionyl chloride, phosphorus oxychloride, phosphorus pentachloride, oxalyl chloride, and such; active ester that can be obtained by condensing carboxylic acid with 1-hydroxybenzotriazole, N-hydroxysuccinimide or the like by using a condensing agent such as dicyclohexylcarbodiimide (DCC), 1-ethyl-3-(3-dimethylaminopropyl) carbodiimide (EDC) hydrochloride, and such; mixed acid anhydride that can be obtained by reacting carboxylic acid to ethyl chlorocarbonate, pivaloyl chloride, isobutyl chlorocarbonate or the like, and such; preferably used is active ester that can be obtained from N-hydroxybenzotriazole by using EDC hydrochloride as a condensing agent.

If required, it is also possible to use a base in combination in the above reaction.

The base includes, for example, organic amines such as triethylamine, pyridine, and N-methylmorpholine; and preferred is triethylamine.

The solvent includes, for example, hydrocarbon solvents such as benzene, toluene, hexane, xylene, and such; ether solvents such as diethyl ether, 1,2-dimethoxyethane, tetrahydrofuran, diglyme, and such; halogen solvents such as dichloromethane, chloroform, carbon tetrachloride, 1,2-dichloroethane, and such; ester solvents such as ethyl acetate, methyl acetate, butyl acetate, and such; polar solvents such as dimethylformamide, dimethyl sulfoxide, acetonitrile, acetone, and such; and preferred is dimethylformamide.

The reaction temperature is generally 0–100° C., and preferably 0–50° C. The reaction time is generally 15 minutes–24 hours, and preferably 1–12 hours.

Production method 2

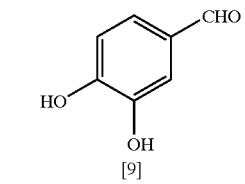
[9]

1st step $R^x\!-\!R^{6'}$
[10]

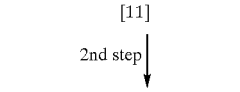
[11]

2nd step

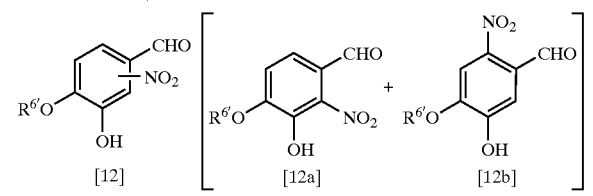
[12]     [12a]     [12b]

3rd step $R^x\!-\!R^{1'}$
[13]

-continued

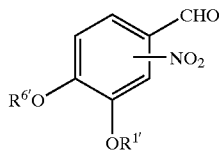
[14]

4th step

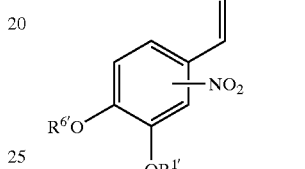
[15]

5th step $R^x\!-\!R^b$
[16]

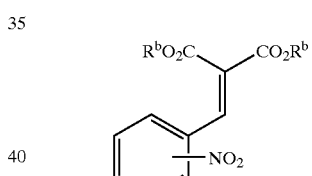
[17]

In this formula, $R^x$ represents halogen atom; each of $R^{1'}$ and $R^{6'}$ independently represents alkyl; and $R^b$ is as defined above.

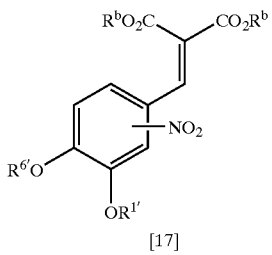
[17]

6th step

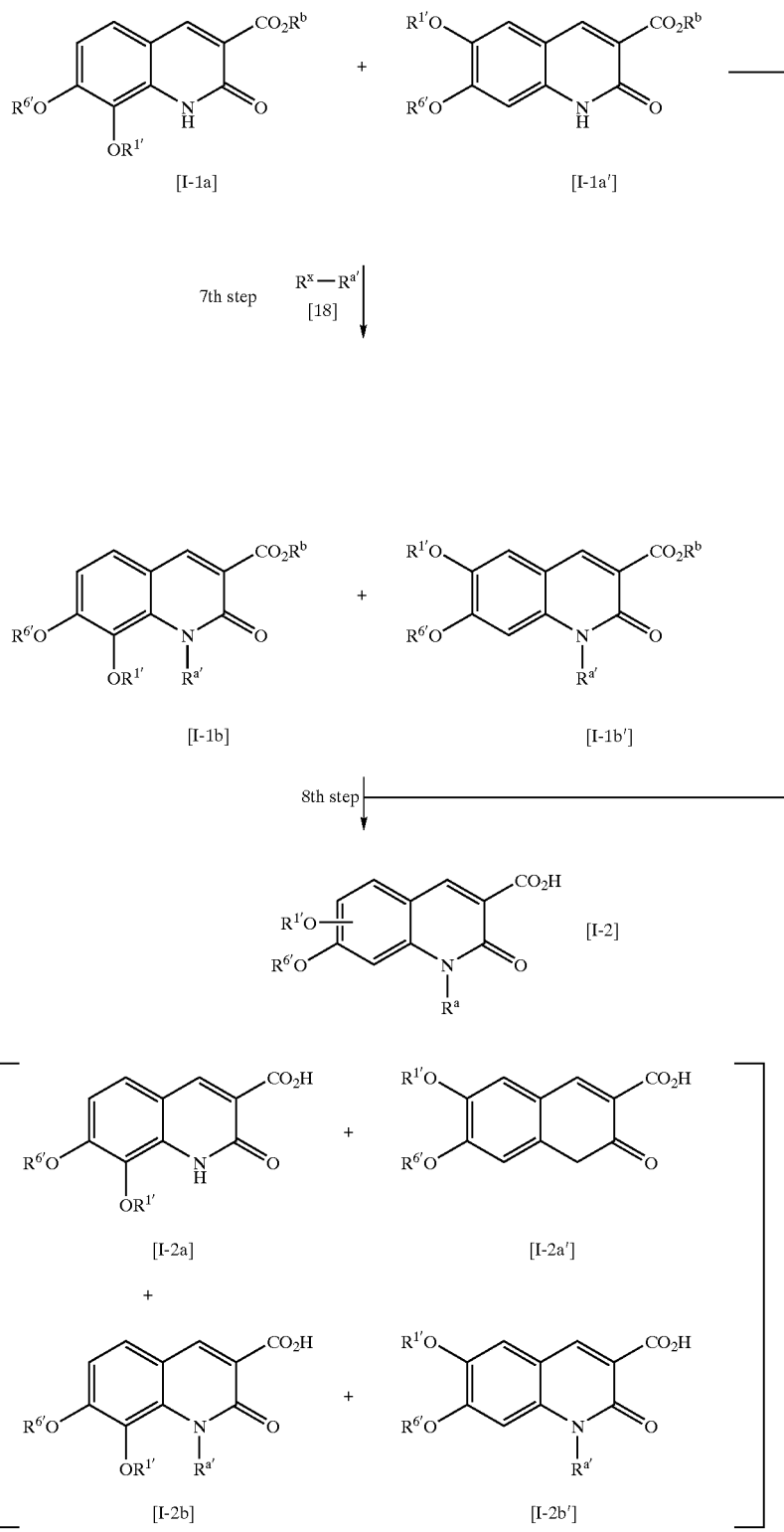
In this formula, $R^{a'}$ represents alkyl; $R^{1'}$, $R^{6'}$, $R^x$, $R^a$ and $R^b$ are as defined above.

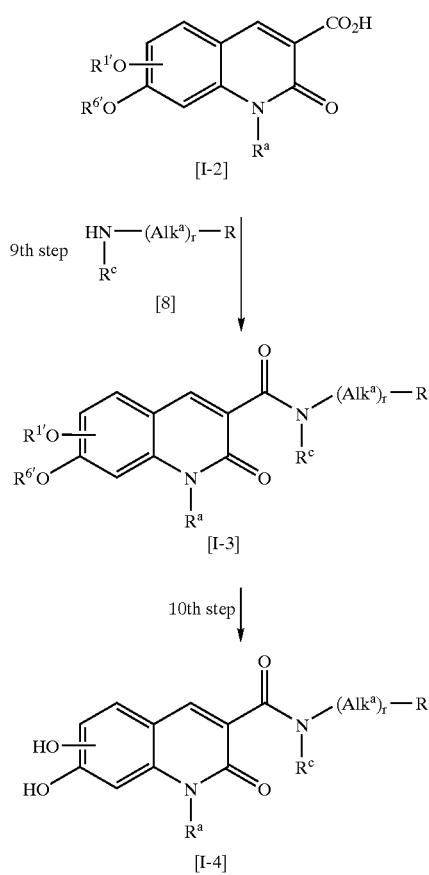

In this formula, $R^{1'''}$ represents alkyl; $R^{1'}$, $R^{6'}$, $R^x$, $R^a$, $R^c$, $Alk^a$, R and r are as defined above.

(Step 1)
Compound [9] (3,4-dihydroxybenzaldehyde) is allowed to react by using alkylating agent [10] in the presence of a base, thereby selectively alkylating the hydroxyl group located at the 4-position of the phenol of compound [9]. This results in the production of compound (11).

The alkylating agent to be used includes alkyl iodide such as methyl iodide, etc.; alkyl bromide such as methyl bromide, ethyl bromide, propyl bromide, butyl bromide, pentyl bromide, and such; alkyl chloride such as pentyl chloride, and such; dialkyl sulfate such as dimethyl sulfate, and such; and preferably used is alkyl bromide.

The base includes, for example, sodium carbonate, potassium carbonate, lithium carbonate, cesium carbonate, calcium carbonate, sodium bicarbonate, potassium bicarbonate, sodium hydroxide, potassium hydroxide, lithium hydroxide, sodium hydride, n-butyllithium, s-butyllithium, t-butyllithium, lithium diisopropylamide, and such; and preferably used is lithium carbonate.

The solvent includes, for example, hydrocarbon solvents such as benzene, toluene, xylene, hexane, and such; ether solvents such as diethyl ether, 1,2-dimethoxyethane, tetrahydrofuran, diglyme, and such; halogen solvents such as dichloromethane, chloroform, carbon tetrachloride, 1,2-dichloroethane, and such; ester solvents such as ethyl acetate, methyl acetate, butyl acetate, and such; polar solvents such as dimethylformamide, dimethyl sulfoxide, acetonitrile, acetone, and such; alcohol solvents such as methanol, ethanol, isopropyl alcohol, t-butanol, and such; and preferably used is dimethylformamide.

The reaction temperature is generally −20–100° C., and preferably 0–100° C. The reaction time is generally 15 minutes–48 hours, and preferably 1–6 hours.

(Step 2)
Compound [11] can be reacted with fuming nitric acid in the presence of concentrated sulfuric acid in a solvent, thereby mono-nitrating the ortho-position of formyl group of compound [11] to obtain compound [12] (where compound [12] refers to compound [12a], compound [12b] and a mixture thereof).

The solvent includes, for example, ether solvents such as diethyl ether, 1,2-dimethoxyethane, tetrahydrofuran, diglyme, etc.; halogen solvents such as dichloromethane, chloroform, carbon tetrachloride, 1,2-dichloroethane, and such; ester solvents such as ethyl acetate, methyl acetate, butyl acetate, and such; alcohol solvents such as methanol, ethanol, isopropyl alcohol, t-butanol, and such; acid solvents such as acetic acid, acetic anhydride, and such; preferably used is acetic acid.

The reaction temperature is generally −50–200° C., and preferably −10–60° C.

Alternatively, compound [12] can be obtained by nitrating compounds [11] by using lanthanum nitrate and sodium nitrate in the presence of an acid in a solvent in this step.

The acid includes, for example, benzoic acid, p-toluenesulfonic acid, acetic acid, methanesulfonic acid, hydrochloric acid, sulfuric acid, nitric acid, and such; and preferred is hydrochloric acid.

The solvent includes, for example, the above-mentioned solvents and preferred is tetrahydrofuran.

The reaction temperature is generally −50–200° C., and preferably 0–50° C.

(Step 3)
Compound [12] is allowed to react by using alkylating agent [13] in the presence of a base in a solvent, thereby alkylating the hydroxyl group located in the phenol of compound [12]. This results in the production of compound [14] (which means regioisomers and a mixture thereof corresponding to compound [12]).

The alkylating agent to be used includes the alkylating agents as described in Step 1 of Production method 2; and preferably used is alkyl bromide.

The base includes the bases as described in Step 1 of Production method 2; and preferably used is potassium carbonate.

The solvent includes the solvents as described in Step 1 of Production method 2; and preferably used is dimethylformamide.

The reaction temperature is generally −20–200° C., and preferably 0–100° C. The reaction time is generally 15 minutes–48 hours, and preferably 1–24 hr.

(Step 4)
Compound [14] is allowed to react to malonic acid in a solvent, thereby dehydration-condensing the formyl group moiety of compound [14]. This results in the production of compound [15] (which means regioisomers and a mixture thereof corresponding to compound [12]).

The solvent includes the solvents as described in Step 2 of Production method 2; and preferred is acetic acid.

The reaction temperature is generally −20–200° C., and preferably 0–100° C. The reaction time is generally 2–72 hours, but preferred is 3–24 hours.

(Step 5)
Compound [15] is esterified with alkylating agent [16] in the presence of a base in a solvent, thereby protecting the carboxyl group. This reaction results in the production of compound [17] (which means regioisomers and a mixture thereof corresponding to compound [15]).

The alkylating agent includes the alkylating agents as described in Step 1 of Production method 2; and preferred is methyl iodide.

The base includes the bases as described in Step 1 of Production method 2; and preferred is potassium carbonate.

The solvent includes the solvents as described in Step 1 of Production method 2; and preferred is dimethylformamide.

The reaction temperature is generally −20–200° C., and preferably 0–50° C. The reaction time is generally 15 minutes–48 hours, and preferably 1–24 hours.

(Step 6)

After the nitro group of compound [17] is reduced according to a commonly used method, the compound is condensed to construct the α-quinolone backbone. The reaction results in the production of compound [I-1a], compound [I-1a'], or a mixture thereof.

(Step 7)

Compound [I-1a], compound [I-1a'], or the mixture thereof, is alkylated by using alkylating agent [18] according to the same method as described in Step 3 of Production method 2. The reaction alkylates the NH portion of the quinolone moiety and this results in the production of the corresponding compound [I-1b], compound [I-1b'] or a mixture thereof.

(Step 8)

The esterified moiety of compound [I-1a], compound [I-1a'], compound [I-1b] or compound [I-1b'] is hydrolyzed according to a commonly used method to obtain the corresponding compound [I-2a], compound [I-2a'], compound [I-2b] and compound [I-2b'] (these four compounds are combined to be compound [I-2]).

(Step 9)

Compound [I-2], which has been converted to an activated carboxylic acid derivative, can be treated and amide-condensed with compound [8] in a solvent to give compound [I-3]

The activated carboxylic acid derivative includes, for example, acid halide that can be obtained by treating carboxylic acid with thionyl chloride, phosphorus oxychloride, phosphorus pentachloride, oxalyl chloride, and such; active ester that can be obtained by condensing carboxylic acid with 1-hydroxybenzotriazole, N-hydroxy succinimide or the like by using a condensing agent such as dicyclohexylcarbodiimide (DCC), 1-ethyl-3-(3-dimethylamino propyl) carbodiimide (EDC) hydrochloride, and such; mixed acid anhydride that can be obtained by reacting carboxylic acid with ethyl chlorocarbonate, pivaloyl chloride, isobutyl chlorocarbonate or the like; and preferably used is active ester obtained from N-hydroxybenzotriazole by using EDC hydrochloride as a condensing agent.

If required, it is also possible to use a base in combination in the above reaction. The base includes, for example, organic amines such as triethylamine, pyridine, and N-methylmorpholine; and preferred is triethylamine.

The solvent includes, for example, hydrocarbon solvents such as benzene, toluene, hexane, xylene, and such; ether solvents such as diethyl ether, 1,2-dimethoxyethane, tetrahydrofuran, diglyme, and such; halogen solvents such as dichloromethane, chloroform, carbon tetrachloxide, 1,2-dichloroethane, and such; ester solvents such as ethyl acetate, methyl acetate, butyl acetate, and such; polar solvents such as dimethylformamide, dimethyl sulfoxide, acetonitrile, acetone, etc.; and preferred is dimethylformamide. The reaction temperature is generally 0–100° C., and preferably 0–50° C. The reaction time is generally 15 minutes–24 hours, and preferably 1–12 hours.

(Step 10)

Compound [I-3] is treated with a Lewis acid in a solvent, thereby dealkylating the ether moiety. This reaction results in the production of compound [I-4].

The Lewis acid includes, for example, titanic tetrachloride, aluminum chloride, aluminum bromide, trimethylsilyl iodide, boron trichloride, boron tribromide, and such; and preferred is boron tribromide. Sulfur compound such as thiophenol, ethyl mercaptan, and such may be used in combination.

The solvent includes, for example, hydrocarbon solvents such as benzene, toluene, hexane, xylene, and such; ether solvents such as tetrahydrofuran, diglyme, and such; halogen solvents such as dichloromethane, chloroform, carbon tetrachloride, 1,2-dichloroethane, etc.; and preferred is dichloromethane.

The reaction temperature is generally −100–100° C., and preferably −80–0° C. The reaction time is generally 15 minutes–24 hours, but preferred is 30 minutes–5 hours.

In this production method, it is also possible to obtain compound [I-3] by condensing compound [I-2a], [I-2a'] or a mixture thereof with compound [8] in the same manner as described in Step 9 of Production method 2 and then alkylating the NH portion of quinolone backbone in the same manner as described in Step 7 of Production method 2.

Alternatively, it is also possible to obtain compound [I-3], for example, by skipping Step 3, treating compound [12] by using the procedure of Step 4 and later procedures for the ring formation of 7-substituted 8-hydroxy-2-oxoquinoline, then carrying out the procedure of Step 9 for amide-condensation, followed by alkylation by the method of Step 3. Thus, different combinations of the steps can be used for the production.

Production method 3

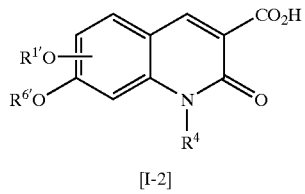

[I-2]

1st step

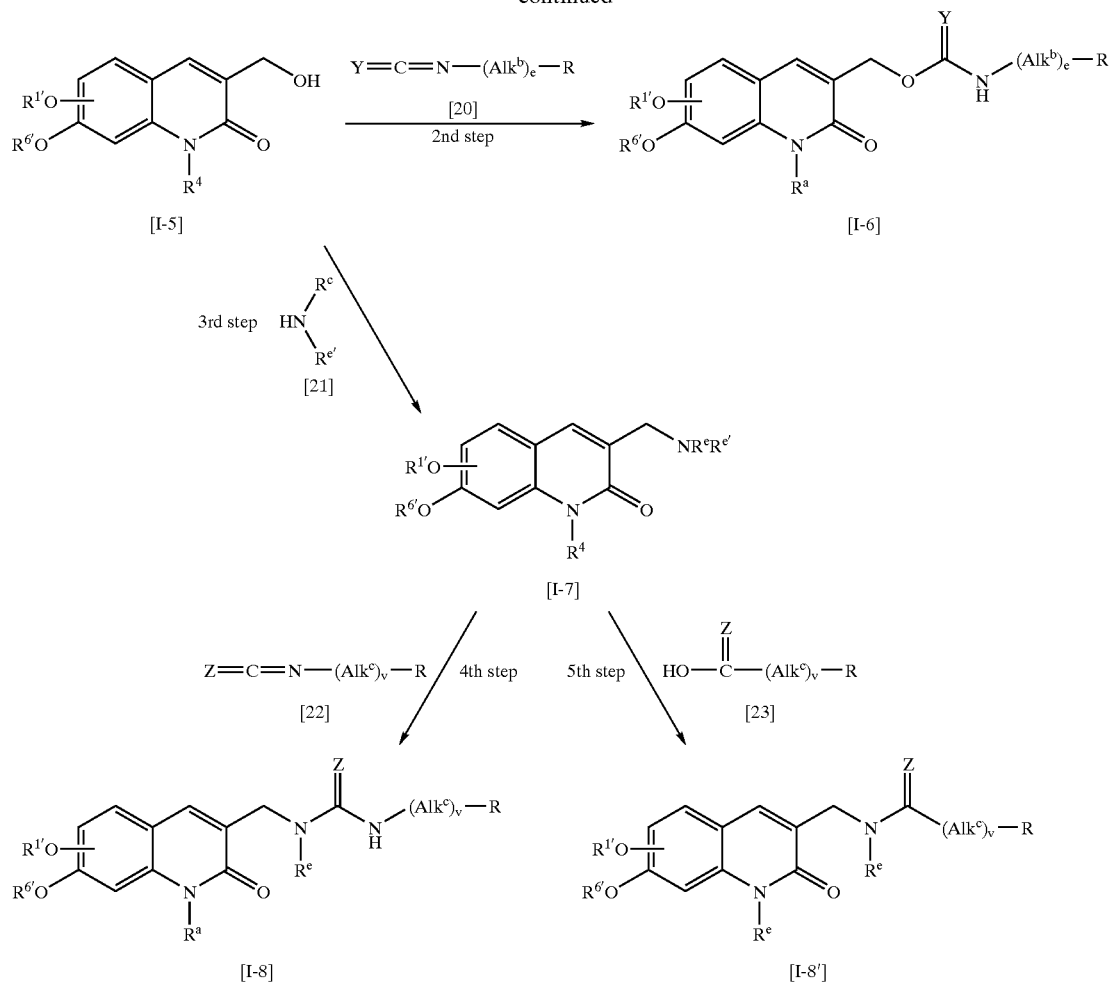

In this formula, each symbol is as described above.

(Step 1)

Compound [I-2], which is obtained by Production method 1 or Production method 2, is treated with a reducing agent in a solvent, thereby reducing the carboxyl group of compound [I-2]. Compound [I-5] is obtained by the reaction in this step.

The reducing agent includes common reducing reagents for carboxyl group, such as borane, etc., but it is preferable to use a method in which carboxylic acid is reduced after converted to an activated carbonyl derivative.

The activated carboxylic acid derivative includes, for example, mixed acid anhydride that can be obtained by reacting carboxylic acid to isopropyl chlorocarbonate, ethyl chlorocarbonate, pivaloyl chloride, isobutyl chlorocarbonate or the like; and preferred is an active ester obtained from isopropyl chlorocarbonate.

If required, it is also possible to use a base in combination in the above reaction. The base includes, for example, organic amines such as triethylamine, pyridine, and N-methylmorpholine; and preferred is triethylamine. Used for the reduction of activated carboxylic acid are sodium borohydride, lithium borohydride, and such; and preferred is lithium borohydride.

The solvent includes, for example, hydrocarbon solvents such as benzene, toluene, hexane, xylene, etc.; ether solvents such as diethyl ether, 1,2-dimethoxyethane, tetrahydrofuran, diglyme, and such; halogen solvents such as dichloromethane, chloroform, carbon tetrachloride, 1,2-dichloroethane, and such; and preferred is tetrahydrofuran.

In some cases in this reaction, base treatment should be carried out after reduction. The base being used in this reaction includes sodium hydroxide, potassium hydroxide, lithium hydroxide, potassium carbonate, sodium carbonate, and such; and preferred is sodium hydroxide. The reaction temperature is generally −20–100° C., and preferably −10–30° C. The reaction time is generally 15 minutes–24 hours, and preferably 1–12 hours.

(Step 2)

Compound [I-5] is treated with isocyanate or thioisocyanate compound [20] in the presence of a base in a solvent to give compound [I-6].

The isocyanate and thioisocyanate include, for example, aralkyl isocyanate such as benzylisocyanate, and such; and arylisocyanate such as phenyl isocyanate, 4-fluorophenyl isocyanate, pyridine-4-yl isocyanate, and such; and preferred is arylisocyanate.

The base includes, for example, organic amines such as triethylamine, pyridine, N-methylmorpholine, and such; and preferred is triethylamine.

The solvent includes the solvents as described in Step 1 of Production method 2; and preferred is chloroform.

The reaction temperature is generally −20–100° C., and preferably −10–30° C. The reaction time is generally 15 minutes–24 hours, and preferably 1–12 hours.

(Step 3)

Compound [I-5] is treated with acid chloride and then with amine compound [21] to give compound [I-7] in the presence of a base in a solvent.

The acid chloride includes methanesulfonyl chloride, p-toluenesulfonyl chloride, benzenesulfonyl chloride, and such; and preferred is methanesulfonyl chloride.

The base includes, for example, organic amines such as triethylamine, pyridine, N-methylmorpholine, and such; and preferred is triethylamine.

The solvent includes the solvents as described in Step 1 of Production method 2; and preferred is tetrahydrofuran.

The reaction temperature is generally −20–100° C., and preferably −10–30° C. The reaction time is generally 15 minutes–24 hours, and preferably 1–12 hours.

(Step 4)

When at least $R^{e'}$ is a hydrogen atom in compound [I-7], compound [I-7] can be subjected to a coupling reaction with isocyanate or thioisocyanate compound [22] in a solvent to give the corresponding compound [I-8].

The isocyanate and thioisocyanate include those described in Step 1 of Production method 3; and preferably used is arylisocyanate.

If required, it is also possible to use a base in combination in the above reaction. The base includes, for example, organic amines such as triethylamine, pyridine, and N-methylmorpholine; and preferred is triethylamine.

The solvent includes the solvents as described in Step 1 of Production method 2; and preferred is dimethylformamide.

The reaction temperature is generally 0–100° C., and preferably 0–50° C. The reaction time is generally 15 minutes–24 hours, and preferably 1–12 hours.

(Step 5)

When at least $R^{e'}$ is a hydrogen atom in compound [I-7], compound [I-7] can be subjected to a coupling reaction with an activated carboxylic acid derivative in a solvent to obtain compound [I-8'].

The carboxylic acid derivative to be used in the coupling reaction using an activated carboxylic acid derivative includes acid halide, active ester, mixed acid anhydride, etc. obtained from carboxylic acid [23] by the procedure as described in Step 9 of Production method 2; and preferred is an active ester obtained from N-hydroxybenzotriazole by using EDC hydrochloride as a condensing agent.

The solvent includes the solvents as described in Step 1 of Production method 2; and preferred is dimethylformamide.

The reaction temperature is generally 0–100° C., and preferably 0–50° C. The reaction time is generally 15 minutes–24 hours, and preferably is 1–12 hours.

Compound [I] produced in the above-mentioned manner can be separated and purified, for example, by known methods such as concentration, concentration under reduced pressure, extraction with solvent, crystallization, re-crystallization, chromatography and the like.

Further, pharmaceutically acceptable salts of compound [I] and also various isomers of compound [I] can be produced according to previously known methods.

Compound [I] and pharmaceutically acceptable salts thereof exhibit pharmaceutical effects on diseases known to be associated with cannabinoid receptors, particularly diseases associated with peripheral cell tissues (immune disease, various types of inflammation, allergic diseases, etc.) in mammals.

In other words, compound [I] and pharmaceutically acceptable sales thereof selectively act on cannabinoid receptors, particularly on peripheral cannabinoid receptors, and thus have excellent immunomodulating action, anti-inflammatory action and antiallergic action, but exert fewer side effects on the central nervous system.

Thus, compound [I] and pharmaceutically acceptable salts thereof are useful as modulators for cannabinoid receptors (particularly for peripheral cannabinoid receptors), immunomodulators, therapeutic agents for autoimmune diseases, anti-inflammatory agents and antiallergic agents.

When the compound [I] or their pharmaceutically acceptable salts are used as a pharmaceutical composition, they may be formulated into tablets, pills, powders, granules, suppositories, injections, eye drops, liquid, capsules, troaches, aerosols, elixirs, suspensions, emulsions, syrups, and so on by using a standard method, generally together with known pharmacologically acceptable carriers, excipients, diluents, extenders, disintegrators, stabilizers, preservatives, buffers, emulsifiers, aromatizers, colorants, edulcorants, viscosity increasing agents, flavors, solubilizers, or other additives such as water; plant oil; alcohols such as ethanol or benzyl alcohol, polyethylene glycol, glycerol triacetate, gelatin, lactose; or carbohydrates such as starch, magnesium stearate, talc, lanolin, vaseline, etc. The composition may be administered orally or parenterally.

The dose depends on the type and condition of disease, the type of compound to be administered and administration route, age, sex, and body weight of patient, etc. In general, compound [I] is daily given to an adult at a dose of 0.1–1000 mg, and preferably 1–300 mg, once or divided in the case of oral administration.

Further, the compounds of the present invention can be used as animal drugs.

BEST MODE FOR CARRYING OUT THE INVENTION

The present invention is illustrated more specifically by referring to the following Examples. However, the present invention is not limited thereto.

REFERENCE EXAMPLE 1

4-Methoxy-2-nitro-3-pentyloxybenzaldehyde

Isovanillin (200 g), acetic acid (700 ml), and concentrated sulfuric acid (0.2 ml) were mixed and the resultant suspension was cooled to 0° C., to which a solution of fuming nitric acid (57.2 ml) in acetic acid (200 ml) was added dropwise over a period of 30 minutes. The mixture was stirred for 40 minutes, and then water (400 ml) was added thereto and the crystals were collected through filtration to give a mixture of 3-hydroxy-4-methoxy-2-nitrobenzaldehyde and 3-hydroxy-4-methoxy-6-nitrobenzaldehyde (56.4 g).

The resultant mixture was mixed with dimethylformamide (700 ml), and potassium carbonate (136.7 g) and bromopentane (127.7 ml) were successively added to this solution. After being stirred at 100° C. for 4 hours, the reaction solution was filtered, and was separated with the addition of water (600 ml) and a mixture of hexane and ethyl acetate at a ratio of 1:1 (600 ml) The aqueous layer was extracted with a mixture of hexane and ethyl acetate at a ratio of 1:1 (600 ml), and the combined organic layer was dried over anhydrous magnesium sulfate, filtered to remove the desiccating agent, and concentrated under reduced pressure. The resultant crystals were collected through filtration. The filtrate was concentrated, and the resultant crystals were collected through filtration. This was repeated again, and the filtrate was concentrated to give 4-methoxy-2-nitro-3-pentyloxybenzaldehyde as a red oily substance (117 g). The filtered crystals were combined to give 4-methoxy-6-nitro-3-pentyloxybenzaldehyde as yellow crystals (90.1 g) (Table 1).

REFERENCE EXAMPLE 2

2-Amino-4-methoxy-3-pentyloxybenzaldehyde

4-Methoxy-2-nitro-3-pentyloxybenzaldehyde (2.213 g) obtained in Reference Example 1 was dissolved in ethanol (22 ml), and tin chloride dihydrate (9.34 g) was added thereto. After being heat-refluxed for 4 hours, the reaction solution was cooled with ice, and a saturated aqueous solution of sodium hydrogencarbonate was added to the solution to render it alkaline. Then the solution was extracted with ethyl acetate (50 ml), and the organic layer was dried over anhydrous sodium sulfate, filtered to remove the desiccating agent, and concentrated under reduced pressure. The resultant residue was purified through silica-gel column chromatography (eluent: a mixture of n-hexane and ethyl acetate at a ratio of 5;1) to obtain 2-amino-4-methoxy-3-pentyloxybenzaldehyde (1.675 g) (Table 1).

REFERENCE EXAMPLE 3

3-Hydroxy-4-methoxybenzaldehyde 3,4-Dihydroxybenzaldehyde (2.76 g, 20 mmol) was dissolved in DMF (15 ml), and methyl iodide (37.4 ml, 60 mmol) and anhydrous lithium carbonate (4.4 g, 60 mmol) were successively added to this solution. After being stirred at an external temperature of 90° C. for 1.5 hours, the reaction mixture was cooled to room temperature and the inorganic salt was filtered off. A saturated aqueous solution of ammonium chloride (200 ml) was added to the filtrate to adjust the aqueous layer to a pH of from 7 to 8, and the solution was extracted with ethyl acetate (300 ml×2). The combined organic layer was washed with a saturated aqueous solution of sodium chloride (300 ml), dried over anhydrous magnesium sulfate, filtered to remove the desiccating agent, and concentrated under reduced pressure to give the title compound (2.5 g, 82.2%) (Table 1).

REFERENCE EXAMPLE 4

3-Hydroxy-4-methoxy-2-nitrobenzaldehyde (4a)

3-Hydroxy-4-methoxy-6-nitrobenzaldehyde (4b)

3-Hydroxy-4-methoxybenzaldehyde (15.2 g, 0.1 mol) obtained in the same manner as in Reference Example 3 was dissolved in THF (150 ml), to which sodium nitrate (8.5 g, 0.1 mol) and lanthanum nitrate hexahydrate (8.7 g, 0.2 mol) were added, and then a mixture of concentrated hydrochloric acid and water at a ratio of 1:1 (70 ml) was added dropwise over a period of 20 minutes. The mixture was stirred for 40 minutes at room temperature, and the separated organic layer was successively washed with water (50 ml), a saturated aqueous solution of sodium hydrogencarbonate (50 ml), and a saturated aqueous solution of sodium chloride (100 ml), dried over anhydrous magnesium sulfate, filtered to remove the desiccating agent, and concentrated under reduced pressure to give a mixture of the title compounds 4a and 4b as pale red crystals (4a:4b=1:1, 13.3 g, yield 67.5%) (Table 2).

REFERENCE EXAMPLE 5

4-Methoxy-2-nitro-3-pentyloxybenzaldehyde (5a)

4-Methoxy-6-nitro-3-pentyloxybenzaldehyde (5b)

The mixture of 3-hydroxy-4-methoxy-2-nitrobenzaldehyde (4a) and 3-hydroxy-4-methoxy-6-nitrobenzaldehyde (4b) (4a:4b=1:1, 12.3 g, 62.4 mmol) obtained in Reference Example 4 was dissolved in DMF (20 ml), and bromopentane (11.3 g, 74.9 mmol) and anhydrous potassium carbonate (12.9 g, 93.6 mmol) were successively added to this solution. After being stirred at an external temperature of 90° C. for 1.5 hours, the reaction mixture was cooled to room temperature and the inorganic salt was filtered off. A saturated aqueous solution of ammonium chloride (200 ml) was added to the filtrate to adjust the aqueous layer to a pH of from 7 to 8, and the solution was extracted with ethyl acetate (300 ml×2). The combined organic layer was washed with a saturated aqueoussolution of sodium chloride (300 ml), dried over anhydrous magnesium sulfate, filtered to remove the desiccating agent, and concentrated under reduced pressure to give a crude mixture of the title compounds 5a and 5b (5a:5b =1:1, 17.12 g, quant.) (Tables 2 and 3). This crude product was used immediately in the subsequent reaction.

REFERENCE EXAMPLE 6

2-(4-Methoxy-2-nitro-3-pentyloxybenzylidene) malonic acid (6a)

2-(4-Methoxy-2-nitro-5-pentyloxybenzylidene) malonic acid (6b)

The crude product of 4-methoxy-2-nitro-3-pentyloxy-benzaldehyde (5a) and 4-methoxy-6-nitro-3-pentyloxybenzaldehyde (5b) (5a:5b=1:1, 17.12 g, 64.1 mmol) obtained in Reference Example 5 was dissolved in acetic acid (190 ml), to which malonic acid (20 g, 192 mmol) was added, and the mixture was stirred at an external temperature of 60° C. for 16 hours. After toluene (100 ml×2) was added to the reaction solution to remove acetic acid by azeotropic distillation, an aqueous solution of sodium hydroxide was added to the residue to adjust the aqueous solution to a pH of from 7 to 8, and the solution was washed with ethyl acetate (200 ml×2). The aqueous layer was acidified (pH=1 to 2) with concentrated hydrochloric acid, and was extracted with ethyl acetate (300 ml×2). The combined organic layer was washed with a saturated aqueous solution of sodium chloride (300 ml), dried over anhydrous magnesium sulfate, filtered to remove the desiccating agent, and concentrated under reduced pressure to give a crude mixture of the title compounds 6a and 6b (6a:6b=1:1, 23.3 g, overweight) (Table 3). This crude product was used immediately in the subsequent reaction.

REFERENCE EXAMPLE 7

Dimethyl 2-(4-methoxy-2-nitro-3-pentyloxybenzylidene)malonate (7a)

Dimethyl 2-(4-methoxy-2-nitro-5-pentyloxybenzylidene)malonate (7b)

The crude product of 2-(4-methoxy-2-nitro-3-pentyloxybenzylidene)malonic acid (6a) and 2-(4-methoxy-2-nitro-5-pentyloxy-benzylidene)malonic acid (6b) (6a:6b=1:1, 23.4 g, 64.1 mmol) obtained in Reference Example 6 was dissolved in DMF (160 ml), and methyl iodide (17.6 ml, 282 mmol) and anhydrous potassium carbonate (26.6 g, 192 mmol) were added to this solution. The mixture was stirred at room temperature for 1.5 hours, to which a saturated aqueous solution of ammonium chloride (800 ml) was added, and the solution was washed with ethyl acetate (300 ml×2). The combined organic layer was successively washed with water (300 ml) and a saturated aqueous solution of sodium chloride (300 ml), dried over anhydrous magnesium sulfate, filtered to remove the desiccating agent, and concentrated under reduced pressure to give a crude mixture of the title compounds 7a and 7b (7a:7b=1:1, 23.2 g, 94.8%) (Table 4). This crude product was used immediately in the subsequent reaction.

REFERENCE EXAMPLE 8

1-Methyl-4-bromo-1-t-butyldimethylsilyl ether

Step 1

2-Methyltetrahydrofuran (5.07 g, 41.7 mmol) was dissolved in trichloromethane (36 ml), and tetraethylammonium bromide (9.2 g, 43.8 mmol) was added thereto. Trifluoroborane etherate (5.56 ml, 43.8 mmol) was added dropwise to this solution at room temperature over a period of 10 minutes. After being stirred at room temperature for 16 hours, the reaction solution was cooled with ice, and a saturated aqueous solution of sodium hydrogencarbonate (40 ml) was added thereto to separate the organic layer. The aqueous layer was further extracted with trichloromethane (40 ml), and the combined organic layer was successively washed with water (40 ml) and a saturated aqueous solution of sodium chloride (40 ml), dried over anhydrous sodium sulfate, filtered to remove the desiccating agent, and concentrated under reduced pressure to give 1-methyl-4-bromo-1-butanol (5.07 g, 72.8%) as a pale yellow oily substance. This product was used immediately in the subsequent reaction.

DMSO-d6, 400 MHz; 4.4(bs, 1H), 3.5–3.7(m, 1H), 3.53 (t, 2H, J=6.8 Hz), 1.8–1.9(m, 2H), 1.3–1.5(m, 2H), 1.04(d, 3H, J=6.2 Hz).

Step 2

1-Methyl-4-bromo-1-butanol (5.07 g, 30.4 mmol) obtained in Step 1 was dissolved in dichloromethane (25 ml), and t-butyldimethylsilyl chloride (9.64 g, 36.5 mmol) and imidazole (4.89 g, 45.6 mmol) were successively added thereto while being cooled with ice. After being stirred at room temperature for 7 hours, the reaction solution was cooled again with ice, and a saturated aqueous solution of sodium hydrogencarbonate (50 ml) was added thereto to separate the organic layer. The organic layer was successively washed with water (50 ml) and a saturated aqueous solution of sodium chloride (50 ml), dried over anhydrous sodium sulfate, filtered to remove the desiccating agent, and concentrated under reduced pressure. The residue was purified through silica-gel column chromatography (eluent: a mixture of hexane and ethyl acetate at a ratio of 100:1) to obtain the title compound (6.35 g, 74.3%).

DMSO-d6,400 MHz: 3.8–3.9(m, 1H), 3.3–3.5(m, 2H), 1.8–2.0(m, 2H), 1.5–1.6(m, 2H), 1.13(d, 3H, J=6.1 Hz), 0.87(s, 9H), 0.04(s, 6H).

EXAMPLE 1-1

7-Methoxy-2-oxo-8-pentyloxy-1,2-dihydroquinoline-3-carboxylic acid methyl ester

2-Amino-4-methoxy-3-pentyloxybenzaldehyde (1.675 g) obtained in Reference Example 2 was dissolved in toluene (16 ml), to which dimethyl malonate (2.40 ml), piperidine (1.04 ml), and benzoic acid (80 ml) were added, and the mixture was stirred at an external temperature of 120° C. for 27 hours. After the reaction solution was cooled to room temperature, a saturated aqueous solution of sodium hydrogencarbonate (1600 ml) was added thereto to separate the organic layer, and the aqueous layer was extracted with toluene (30 ml). The combined organic layer was washed with a saturated aqueous solution of sodium chloride, dried over anhydrous sodium sulfate, filtered to remove the desiccating agent, and concentrated under reduced pressure. The residue was purified through silica-gel chromatography (eluent: a mixture of chloroform and ethyl acetate at a ratio of 1:1) to obtain the title compound (251 mg) (Table 5).

EXAMPLE 1-2 (Simultaneous synthesis with Example 1-1)

7-Methoxy-2-oxo-8-pentyloxy-1,2-dihydroquinoline-3-carboxylic acid methyl ester (Example 1-1)

7-Methoxy-2-oxo-6-pentyloxy-1,2-dihydroquinoline-3-carboxylic acid methyl ester (Example 1-2)

The crude product of dimethyl 2-[(4-methoxy-2-nitro-3-pentyl-oxyphenyl) methylene]propane-1,3-dioate (7a) and dimethyl 2-[(4-methoxy-2-nitro-5-pentyloxyphenyl) methylene]propane-1,3-dioate (7b) (7a:7b=1:1, 23.1 g, 60.6 mmol) obtained in Reference Example 7 was dissolved in acetic acid (260 ml) and water (17 ml), and the solution was heated at an external temperature of 60° C. To this reaction solution, reduced iron (27.1 g, 48.5 mmol) was gradually added with attention to effervescence, and the mixture was further stirred at an external temperature of 90° C. for 1.5 hours. After filtration, water (500 ml) was added to the filtrate, and the solution was extracted with ethyl acetate (300 ml×2). The combined organic layer was successively washed with a 1% hydrochloric acid aqueous solution (500 ml) and a saturated aqueous solution of sodium chloride (300 ml), dried over anhydrous magnesium sulfate, filtered to remove the desiccating agent, and concentrated under reduced pressure. The residue was purified through column chromatography (eluent: a mixture of n-hexane and ethyl acetate at a ratio of 1:1) to obtain the title compounds of Example 1-1 (8.56 g, 44.2%) and Example 1-2 (4.83 g, 25.0%) as pale yellow crystals (Table 5). A crude product of 7a and 7b (7a:7b=1:1, 23.2 g, 94.8%) was also obtained.

EXAMPLE 1-3

1-Methyl-7-methoxy-2-oxo-8-pentyloxy-1,2-dihydroquinoline-3-carboxylic acid methyl ester 7-Methoxy-2-oxo-8-pentyloxy-1,2-dihydroquinoline-3-carboxylic acid methyl ester (1.02 g, 3.2 mmol) obtained in the same manner as in Example 1-1 was dissolved in DMF (10 ml), and methyl iodide (0.4 ml, 6.4 mmol) and anhydrous potassium carbonate (0.89 g, 6.4 mmol) were added to this solution. After the mixture was stirred at an external temperature of 60° C. for 1.5 hours, a saturated aqueous solution of ammonium chloride (80 ml) was added thereto to adjust the solution to a pH of 8, and the solution was washed with ethyl acetate (50 ml×2). The combined organic layer was successively washed with a saturated aqueous solution of sodium chloride (50 ml), dried over anhydrous magnesium sulfate, filtered to remove the desiccating agent, and concentrated under reduced pressure. The residue was purified through silica-gel chromatography (eluent: a mixture of chloroform and ethyl acetate at a ratio of 10:1) to obtain the title compound (532 mg, 49.91) (Table 5).

A compound shown in Example 1-4 was obtained in the same manner as in Reference Examples and Example 1-3 above. Chemical structure and properties of the compound are shown in Table 6.

EXAMPLE 2-1

7-Methoxy-2-oxo-8-pentyloxy-1,2-dihydroquinoline-3-carboxylic acid

7-Methoxy-2-oxo-8-pentyloxy-1,2-dihydroquinoline-3-carboxylic acid methyl ester (240 mg) obtained in Example 1-1 was dissolved in methanol (7 ml) and water (3 ml), to which sodium hydroxide (120 ml) was added, and the solution was stirred at room temperature for 1.5 hours. While the reaction vessel was cooled with ice, the solution was acidified with the addition of concentrated hydrochloric acid, and extracted with ethyl acetate (20 ml). The organic layer was dried over anhydrous sodium sulfate, filtered to remove the desiccating agent, and concentrated under reduced pressure to give the title compound (228 ml) (Table 6).

Compounds shown in Examples 2-2 to 2-7 were obtained in the same manner as in Reference Examples and Example 2-1 above. Chemical structures and properties of the compounds are shown in Tables 6 to 8.

EXAMPLE 3-1

7-Methoxy-2-oxo-8-pentyloxy-1,2-dihydroquinoline-3-carboxylic acid (2-pyridine-4-ylethyl)amide 7-Methoxy-2-oxo-8-pentyloxy-1,2-dihydroquinoline-3-carboxylic acid (30.0 mg) obtained in Example 2-1, 2-pyridine-4-ylethylamine (36.0 mg), and 1-hydroxybenzotriazole hydrate (17.3 mg) were dissolved in dimethylformamide (2 ml), and 1-ethyl-3-(3-dimethyl-aminopropyl)carbodiimide hydrochloride (24.5 mg) was successively added to this solution while being cooled with ice. After the reaction solution was stirred at room temperature for 5 hours, ethyl acetate (3 ml) and a saturated aqueous solution of sodium hydrogencarbonate (3 ml) were added to this solution. The organic layer was separated and dried over anhydrous sodium sulfate, filtered to remove the desiccating agent, and concentrated under reduced pressure. The resultant residue was purified through column chromatography (eluent: a mixture of chloroform and methanol at a ratio of 25:1) to obtain the title compound (35 mg) as colorless crystals (Table 8).

Compounds shown in Examples 3-2 to 3-4 were obtained in the same manner as in Example 3-1 above. Chemical structures and properties of the compounds are shown in Table 9.

EXAMPLE 3-5

7-Methoxy-2-oxo-8-pentyloxy-1,2-dihydroquinoline-3-carboxylic acid (3,4-methylenedioxybenzyl)amide 7-Methoxy-2-oxo-8-pentyloxy-1,2-dihydroquinoline-3-carboxylic acid (50 mg, 0.164 mmol) obtained in the same manner as in Example 2-1 was dissolved in dichloromethane (1 ml), and DMF (cat.) was added thereto, followed by thionyl chloride (0.018 ml, 0.24 mmol), and then the solution was stirred at room temperature for 1.0 hour. Toluene (4 ml×2) was added to the reaction solution to remove the excess acid and thionyl chloride by evaporation, and an acid chloride was obtained as pale yellow crystals. The crystals were dissolved in dichloromethane (1 ml). and the solution was added dropwise to a solution of 3,4-methylenedioxybenzylamine (0.08 ml, 0.655 mmol) in dichloromethane (1 ml) prepared separately, and then the reaction solution was stirred at room temperature for 2 hours. The reaction solution was concentrated, and the residue was purified through column chromatography (eluent; a mixture of chloroform and ethyl acetate at a ratio of 10:1) to obtain the title compound (47 mg, 65.4%) (Table 10).

Compounds shown in Examples 3-6 to 3-54, and 3-60 were obtained in the same manner as in Reference Examples and Examples 3-1 and 3-5 above. Chemical structures and properties of the compounds are shown in Tables 10 to 26, and 28.

EXAMPLE 3-55

8-(4-Hydroxypentyloxy)-7-methoxy-2-oxo-1,2-dihydroquinoline-3-carboxylic acid (3,4-methylenedioxybenzyl)amide In the usual manner, 8-hydroxy-7-methoxy-2-oxo-1,2-dihydro-quinoline-3-carboxylic acid (3,4-methylenedioxybenzyl)amide (503 mg; Example 3-47) was alkylated with 1-methyl-4-bromo-1-t-butyl-dimethylsilyl ether obtained in Reference Example 8, and then t-butyldimethylsilyl group was removed to give the title compound (493 mg) (Table 26).

Compounds shown in Examples 3-56 to 3-59 were obtained in the same manner as in Example 3-55 above. Chemical structures and properties of the compounds are shown in Tables 27 and 28.

EXAMPLE 4-1

7,8-Dihydroxy-2-oxo-1,2-dihydroquinoline-3-carboxylic acid [2-(4-fluorophenyl)ethyl]amide 7-Methoxy-2-oxo-8-pentyloxy-1,2-dihydroquinoline-3-carboxylic acid [2-(4-fluorophenyl)ethyl]amide (340 mg, 0.80 mmol) obtained in the same manner as in Example 3-5 was dissolved in dichloromethane (4 ml), and boron tribromide (1.0 M solution in dichloromethane; 2.4 ml, 2.4 mmol) was added dropwise thereto at an internal temperature of −60° C. under a nitrogen stream. The solution was allowed to warm to room temperature, and was stirred for 0.5 hour. The reaction solution was poured into ice water (40 ml) to precipitate crystals. These crystals were collected through filtration, washed with water (10 ml), and dried under reduced pressure to give the title compound (247.5 mg, 90.7%) (Table 29).

EXAMPLE 5-1

8-Butoxy-3-hydroxymethyl-7-methoxy-2-oxo-1,2-dihydroquionoline

8-Butoxy-7-methoxy-2-oxo-1,2-dihydroquinoline-3-carboxylic acid (1.46 g, 5.00 mmol) obtained in the same manner as in Example 2-1 was dissolved in THF (20 ml), and triethylamine (1,53 ml, 11.0 mmol) and isopropyl chlorocarbonate (1.35 g, 11.0 mmol) were successively added thereto while being cooled with ice. After the solution was stirred at the same temperature for 15 minutes, an aqueous solution of sodium borohydride (2.08 g, 55.0 mmol, 20 ml) was added thereto while being cooled with ice, and the solution was further stirred at the same temperature for 1 hour. A 50% sodium hydroxide aqueous solution (20 ml) was added to the solution, which was then stirred at room temperature for 1 hour, and water (50 ml) and chloroform (50 ml) were added thereto to separate the organic layer. The aqueous layer was further extracted with chloroform (30 ml), and the combined organic layer was dried over magnesium sulfate, filtered to remove the desiccating agent, and concentrated under reduced pressure. The resultant residue was purified through column chromatography (eluent: a mixture of hexane and ethyl acetate at a ratio of 1:3) to obtain the title compound (1.28 g, yield 92%) as colorless crystals (Table 29).

A compound shown in Example 5-2 was obtained in the same manner as in Example 5-1 above. Chemical structure and properties of the compound are shown in Table 29.

EXAMPLE 6-1

N-(4-Fluorophenyl)carbamic acid (8-butoxy-7-methoxy-2-oxo-1,2-dihydroquinolin-3-yl)methyl ester 8-Butoxy-3-hydroxymethyl-7-methoxy-2-oxo-1,2-dihydroquionoline (100 mg, 0.361 mmol) obtained in the same manner as in Example 5-1 was dissolved in chloroform (1 ml), and triethylamine (10 μl) and 4-fluorophenyl isocyanate (45 μl, 0.396 mmol) were successively added thereto while being cooled with ice. The mixture was stirred at the same temperature for 5 hours, to which methanol (100 μl) was added, and concentrated under reduced pressure. The resultant residue was dissolved in THF, silica gel was slurried with the resultant solution, and the solution was purified through column chromatography (eluent: a mixture of hexane and ethyl acetate at a ratio of 1:3) to obtain the title compound (128 mg, yield 86%) as colorless crystals (Table 30).

EXAMPLE 6-2

N-Pyridine-4-ylcarbamic acid (8-ethoxy-7-methoxy-2-oxo-1,2-dihydroquinolin-3-yl)methyl ester 8-Ethoxy-3-hydroxymethyl-7-methoxy-2-oxo-1,2-dihydroquionoline (100 mg, 0.4 mmol) obtained in the same manner as in Example 5-1 was suspended in methylene chloride (1.5 ml), and pyridine (39 μl, 0.48 mmol) and 4-nitrophenylchloroformate (97 mg, 0.48 mmol) were added thereto while being cooled with ice. The mixture was stirred at the same temperature for 1 hour. After completion of the reaction, dimethylformamide (1.5 ml) was added, and then triethylamine (280 μl, 2.0 mmol) and 4-aminopyridine (188 mg, 2.0 mmol) were added to the reaction mixture while being cooled with ice, and the mixture was stirred at room temperature for 15 hours. After completion of the reaction, chloroform (15 ml) and a saturated aqueous solution of sodium bicarbonate (15 ml) were added to the mixture for separation. The organic layer was dried over anhydrous sodium sulfate, filtered to remove the desiccating agent, and concentrated. The resultant residue was purified through preparative thin layer chromatography (developing eluent: a mixture of chloroform and methanol at a ratio of 90:10) to obtain the title compound (56 mg, yield 38%) as pale yellow crystals (Table 30).

EXAMPLE 7-1

3-Dimethylaminomethyl-8-ethoxy-7-methoxy2-oxo-1,2-dihydro-quinoline

8-Ethoxy-3-hydroxymethyl-7-methoxy-2-oxo-1,2-dihydroquinoline (200 mg, 0.80 mmol) obtained in the same manner as in Example 5-1 was dissolved in THF (5 ml), and triethylamine (134 μl, 0.96 mmol) and methanesulfonyl chloride (68 μl, 0.88 mmol) were successively added thereto while being cooled with ice. The mixture was stirred at the same temperature for 30 minutes, to which 40% aqueous solution of dimethylamine (7.0 ml) was added at a time, and was further stirred at room temperature for one hour. Water (20 ml) and chloroform (20 ml) were added to the reaction solution, and the organic layer was separated. The aqueous layer was further extracted with chloroform (10 ml), and the combined organic layer was concentrated. The resultant residue was dissolved in 1 N hydrochloric acid (5 ml), and the solution was washed three times with ethyl acetate (5 ml×3). The aqueous layer was neutralized with a saturated aqueous solution of sodium bicarbonate, and was extracted two times with chloroform (5 ml×2). The combined organic layer was dried over magnesium sulfate and concentrated under reduced pressure, and the resultant residue was washed with hexane to give the title compound (128 mg, yield 58%) as colorless crystals (Table 30).

EXAMPLE 7-2

8-Butoxy-3-aminomethyl-7-methoxy-2-oxo-1,2-dihydroquinoline

8-Butoxy-3-hydroxymethyl-7-methoxy-2-oxo-1,2-dihydroquinoline (431 mg, 1.55 mmol) obtained in the same manner as in Example 5-1 was dissolved in THF (10 ml), and triethylamine (260 μl, 1.87 mmol) and methanesulfonyl chloride (132 μl, 1.71 mmol) were successively added thereto while being cooled with ice. The mixture was stirred at the same temperature for 20 minutes, to which 28% aqueous ammonia (20 ml) was added at a time, and was further stirred at room temperature for 1 hour. Water (20 ml) and chloroform (20 ml) were added to the reaction solution, and the organic layer was separated. The aqueous layer was further extracted with chloroform (10 ml), and the combined organic layer was dried over magnesium sulfate, filtered to remove the desiccating agent, and concentrated under reduced pressure. The resultant residue was purified through column chromatography (eluent: a mixture of chloroform, methanol and aqueous ammonia at a ratio of 90:10:1) to obtain the title compound (146 mg, 34%) as colorless crystals (Table 31).

A compound shown in Example 7-3 was obtained in the same manner as in Example 7-1 or 7-2 above. Chemical structure and properties of the compound are shown in Table 31.

EXAMPLE 8-1

N-[(8-Butoxy-7-methoxy-2-oxo-1,2-dihydroquinoline-3-yl)-methyl]-N'-(4-fluorophenyl) urea 8-Butoxy-3-aminomethyl-7-methoxy-2-oxo-1,2-dihydroquinoline (56.6 mg, 0.205 mmol) obtained in Example 7-2 was dissolved in chloroform (1 ml), and 4-fluorophenyl isocyanate (25.6 μl, 0.225 mmol) was successively added thereto while being cooled with ice. The mixture was stirred at the same temperature for 30 minutes, to which methanol (30 μl) and triethylamine (30 μl) were added, and was further stirred for 30 minutes. The reaction solution was concentrated under reduced pressure, and the resultant residue was washed with toluene to give the title compound (73 mg, yield 86%) as colorless crystals (Table 31).

EXAMPLE 8-2

N-[(8-Butoxy-7-methoxy-2-oxo-1,2-dihydroquinoline-3-yl)-methyl]-(4-hydroxyphenyl) acetamide 8-Butoxy-3-aminomethyl-7-methoxy-2-oxo-1,2-dihydroquinoline (77.7 mg, 0.281 mmol) obtained in Example 7-2, 4-hydroxyphenylacetic acid (47.0 mg, 0.309 mmol) and N-hydroxybenzotriazole (41.8 mg, 0.309 mmol) were dissolved in DMF (3 ml), and EDC (59.2 mg, 0.309 mmol) and triethylamine (30 μl) were successively added thereto. The mixture was stirred at 50° C. for 3 hours, and then a saturated aqueous solution of sodium bicarbonate (3 ml) and toluene (5 ml) were added thereto. The precipitated crystals were collected through filtration, and washed successively with water, 1 N hydrochloric acid, water, and ethyl acetate to give the title compound (88 mg, yield 76%) as colorless crystals (Table 32).

TABLE 1

| Ref. Ex. No. | structure/character/mp (° C.) | 1H NMR (δ) ppm | IR cm$^{-1}$ MS |
|---|---|---|---|
| 1 | 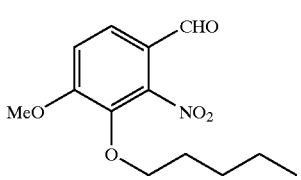 | CDCl3, 300MHz<br>9.80(1H, s)<br>7.64(1H, d, J=8.6Hz)<br>7.09(1H, d, J=8.6Hz)<br>4.11(2H, t, J=6.6Hz)<br>3.99(3H, s)<br>1.60–1.80(2H, m)<br>1.28–1.47(4H, m)<br>0.92(3H, t, J=7.1Hz) | FAB+<br>268[M + H +]<br>(80)<br>198 (100) |
| 2 | 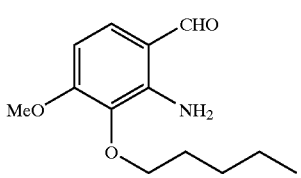 | CDCl3, 300MHz<br>9.52(1H, s)<br>7.22(1H, d, J=9.0Hz)<br>6.90(1H, d, J=9.0Hz)<br>4.41(2H, t, J=6.9Hz)<br>3.97(3H, s)<br>2.0–2.3(2H, bs)<br>1.7–1.9(2H, m)<br>1.3–1.5(4H, m)<br>0.92(3H, t, J=7.2Hz) | FAB+<br>238[M + H +]<br>(100) |
| 3 | 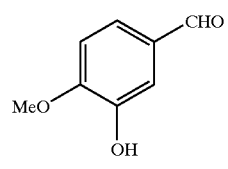<br>Pale yellow crystal/113–114 | CDCl3, 300MHz<br>9.84(s, 1H)<br>7.45(s, 1H)<br>7.43(d, 1H, J=8.7Hz)<br>6.98(d, 1H, J=8.7Hz)<br>6.40(bs, 1H)<br>4.00(s, 3H) | FAB+<br>153[M + H +]<br>(100) |

TABLE 2

| Ref. Ex. No. | structure/character/mp (° C.) | 1H NMR (δ) ppm | IR cm$^{-1}$ MS |
|---|---|---|---|
| 4a | 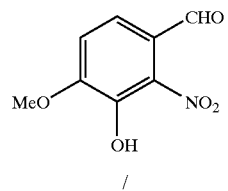 | DMSO-d6, 300MHz<br>10.91(bs, 1H)<br>9.57(s, 1H)<br>7.59(d, 1H, J=8.4Hz)<br>7.35(d, 1H, J=8.4Hz)<br>3.99(3H, s) | FAB−<br>232[M + H +]<br>(20)<br>185(100) |
| 4b | 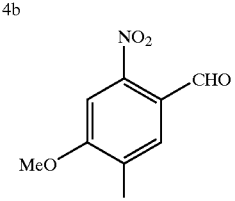 | DMSO-d6, 300MHz<br>10.91(bs, 1H)<br>10.18(s, 1H)<br>7.83(s, 1H)<br>7.22(s, 1H)<br>3.96(3H, s) | FAB−<br>232[M + H +]<br>(20)<br>185(100) |

TABLE 2-continued

| Ref. Ex. No./structure/character/mp (° C.) | 1H NMR (δ) ppm | IR cm$^{-1}$ MS |
|---|---|---|
| 5a 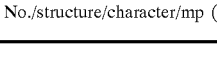 / | CDCl3, 300MHz<br>9.79(s, 1H)<br>7.64(d, 1H, J=8.6Hz)<br>7.06(d, 1H, J=8.6Hz)<br>4.09(t, 2H, J=6.7Hz)<br>4.00(s, 3H)<br>1.7–1.8(m, 2H)<br>1.3–1.5(m, 4H)<br>0.92(t, 3H, J=7.1Hz) | |

TABLE 3

| Ref. Ex. No./structure/character/mp (° C.) | 1H NMR (δ) ppm | IR cm$^{-1}$ MS |
|---|---|---|
| 5b 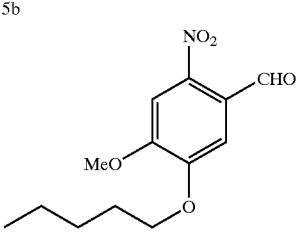 / | CDCl3, 300MHz<br>10.43(s, 1H)<br>7.61(s, 1H),<br>7.39(s, 1H)<br>4.16(t, 2H, J=6.7Hz)<br>4.16(s, 3H)<br>1.8–2.0(m, 2H)<br>1.3–1.5(m, 4H)<br>0.94(t, 3H, J=6.9Hz) | |
| 6a 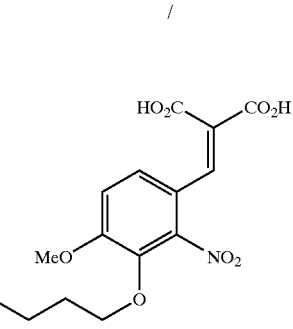 / | CDCl3, 300MHz<br>9.50(bs, 2H)<br>7.81(s, 1H)<br>7.38(d, 1H, J=8.4Hz)<br>7.00(d, 1H, J=8.4Hz)<br>4.05(t, 2H, J=6.9Hz)<br>3.93(s, 3H)<br>1.6–1.9(m, 2H)<br>1.3–1.5(m, 4H)<br>0.91(t, 3H, J=6.9Hz) | FAB+<br>354[M + H +]<br>(100) |
| 6b 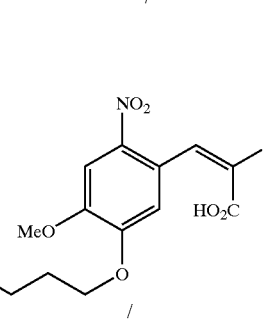 / | CDCl3, 300MHz<br>9.50(bs, 2H)<br>8.67(s, 1H)<br>7.76(s, 1H)<br>6.82(s, 1H)<br>4.10(t, 2H, J=6.9Hz)<br>3.97(s, 3H)<br>1.8–2.0(m, 2H)<br>1.3–1.5(m, 4H)<br>0.91(t, 3H, J=6.9Hz) | FAB+<br>354[M + H +]<br>(100) |

TABLE 4

| Ref. Ex. No./structure/character/mp (° C.) | 1H NMR (δ) ppm | IR cm⁻¹ | MS |
|---|---|---|---|
| 7a 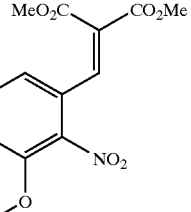 Pale blown crystal / | CDCl3, 300MHz<br>7.53(s, 1H)<br>7.19(d, 1H, J=8.8Hz)<br>6.97(d, 1H, J=8.8Hz)<br>4.04(t, 2H, J=6.8Hz)<br>3.93(s, 3H)<br>3.83(s, 3H)<br>3.79(s, 3H)<br>1.7–1.8(m, 2H)<br>1.3–1.5(m, 4H)<br>0.92(t, 3H, J=7.0Hz) | | FAB+<br>382[M – H +]<br>(100) |
| 7b 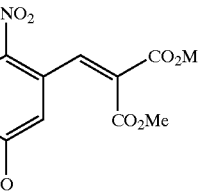 Pale blown crystal / | CDCl3, 300MHz<br>8.22(s, 1H)<br>7.76(s, 1H)<br>6.85(s, 1H)<br>4.11(t, 2H, J=6.7Hz)<br>3.97(s, 3H)<br>3.88(s, 3H)<br>3.66(s, 3H)<br>1.8–2.0(m, 2H)<br>1.3–1.5(m, 4H)<br>0.94(t, 3H, J=6.8Hz) | | FAB+<br>382[M – H +]<br>(100) |

TABLE 5

| Ex. No./structure/character/mp (° C.) | 1H NMR (δ) ppm | IR cm⁻¹ | MS |
|---|---|---|---|
| 1-1 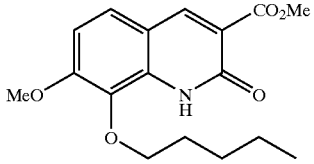 Colorless crystal / 130–131 | CDCl3, 300MHz<br>9.04(1H, bs)<br>8.50(1H, s)<br>7.36(1H, d, J=9.0Hz)<br>6.88(1H, d, J=9.0Hz)<br>4.13(2H, t, J=6.9Hz)<br>3.96(3H, s)<br>3.74(3H, s)<br>1.7–1.9(2H, m)<br>1.3–1.5(4H, m)<br>0.94(3H, t, J=7.2Hz) | KBr<br>3423<br>2952<br>1742<br>1642<br>1505<br>1269 | FAB+<br>320(M + H +)<br>(100)<br>288(70) |
| 1-2 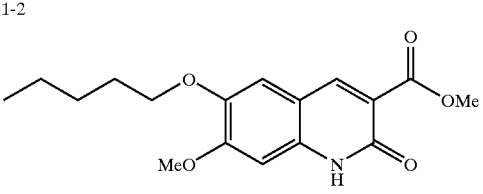 Colorless crystal / 194–195 | CDCl3, 300MHz<br>12.6(s, 1H)<br>8.54(s, 1H)<br>6.98(s, 1H)<br>6.95(s, 1H)<br>4.04(t, 2H, J=6.9Hz)<br>4.04(s, 3H)<br>3.70(s, 3H)<br>1.8–2.0(m, 2H)<br>1.3–1.6(m, 4H)<br>0.95(t, 3H, J=6.9Hz) | KBr<br>3444<br>2953<br>1730<br>1645<br>1571<br>1511<br>1484<br>1421<br>1269<br>1228<br>1900 | FAB+<br>320(M + H +)<br>(100)<br>288(100) |
| 1-3 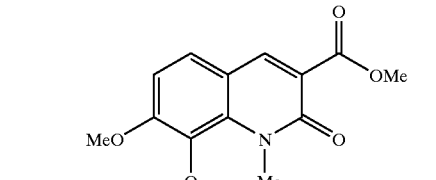 Pale blown crystal / 102–103 | CDCl3, 300MHz<br>8.33(s, 1H)<br>7.36(d, 1H, J=8.7Hz)<br>6.92(d, 1H, J=8.7Hz)<br>3.98(s, 3H)<br>3.97(s, 3H)<br>3.94(s, 3H)<br>3.85(t, 2H, 6.8Hz)<br>1.7–1.9(m, 2H)<br>1.3–1.5(m, 4H)<br>0.93(t, 3H, J=6.9Hz) | KBr<br>2938<br>1703<br>1659<br>1613<br>1590<br>1500<br>1453<br>1274<br>1059<br>800 | FAB+<br>334[M – H +]<br>(100) |

TABLE 6

| Ex. No./structure/character/mp (° C.) | 1H NMR (δ) ppm | IR cm$^{-1}$ | MS |
|---|---|---|---|
| 1-4 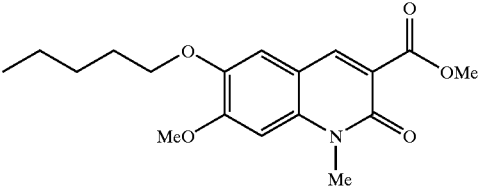<br>Colorless crystal / 124–125 | DMSO-d6, 300MHz<br>8.42(s, 1H)<br>7.44(s, 1H)<br>6.97(s, 1H)<br>3.98(t, 2H, J=6.6Hz)<br>3.97(s, 3H)<br>3.78(s, 3H)<br>3.65(s, 3H)<br>1.7–1.9(m, 2H)<br>1.3–1.5(m, 4H)<br>0.90(t, 3H, J=6.8Hz) | KBr<br>2948<br>1736<br>1260<br>1080<br>795 | FAB+<br>334(M + H +)<br>(100)<br>302(100) |
| 2-1 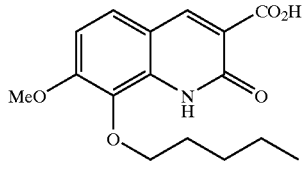<br>Pale yellow crystal / 178–179 | CDCl3, 300MHz<br>14.00(1H, s)<br>9.42(1H, bs)<br>8.87(1H, s)<br>7.51(1H, d, J=9.0Hz)<br>7.03(1H, d, J=9.0Hz)<br>4.18(2H, t, J=6.9Hz)<br>4.01(3H, s)<br>1.7–1.8(2H, m)<br>1.3–1.5(4H, m)<br>0.95(3H, t, J=6.9Hz) | KBr<br>3423<br>2952<br>1742<br>1642<br>1505<br>1269 | FAB+<br>306[M + H +]<br>(100) |
| 2-2 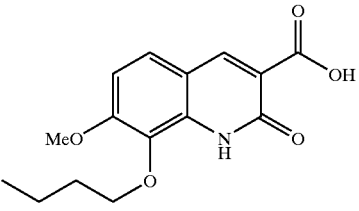<br>Colorless crystal / 182–184 | CDCl3, 300MHz<br>14.98(br s, 1H)<br>9.51(br s, 1H)<br>8.87(s, 1H)<br>7.51(d, J=9.0Hz, 1H)<br>7.04(d, J=9.0Hz, 1H)<br>4.20(t, J=6.9Hz, 2H)<br>4.02(s, 3H)<br>1.81(m, 2H)<br>1.51(m, 2H)<br>1.00(t, J=6.9Hz, 3H) | KBr<br>1723<br>1630<br>1506<br>1283<br>1258<br>1099 | |

TABLE 7

| Ex. No./structure/character/mp (° C.) | 1H NMR (δ) ppm | IR cm$^{-1}$ | MS |
|---|---|---|---|
| 2-3 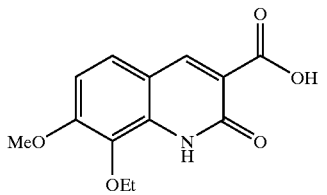<br>Colorless crystal / 242–244 | CDCl3, 300MHz<br>14.00(br s, 1H)<br>9.71(br s, 1H)<br>8.88(s, 1H)<br>7.52(d, J=9.0Hz, 1H)<br>7.04(d, J=9.0Hz, 1H)<br>4.29(q, J=6.9Hz, 2H)<br>4.02(s, 3H)<br>1.44(t, J=6.9Hz, 3H) | KBr<br>1736<br>1634<br>1504<br>1474<br>1282<br>1259<br>1095 | |
| 2-4 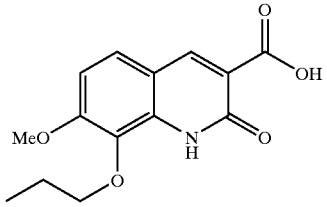<br>Colorless crystal / 178–181 | DMSO-d6, 300MHz<br>12.37(brs, 1H)<br>8.90(s, 1H)<br>7.81(d, 1H, J=9.2Hz)<br>7.27(d, 1H, J=9.2Hz)<br>3.97(m, 5H)<br>1.80(q, 2H, J=7.3Hz)<br>0.95(t, 3H, J=7.6Hz) | KBr<br>3188<br>1735<br>1630<br>1507<br>1286 | |

TABLE 7-continued

| Ex. No./structure/character/mp (° C.) | 1H NMR (δ) ppm | IR cm⁻¹ | MS |
|---|---|---|---|
| 2-5<br>Colorless crystal / 290<dec. | DMSO-d6, 300MHz<br>14.96(s, 1H)<br>13.05(s, 1H)<br>8.81(s, 1H)<br>7.55(s, 1H)<br>7.01(s, 1H)<br>4.01(t, 2H, J=6.6Hz)<br>3.90(s, 3H)<br>1.7–1.9(m, 2H)<br>1.3–1.5(m, 4H)<br>0.91(t, 3H, J=6.8Hz) | KBr<br>3422<br>1685<br>1211 | FAB+<br>305(M +<br>H +)(100) |

TABLE 8

| Ex. No./structure/character/mp (° C.) | 1H NMR (δ) ppm | IR cm⁻¹ | MS |
|---|---|---|---|
| 2-6<br>Pale blown crystal / 188–189 | DMSO-d6, 300MHz<br>14.58(s, 1H)<br>8.76(s, 1H)<br>7.52(d, 1H, J=8.8Hz)<br>7.07(d, 1H, J=8.8Hz)<br>4.02(s, 3H)<br>3.93(s, 3H)<br>3.91(r, 2H, J=6.9Hz)<br>1.7–1.9(m, 2H)<br>1.3–1.5(m, 4H)<br>0.95(t, 3H, J=7.1Hz) | KBr<br>2956<br>1735<br>1622<br>1560<br>1509<br>1458<br>1379<br>1280<br>1067 | FAB+<br>320(M + H +)<br>(100)<br>302(100) |
| 2-7<br>Colorless crystal / 196–197 | CDCl3, 300MHz<br>14.70(s, 1H)<br>8.78(s, 1H)<br>7.11(s, 1H)<br>6.83(s, 1H)<br>4.08(t, 2H, J=6.8Hz)<br>4.06(s, 3H)<br>3.86(s, 3H)<br>1.8–2.0(m, 2H)<br>1.3–1.5(m, 4H)<br>0.95(t, 3H, J=7.1Hz) | KBr<br>3448<br>1718<br>1654<br>1560<br>1508<br>1271 | FAB+<br>320(M + H +)<br>(50)<br>302(100) |
| 3-1<br>Colorless crystal / 98.0–99.0° C. | CDCl3, 300MHz<br>9.74(1H, bt)<br>9.13(1H, bs)<br>8.49(1H, s)<br>8.53(2H, d, J=6.0Hz)<br>7.46(1H, d, J=8.9Hz)<br>7.22(2H, d, J=6.0Hz)<br>6.94(1H, d, J=8.9Hz)<br>4.14(2H, t, J=6.9Hz)<br>3.98(3H, s)<br>3.76(2H, q, J=6.7Hz)<br>2.97(2H, t, J=7.2Hz)<br>1.74–1.88(2H, m)<br>1.35–1.53(4H, m)<br>0.95(3H, t, J=7.1Hz) | KBr<br>3257<br>2938<br>1672<br>1622<br>1530<br>1261<br>1112<br>805 | FAB+<br>410[M + H +]<br>(60)<br>288(60) |

TABLE 9

| Ex. No./structure/character/mp (° C.) | 1H NMR (δ) ppm | IR cm⁻¹ | MS |
|---|---|---|---|
| 3-2 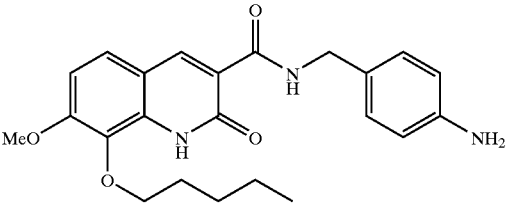 Colorless amorphous / | CDCl3, 300MHz<br>9.87(1H, br)<br>9.10(1H, bs)<br>8.89(1H, s)<br>7.45(1H, d, J=8.8Hz)<br>7.18(2H, d, J=8.3Hz)<br>6.93(1H, d, J=8.8Hz)<br>6.66(2H, d, J=8.3Hz)<br>4.56(2H, d, J=6.0Hz)<br>4.13(2H, t, J=6.9Hz)<br>3.97(3H, s)<br>1.71–1.87(2H, m)<br>1.30–1.50(4H, m)<br>0.94(3H, t, J=7.1Hz) | KBr<br>3232<br>2954<br>1668<br>1622<br>1520<br>1260<br>1109<br>801 | FAB+<br>410[M + H +]<br>(40)<br>288 (20) |
| 3-3 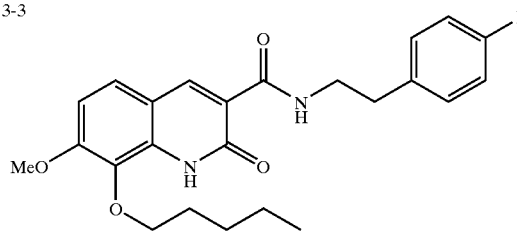 Colorless crystal / 125.0–126.0° C. | CDCl3, 300MHz<br>9.63(1H, br)<br>9.10(1H, bs)<br>8.85(1H, s)<br>7.44(1H, d, J=8.7Hz)<br>7.07(2H, d, J=8.4Hz)<br>6.93(1H, d, J=8.7Hz)<br>6.66(1H, d, J=8.4Hz)<br>4.13(2H, r, J=6.8Hz)<br>3.97(3H, s)<br>3.67(2H, q, J=6.8Hz)<br>2.83(2H, t, J=7.2Hz)<br>1.75–1.88(2H, m)<br>1.30–1.50(4H, m)<br>0.95(3H, t, J=7.2Hz) | KBr<br>3248<br>2928<br>1672<br>1625<br>1539<br>1260<br>1112<br>802 | FAB+<br>424[M + H +]<br>(40) |
| 3-4 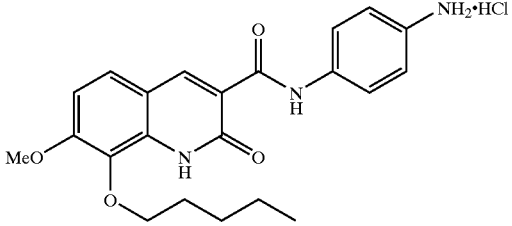 Colorless crystal / 267.0–268.0° C. | DMSO-d6, 300MHz<br>12.1(1H, s)<br>11.7(1H, s)<br>8.88(1H, s)<br>7.77(2H, d, J=9.0Hz)<br>7.75(1H, d, J=9.0Hz)<br>7.26(2H, d, J=9.0Hz)<br>7.18(1H, d, J=9.0Hz)<br>4.00(2H, t, J=6.9Hz)<br>1.70–1.83(2H, m)<br>1.30–1.50(4H, m)<br>0.89(3H, t, J=7.2Hz) | KBr<br>2954<br>1672<br>1622<br>1552<br>1498<br>1284<br>1263 | FAB+<br>296(30)<br>288(100)<br>218(70) |

TABLE 10

| Ex. No./structure/character/mp (° C.) | 1H NMR (δ) ppm | IR cm⁻¹ | MS |
|---|---|---|---|
| 3-5 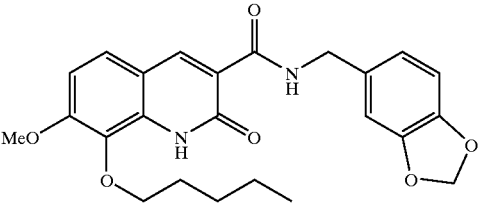 Colorless crystal / 126–127 | CDCl3, 300MHz<br>13.99 9.18(br, 1H)<br>9.18(s, 1H)<br>8.90(s, 1H)<br>7.47(d, 1H, J=8.8Hz)<br>6.95(d, 1H, J=8.8Hz)<br>6.8–6.9(m, 2H)<br>6.77(d, 1H, J=7.9Hz)<br>5.95(s, 2H)<br>4.59(d, 2H, J=5.8Hz)<br>4.14(t, 2H, J=8.7Hz)<br>3.99(s, 3H)<br>1.7–1.9(m, 2H)<br>1.3–1.5(m, 4H)<br>0.95(t, 3H, J=7.1Hz) | KBr<br>2956<br>1684<br>1619<br>1535<br>1263 | FAB+<br>439[M + H +]<br>(100) |

TABLE 10-continued

| Ex. No./structure/character/mp (° C.) | 1H NMR (δ) ppm | IR cm⁻¹ | MS |
|---|---|---|---|
| 3-6 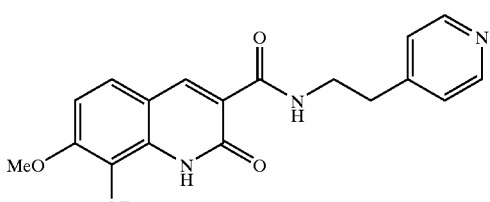 Colorless crystal / 201–211 | CDCl3, 300MHz<br>9.80(br t, J=5.9Hz, 1H)<br>9.21(br s, 1H)<br>8.81(s, 1H)<br>8.58(d, J=5.9Hz, 2H)<br>7.53(d, J=6.2Hz, 2H)<br>7.47(d, J=8.8Hz, 1H)<br>6.96(d, J=8.8Hz, 1H)<br>4.25(q, J=7.1Hz, 2H)<br>3.99(s, 3H)<br>3.83(q, J=6.6Hz, 2H)<br>3.12(t, J=7.0Hz, 2H)<br>1.43(t, J=7.1Hz, 3H) | KBr<br>1672<br>1626<br>1538<br>1500<br>1375<br>1286<br>1260<br>1223<br>1115 | (ESI+)<br>368<br>264<br>246<br>(ESI−)<br>366<br>323 |
| 3-7 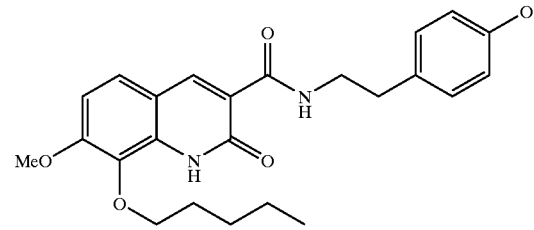 Colorless crystal / 106–107 | 9.71(br, 1H)<br>9.18(s, 1H)<br>8.86(s, 1H)<br>7.44(d, 1H, J=8.7Hz)<br>7.12(d, 2H, J=8.4Hz)<br>6.93(d, 1H, J=8.4Hz)<br>6.80(d, 2H, J=8.4Hz)<br>6.23(s, 1H)<br>4.12(t, 2H, J=6.6Hz)<br>3.97(s, 3H)<br>3.70(q, 2H, J=7.2Hz)<br>2.87(t, 2H, J=7.2Hz)<br>1.7–1.9(m, 2H)<br>1.3–1.5(m, 4H)<br>0.94(t, 3H, J=7.2Hz) | KBr<br>3246<br>2932<br>1673<br>1625<br>1537<br>1515<br>1500<br>1262<br>1110 | FAB+<br>425(M + H +)<br>(100)<br>288(75) |

TABLE 11

| Ex. No./structure/character/mp (° C.) | 1H NMR (δ) ppm | IR cm⁻¹ | MS |
|---|---|---|---|
| 3-8 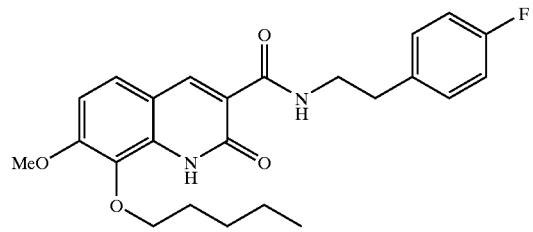 Colorless crystal/105–106 | 9.67(bt, 1H)<br>9.11(s, 1H)<br>8.85(s, 1H)<br>7.45(d, 1H, J=8.7Hz)<br>7.2–7.3(m, 2H)<br>7.00(t, 2H, J=8.7Hz)<br>6.93(d, 1H, J=8.7Hz)<br>4.13(t, 2H, J=6.9Hz)<br>3.97(s, 3H)<br>3.97(q, 2H, J=7.2Hz)<br>2.92(t, 2H, J=7.2Hz)<br>1.7–1.9(m, 2H)<br>1.3–1.6(m, 4H)<br>0.95(t, 3H, J=6.9Hz) | KBr<br>3286<br>2962<br>1661<br>1614<br>1533<br>1497<br>1262 | FAB+<br>427(M + H+)<br>(100)<br>288(40) |
| 3-9 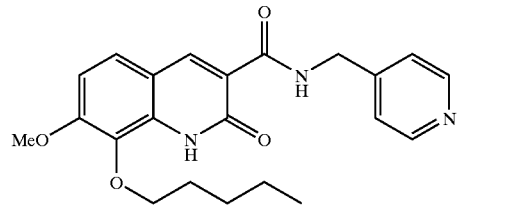 Colorless crystal/164–163 | CDCl3,300MHz<br>10.16(br, 1H)<br>9.26(s, 1H)<br>8.90(s, 1H)<br>8.55(d, 2H, J=6.8Hz)<br>7.47(d, 1H, J=8.8)<br>7.28(d, 2H, J=6.8)<br>6.87(d, 1H, J=8.8Hz)<br>4.70(t, 2H, J=6.0Hz)<br>4.15(t, 2H, J=6.9Hz)<br>3.99(s, 3H)<br>1.7–1.9(m, 2H)<br>1.3–1.5(m, 4H)<br>0.95(t, 3H, J=6.9Hz) | KBr<br>2956<br>1684<br>1619<br>1535<br>1263 | FAB+<br>396(M + H+)<br>(100)<br>288(40) |

TABLE 11-continued

| Ex. No./structure/character/mp (° C.) | 1H NMR (δ) ppm | IR cm⁻¹ | MS |
| --- | --- | --- | --- |
| 3-10<br>Yellow oil/ | CDCl3,300MHz<br>9.76(bt, 1H)<br>9.12(s, 1H)<br>8.85(s, 1H)<br>7.44(d, 1H, J=9.0Hz)<br>6.93(d, 1H, J=9.0Hz)<br>4.13(t, 2H, J=6.9Hz)<br>3.97(s, 3H)<br>3.60(q, 2H, J=6.6Hz)<br>2.59(t, 2H, J=6.6Hz)<br>2.4–2.5(m, 4H)<br>1.7–1.9(m, 2H)<br>1.5–1.7(m, 4H)<br>1.3–1.5(m, 6H)<br>0.95(t, 3H, J=6.9Hz) | Neat<br>2932<br>1667<br>1537<br>1504 | FAB+<br>416(M + H+)<br>(100)<br>331(50)<br>288(40) |

TABLE 12

| Ex. No./structure/character/mp (° C.) | 1H NMR (δ) ppm | IR cm⁻¹ | MS |
| --- | --- | --- | --- |
| 3-11<br>Colorless crystal/94–96 | CDCl3,300MHz<br>9.81(bt, 1H)<br>9.13(s, 1H)<br>8.86(s, 1H)<br>7.45(d, 1H, J=8.9Hz)<br>6.94(d, 1H, J=8.9Hz)<br>4.13(t, 2H, J=6.9Hz)<br>3.98(s, 3H)<br>3.7–3.8(m, 4H)<br>3.61(q, 2H, J=6.4Hz)<br>2.62(t, 2H, J=6.4Hz)<br>2.5–2.6(m, 4H)<br>1.7–1.9(m, 2H)<br>1.4–1.5(m, 4H)<br>0.95(t, 3H,J=71 Hz) | KBr<br>3438<br>2953<br>1718<br>1639<br>1507<br>1486<br>1287 | FAB+<br>418(M + H+)<br>(100) |
| 3-12<br>Colorless crystal/143–144 | CDCl3,300MHz<br>10.07(bt, 1H)<br>9.16(s, 1H)<br>8.89(s, 1H)<br>8.64(s, 1H)<br>8.52(d, 1H, J=1.7Hz)<br>7.7(d, 1H, J=7.9Hz)<br>7.47(t, 1H, J=8.8Hz)<br>7.26(dd, 1H, J=7.9, 1.7Hz)<br>6.95(d, 1H, J=8.8Hz)<br>4.70(d, 2H, J=6.0Hz)<br>4.14(t, 2H, J=6.9Hz)<br>3.98(s, 3H)<br>1.7–1.9(m, 2H)<br>1.3–1.5(m, 4H)<br>0.94(t, 3H, J=7.1Hz) | KBr<br>2956<br>1684<br>1618<br>1537<br>1264 | FAB+<br>396(M + H+)<br>(100)<br>288(40) |
| 3-13<br>Colorless crystal/142–144 | CDCl3,300MHz<br>10.35(bt, 1H)<br>9.17(s, 1H)<br>8.90(s, 1H)<br>8.60(d, 1H, J=4.7Hz)<br>7.65(dt, 1H, J=7.7, 1.7Hz)<br>7.46(d, 1H, J=8.9Hz)<br>7.61(t, 1H, J=7.7Hz)<br>7.16(dt, 1H, J=4.7, 1.7Hz)<br>6.94(d, 1H, J=8.9Hz)<br>4.84(t, 2H, J=5.6Hz)<br>4.14(t, 2H, J=6.9Hz)<br>3.98(s, 3H)<br>1.7–1.9(m, 2H)<br>1.3–1.5(m, 4H)<br>0.94(t, 3H, J=6.9Hz) | KBr<br>2931<br>1668<br>1622<br>1526<br>1262 | FAB+<br>396(M + H+)<br>(100)<br>288(40) |

TABLE 13

| Ex. No./structure/character/mp (° C.) | 1H NMR (δ) ppm | IR cm$^{-1}$ | MS |
|---|---|---|---|
| 3-14 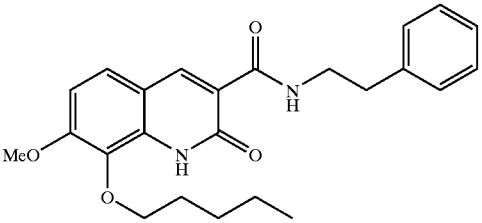 Colorless crystal/91–93 | CDCl3,300MHz<br>9.97(9.97(br t, J=5.9Hz, 1H)<br>9.12(br s, 1H)<br>8.86(s, 1H)<br>7.45(d, J=8.8Hz, 1H)<br>7.35–7.23(m, 5H)<br>6.93(d, J=8.8Hz, 1H)<br>4.14(t, J=70 Hz, 2H)<br>3.97(s, 3H)<br>3.74(q, J=6.8Hz, 2H)<br>2.95(t, J=7.1Hz, 2H)<br>1.81(quintet, J=7.1Hz, 2H)<br>1.51(m, 2H)<br>1.00(t, J=7.3Hz, 3H)br t, J=5.9Hz, 1H) | KBr<br>1660<br>1613<br>1535<br>1375<br>1260<br>1133 | (fab+, NBA)<br>395<br>274<br>218<br>(fab-, NBA)<br>393<br>305<br>153 |
| 3-15 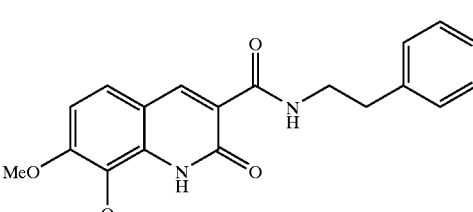 Colorless crystal/125–127 | CDCl3,300MHz<br>9.67(br t, J=5.9Hz, 1H)<br>9.12(br s, 1H)<br>8.85(s, 1H)<br>7.45(d, J=8.8Hz, 1H)<br>7.24(m, 2H)<br>7.00(m, 2H)<br>6.93(d, J=8.8Hz, 1H)<br>4.14(t, J=7.0Hz, 2H)<br>3.97(s, 3H)<br>3.71(q, J=6.8Hz, 2H)<br>2.92(t, J=7.1Hz, 2H)<br>1.80(quintet, J=7.1Hz, 2H)<br>1.51(m, 2H)<br>1.00(t, J=7.3Hz, 3H) | 2964<br>1661<br>1613<br>1532<br>1376<br>1259<br>1111 | (fab+,<br>(NBA)<br>413<br>274<br>218<br>(fab-, NBA)<br>411<br>305<br>153 |
| 3-16 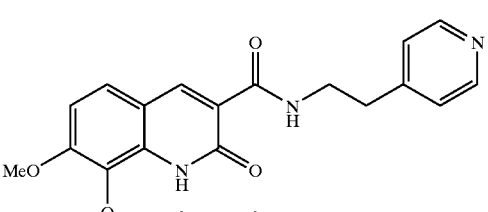 Colorless crystal/135–136 | CDCl3,300MHz<br>9.73(br t, J=5.9Hz, 1H)<br>9.14(br s, 1H)<br>8.85(s, 1H)<br>8.53(d, J=6.2Hz, 2H)<br>7.45(d, J=8.8Hz, 1H)<br>7.21(d, J=5.9Hz, 2H)<br>6.94(d, J=8.8Hz, 1H)<br>4.15(t, J=69 Hz, 2H)<br>3.98(s, 3H)<br>3.76(q, J=6.7Hz, 2H)<br>2.96(t, J=7.3Hz, 2H)<br>1.80(quintet,J=7.5Hz, 2H)<br>1.51(m, 2H)<br>1.00(t, J=7.3Hz, 3H) | KBr<br>1676<br>1626<br>1537<br>1499<br>1370<br>1284<br>1260<br>1113 | (fab+, NBA)<br>396<br>274<br>218<br>(fab-, NBA)<br>394<br>305<br>153 |

TABLE 14

| Ex. No./structure/character/mp (° C.) | 1H NMR (δ) ppm | IR cm$^{-1}$ | MS |
|---|---|---|---|
| 3-17 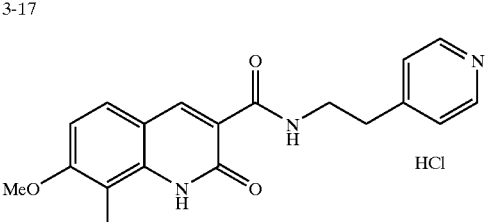 Colorless crystal/218 (decomp) | DMSO-d6,300MHz<br>(br s, 1H)<br>9.79(t, J=5.9Hz, 1H)<br>8.84(d, J=6.6Hz, 2H, J=6.6Hz)<br>8.72(s, 1H)<br>8.00(d, J=6.6Hz, 2H)<br>7.68(d, J=8.8Hz, 1H)<br>7.13(d, J=8.8Hz, 1H)<br>3.99(t, J=6.9Hz, 2H)<br>3.93(s, 3H)<br>3.75(q, J=6.5Hz, 2H)<br>3.19(t, J=6.6Hz, 2H)<br>1.76(quintet, J=7.3Hz, 2H)<br>1.41(m, 2H)<br>0.93(t, J=7.3Hz, 3H) | KBr<br>1676<br>1626<br>1537<br>1499<br>1370<br>1284<br>1260<br>1113 | (ESI+)<br>396<br>292<br>274<br>(ESI-)<br>394<br>338<br>322 |

TABLE 14-continued

| Ex. No./structure/character/mp (° C.) | 1H NMR (δ) ppm | IR cm⁻¹ | MS |
|---|---|---|---|
| 3-18 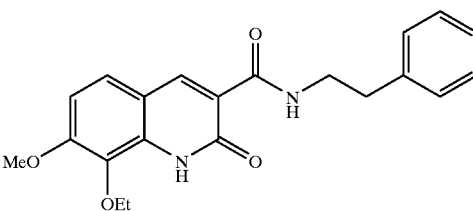<br>Colorless crystal/172–173 | CDCl3,300MHz<br>9.67(br t, J=5.9Hz, 1H)<br>9.17(br s, 1H)<br>8.86(s, 1H)<br>7.46(d, J=8.8Hz, 1H)<br>7.24(m, 2H)<br>7.00(m, 2H)<br>6.94(d, J=8.8Hz, 1H)<br>4.23(q, J=7.1H, 2Hz)<br>3.98(s, 3H)<br>3.70(q, J=7.1Hz, 2H)<br>2.9(t, J=7.1Hz, 2H)<br>1.42(t, J=7.0Hz, 3H) | KBr<br>1666<br>1626<br>1509<br>1262<br>1218<br>1114 | (ESI+)<br>385<br>264<br>246<br>(ESI−)<br>383<br>355<br>341 |
| 3-19 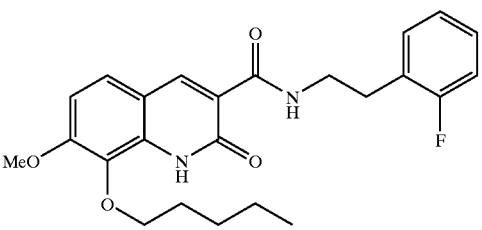<br>Colorless crystal/115–116 | CDCl3,300MHz<br>9.65(br, 1H)<br>9.12(s, 1H)<br>8.82(s, 1H)<br>7.40(d, 1H, J=8.8Hz)<br>6.9–7.3(m, 4H)<br>6.90(d, 1H, J=8.8Hz)<br>4.09(t, 2H, J=6.6Hz)<br>3.93(s, 3H)<br>3.67(q, 2H, J=7.0Hz)<br>2.96(t, 2H, J=7.0Hz)<br>1.7–1.9(m, 2H)<br>1.3–1.5(m, 4H)<br>0.91(t,3H, J=7.0Hz) | KBr<br>3235<br>2951<br>1663<br>1611<br>1530<br>1483<br>1286 | FAB+<br>427(M + H+)<br>(100) |

TABLE 15

| Ex. No./structure/character/mp (° C.) | 1H NMR (δ) ppm | IR cm⁻¹ | MS |
|---|---|---|---|
| 3-20 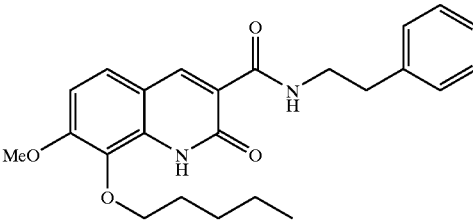<br>Colorless crystal/115–116 | 9.69(bt, 1H)<br>9.16(s, 1H)<br>8.86(s, 1H)<br>7.45(d, 1H, J=9.0Hz)<br>7.2–7.4(m, 1H)<br>6.93(d, 1H, J=9.0Hz)<br>6.8–7.1(m, 3H)<br>4.13(t, 2H, J=6.9Hz)<br>3.97(s, 3H)<br>3.72(q, 2H, J=7.2Hz)<br>2.95(t, 2H, J=7.2Hz)<br>1.7–1.9(m, 2H)<br>1.3–1.5(m,4H)<br>0.94(t, 3H, J=6.9Hz) | KBr<br>3134<br>2958<br>1670<br>1626<br>1535<br>1482<br>1286 | FAB+<br>427(M + H+)<br>(100) |
| 3-21 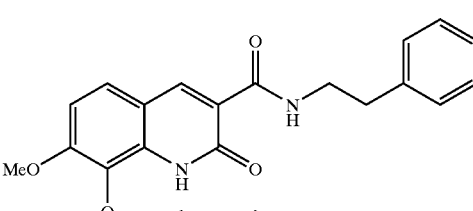<br>Colorless crystal/120–121 | CDCl3,300MHz<br>9.71(bt, 1H)<br>9.16(s, 1H)<br>8.67(s, 1H)<br>7.47(d, 1H, J=8.8Hz)<br>6.89(d, 1H, J=7.9Hz)<br>6.7–6.9(m, 3H)<br>5.61(s, 1H)<br>4.15(t, 2H, J=6.9Hz)<br>3.99(s, 3H)<br>3.90(s, 3H)<br>3.70(q, 2H, J=7.4Hz)<br>2.89(t, 2H,J=7.4Hz)<br>1.7–1.9(m, 2H)<br>1.3–1.5(m, 4H)<br>0.96(t, 3H, J=7.1Hz) | 3310<br>2952<br>1672<br>1625<br>1598<br>1529<br>1516<br>1260 | FAB+<br>455(M + H+)<br>(100) |

TABLE 15-continued

| Ex. No./structure/character/mp (° C.) | 1H NMR (δ) ppm | IR cm$^{-1}$ | MS |
|---|---|---|---|
| 3-22 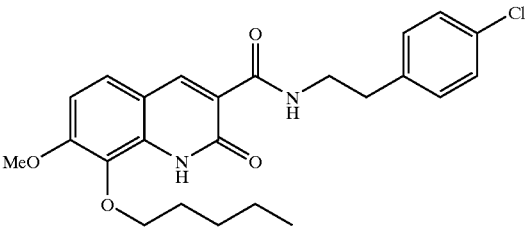 Colorless crystal/139–140 | CDCl3,300MHz<br>9.70(br, 1H)<br>9.16(s, 1H)<br>8.85(s, 1H)<br>7.45(d, 1H, J=8.9Hz)<br>7.27(d, 2H, J=8.4Hz)<br>7.20(d, 2H, J=8.4Hz)<br>6.93(d, 1H, J=8.9Hz)<br>4.13(t, 2H, J=6.9Hz)<br>3.87(s, 3H)<br>3.70(q, 2H, J=7.0Hz)<br>2.92(t, 2H, J=7.0Hz)<br>1.7–1.9(m, 2H)<br>1.3–1.5(m, 4H)<br>0.95(t, 3H, J=7.0Hz) | KBr<br>3286<br>2960<br>1661<br>1613<br>1530<br>1496<br>1261 | FAB+<br>443(M + H+)<br>(100) |

TABLE 16

| Ex. No./structure/character/mp (° C.) | 1H NMR (δ) ppm | IR cm$^{-1}$ | MS |
|---|---|---|---|
| 3-23 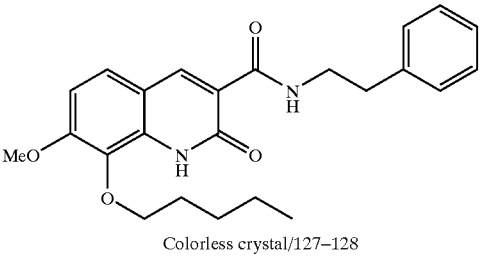 Colorless crystal/127–128 | CDCl3,300MHz<br>9.67(bt, 1H)<br>9.12(s, 1H)<br>8.86(s, 1H)<br>7.45(d, 1H, J=8.7Hz)<br>7.2–7.4(m, 5H)<br>6.93(d, 1H, J=8.7Hz)<br>4.13(t, 2H, J=6.9Hz)<br>3.97(s, 3H)<br>3.74(q, 2H, J=7.2Hz)<br>2.95(t, 2H, J=7.2Hz)<br>1.7–1.9(m,2H)<br>1.3–1.5(m, 4H)<br>0.95(t, 3H, J=7.2Hz) | KBr<br>3249<br>3139<br>2951<br>1661<br>1610<br>1284<br>1261<br>1116 | FAB+<br>409(M + H+)<br>(100) |
| 3-24 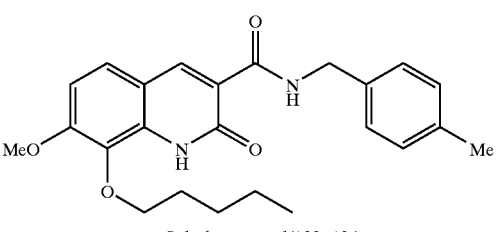 Colorless crystal/133–134 | CDCl3,300MHz<br>9.99(bt, 1H)<br>9.21(s, 1H)<br>8.91(s, 1H)<br>7.46(d, 1H, J=8.9Hz)<br>7.28(d, 2H, J=7.9Hz)<br>7.15(d, 2H, J=7.9Hz)<br>6.94(d, 1H, J=8.9Hz)<br>4.66(d, 2H, J=5.7Hz)<br>4.14(t, 2H, J=6.9Hz)<br>3.98(s, 3H)<br>2.34(s, 3H)<br>1.7–1.9(m, 2H)<br>1.3–1.5(m, 4H)<br>0.95(t, 3H, J=7.1Hz) | KBr<br>3263<br>3417<br>1663<br>1618<br>1596<br>1587<br>1265<br>1262<br>1110 | FAB+<br>408(M + H+)<br>(100) |
| 3-25 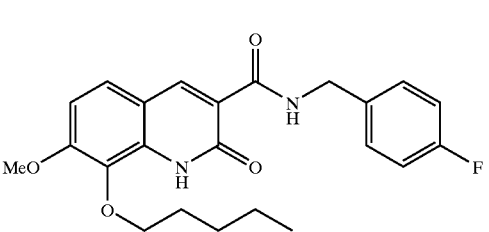 Colorless crystal/132–133 | CDCl3,300MHz<br>10.01(bt, 1H)<br>9.13(s, 1H)<br>8.99(s, 1H)<br>7.47(d, 1H, J=8.9Hz)<br>7.3–7.4(m, 2H)<br>7.01(t, 2H, J=8.7Hz)<br>6.94(d, 1H, J=8.9Hz)<br>4.64(d, 2H, J=5.8Hz)<br>4.14(t, 2H, J=6.9Hz)<br>3.98(s, 3H)<br>1.7–1.9(m, 2H)<br>1.3–1.5(m, 4H)<br>0.94(t, 3H, J=7.1Hz) | KBr<br>3242<br>1664<br>1619<br>1537<br>1510<br>1263 | FAB+<br>413(M + H+)<br>(100) |

TABLE 17

| Ex. No./structure/character/mp (° C.) | 1H NMR (δ) ppm | IR cm⁻¹ | MS |
|---|---|---|---|
| 3-26 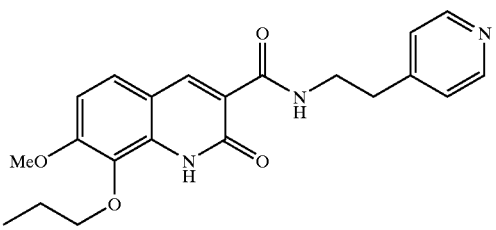 Colorless crystal/146–149 | DMSO-d6,300MHz<br>11.42(brs, 1H)<br>9.76(t, 1H, J=5.4Hz)<br>8.75(s, 1H)<br>8.47(d, 2H, J=6.0Hz)<br>7.68(d, 1H, 9.3Hz)<br>7.30(d, 2H, J=5.7Hz)<br>7.13(d, 1H, J=9.0Hz)<br>3.95(m, 5)<br>3.64(q, 2H, J=6.3Hz)<br>2.88(t,2H, 6.9Hz)<br>1.78(m, 2H)<br>0.94(t, 3H, J=7.2Hz) | KBr<br>1671<br>1627<br>1537<br>1374<br>1265 | (FAB+)<br>382(M + H+)<br>(80) |
| 3-27 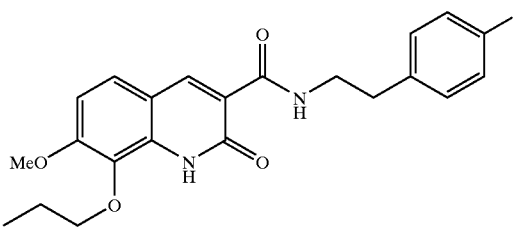 Colorless crystal/153–157 | DMSO-d6,300MHz<br>11.42(brs, 1H)<br>9.75(t, 1H, J=6.0Hz)<br>8.75(s, 1H)<br>7.68(d, 1H, J=8.7Hz)<br>7.31(m, 2H)<br>7.12(m, 3H)<br>3.95(m, 5H)<br>3.58(q, 2H, J=6.3Hz)<br>2.84(t, 2H, J=6.9Hz)<br>1.78(m, 2H)<br>0.94(t, 3H, J=7.2Hz) | KBr<br>2961<br>1666<br>1624<br>1536<br>1219 | (FAB+)<br>399(M + H+)<br>(90) |
| 3-28 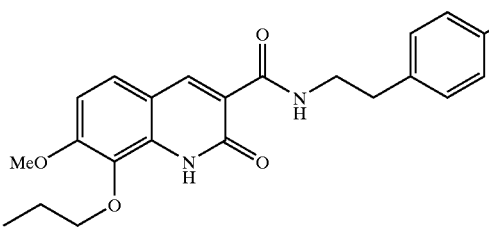 Colorless crystal/204–206 | DMSO-d6,300MHz<br>11.40(brs, 1H)<br>9.73(t, 1H, 5.4Hz)<br>9.16(s, 1H)<br>8.74(s, 1H)<br>7.68(d, 1H, J=9.3Hz)<br>7.12(d, 1H, J=9.3Hz)<br>7.06(d, 2H, J=8.4Hz)<br>6.68(d, 2H, J=8.4Hz)<br>3.95(m, 5H)<br>3.52(q, 2H, J=6.0Hz)<br>2.72(t, 2H, J=6.9Hz)<br>1.78(m, 2H)<br>0.94(t, 3H, J=7.2Hz) | KBr<br>3236<br>1668<br>1611<br>1538<br>1261 | (FAB+)<br>397(M + H+)<br>(70) |

TABLE 18

| Ex. No./structure/character/mp (° C.) | 1H NMR (δ) ppm | IR cm⁻¹ | MS |
|---|---|---|---|
| 3-29 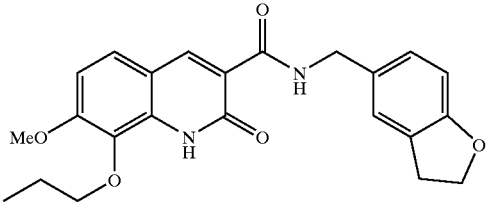 Colorless crystal/140–143 | DMSO-d6,300MHz<br>11.41(brs, 1H)<br>10.04(t, 1H, J=5.7Hz)<br>8.79(s, 1H)<br>7.70(d, 1H, J=8.7Hz)<br>7.14(d, 1H, J=8.7Hz)<br>6.86(m, 3H)<br>5.99(s, 2H)<br>4.47(d, 2H, J=5.7Hz)<br>3.96(m, 5H)<br>1.79(m, 2H)<br>0.94(t, 3H,J=7.5Hz) | KBr<br>2967<br>1664<br>1618<br>1535<br>1259 | (FAB+)<br>411(M + H+)<br>(80) |

TABLE 18-continued

| Ex. No./structure/character/mp (° C.) | 1H NMR (δ) ppm | IR cm$^{-1}$ | MS |
|---|---|---|---|
| 3-30 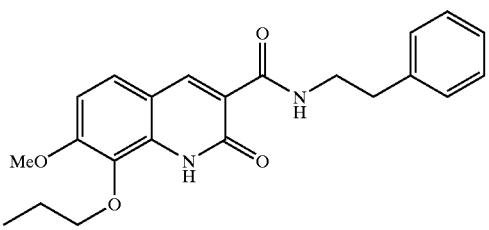 Colorless crystal/136–138 | DMSO-d6,300MHz<br>11.41(brs, 1H)<br>9.77(t, 1H, J=6.0Hz)<br>8.75(s, 1H)<br>7.68(d, 1H, J=8.7Hz)<br>7.26(m, 5H)<br>7.13(d, 1H, J=8.7Hz)<br>3.95(m, 5H)<br>3.59(q, 2H, J=5.7Hz)<br>2.85(t, 2H, J=7.2Hz)<br>1.78(m, 1H)<br>0.94(t,3H, J=7.5Hz) | KBr<br>1666<br>1625<br>1537<br>1261<br>1113 | (FAB+)<br>381(M + H+)<br>(100) |
| 3-31 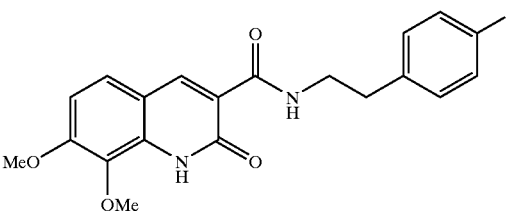 Colorless crystal/205–206 | CDCl3,300MHz<br>9.65(bt, 1H)<br>9.26(s, 1H)<br>8.86(s, 1H)<br>7.47(d, 1H, J=8.7Hz)<br>7.2–7.3(m, 2H)<br>7.00(t, 2H, J=8.4Hz)<br>6.94(d, 1H, J=8.7Hz)<br>4.00(S, 3H)<br>3.98(s, 3H)<br>3.70(q, 2H, J=7.2Hz)<br>2.92(t, 2H,J=7.2Hz) | KBr<br>3650<br>3250<br>1664<br>1509<br>1221 | FAB+<br>371(M + H+)<br>(100)<br>232(90) |

TABLE 19

| Ex. No./structure/character/mp (° C.) | 1H NMR (δ) ppm | IR cm$^{-1}$ | MS |
|---|---|---|---|
| 3-32 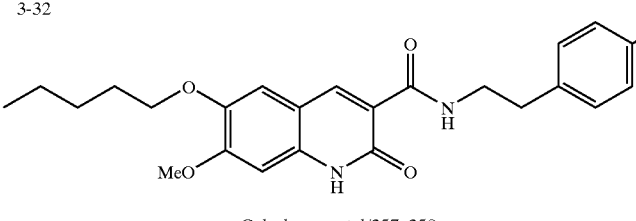 Colorless crystal/257–258 | DMSO-d6,300MHz<br>12.24(s, 1H)<br>9.89(bt, 1H)<br>7.45(s, 1H)<br>7.2–7.4(m, 2H)<br>7.11(t, 2H, J=8.9Hz)<br>6.90(s, 1H)<br>3.99(t, 2H, J=6.6Hz)<br>3.86(s, 3H)<br>3.55(q, 2H, J=7.3Hz)<br>2.83(t, 2H, J=7.3Hz)<br>1.7–1.9(m, 2H)<br>1.3–1.5(m, 4H)<br>0.90(t, 3H, J=7.0Hz) | KBr<br>3448<br>1670<br>1560<br>1508<br>1266 | FAB+<br>427(M + H+)<br>(100) |
| 3-33 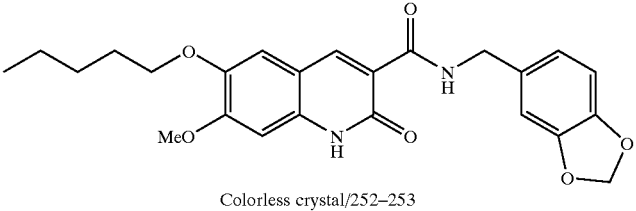 Colorless crystal/252–253 | CDCl3,300MHz<br>10.75(s, 1H)<br>10.00(bt, 1H)<br>8.88(s, 1H)<br>7.08(s, 1H)<br>6.7–6.9(m, 3H)<br>6.64(s, 1H)<br>5.93(s, 2H)<br>4.61(d, 2H, J=5.8Hz)<br>4.05(t, 2H, J=6.8Hz)<br>3.98(s, 3H)<br>1.8–2.0(m, 2H)<br>1.3–1.5(m, 4H)<br>0.95(t, 3H, J=7.1Hz) | 3448<br>1671<br>1509<br>1266 | FAB+<br>439(M + H+)<br>(100) |

TABLE 19-continued

| Ex. No./structure/character/mp (° C.) | 1H NMR (δ) ppm | IR cm⁻¹ | MS |
|---|---|---|---|
| 3-34<br>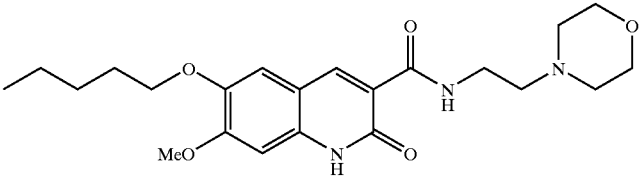<br>Colorless crystal/188–189 | DMSO-d6,300MHz<br>12.21(s, 1H)<br>9.98(br, 1H)<br>8.71(s, 1H)<br>7.45(s, 1H)<br>6.90(s, 1H)<br>3.98(t, 2H, J=6.9Hz)<br>3.86(s, 3H)<br>3.5–3.7(m, 4H)<br>3.4–3.5(m, 2H)<br>2.6–2.7(m, 2H)<br>2.5–2.6(m, 4H)<br>1.6–1.9(m, 2H)<br>1.2–1.5(m, 4H)<br>0.93(t, 3H, J=7.0Hz) | KBr<br>3448<br>1676<br>1244 | FAB+<br>418(M + H+)<br>(100) |

TABLE 20

| Ex. No./structure/character/mp (° C.) | 1H NMR (δ) ppm | IR cm⁻¹ | MS |
|---|---|---|---|
| 3-35<br>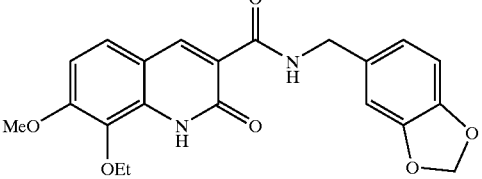<br>Colorless crystal/158–160 | DMSO-d6,300MHz<br>11.54(brs, 1H)<br>10.05(t, 1H, J=5.9Hz)<br>8.79(s, 1H)<br>7.70(d, 1H, J=8.8Hz)<br>7.14(d, 1H, J=8.8Hz)<br>6.87(m, 3H)<br>5.99(s, 2H)<br>4.47(d, 2H, J=5.9Hz)<br>4.07(q, 2H, J=7.0Hz)<br>3.93(s, 3H)<br>1.32(t,3H, J=7.0Hz) | KBr<br>3168<br>1673<br>1619<br>1536<br>1257<br>1106 | (FAB+)<br>397(M + H+)<br>(80) |
| 3-36<br>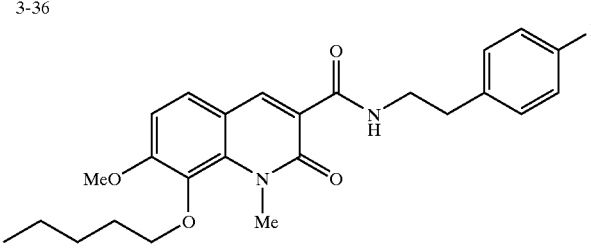<br>Colorless crystal/136–137 | CDCl3,300MHz<br>9.90(bt, 1H)<br>8.74(s, 1H)<br>7.46(d, 1H, J=8.7Hz)<br>7.2–7.3(m, 2H)<br>6.9–7.1(m, 2H)<br>6.97(d, 1H, J=8.7Hz)<br>4.11(s, 3H)<br>4.09(s, 3H)<br>3.86(t, 2H, J=6.8Hz)<br>3.69(q, 2H, J=7.3Hz)<br>2.92(t, 2H,J=7.3Hz)<br>1.7–1.9(m, 2H)<br>1.3–1.6(m, 4H)<br>0.94(t, 3H, J=7.1Hz) | 3231<br>2953<br>1673<br>1612<br>1535<br>1530<br>1270<br>1219 | FAB+<br>441(M + H+)<br>(100)<br>302(90) |
| 3-37<br>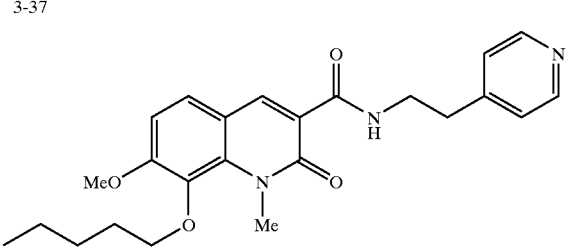<br>Colorless crystal/127–128 | CDCl3,300MHz<br>9.97(br, 1H)<br>8.74(s, 1H)<br>8.52(d, 2H, J=5.9Hz)<br>7.48(d, 1H, J=8.8Hz)<br>7.21(,d 2H, J=5.9Hz)<br>6.99(d, 1H, J=8.8Hz)<br>4.00(s, 3H)<br>3.98(s, 3H)<br>3.87(t, 2H, J=6.8Hz)<br>3.75(q, 2H, J=7.2Hz)<br>2.96(t, 2H, J=7.2Hz)<br>1.7–1.9(m, 2H)<br>1.3–1.5(m, 4H)<br>0.94(t, 3H, J=7.1Hz) | KBr<br>3448<br>2955<br>1672<br>1611<br>1579<br>1334<br>1452<br>1270 | FAB+<br>424(M + H+)<br>(100) |

TABLE 21

| Ex. No./structure/character/mp (° C.) | 1H NMR (δ) ppm | IR cm⁻¹ | MS |
|---|---|---|---|
| 3-38 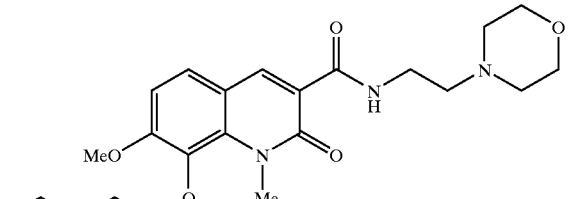 Colorless crystal/102–103 | CDCl3,300MHz<br>9.96(bt, 1H)<br>8.74(s, 1H)<br>7.46(d, 1H, J=8.7Hz)<br>6.97(d, 1H, J=8.7Hz)<br>4.02(s, 3H)<br>3.98(s, 3H)<br>3.85(t, 2H, J=6.6Hz)<br>3.7–3.8(m, 4H)<br>3.61(q, 2H, J=6.6Hz)<br>2.62(t, 2H, J=6.6Hz)<br>2.5–2.6(m, 4H)<br>1.8–1.9(m, 2H)<br>1.3–1.5(m, 4H)<br>0.94(t, 3H, J=7.2Hz) | KBr<br>3448<br>2948<br>1672<br>1612<br>1581<br>1560<br>1535<br>1452<br>1269 | FAB+<br>432(M + H+)<br>(100) |
| 3-39 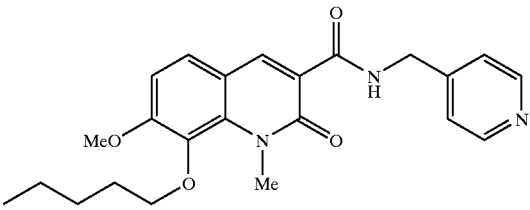 Colorless crystal/146–147 | CDCl3,300MHz<br>10.38(br 1H)<br>8.78(s, 1H)<br>8.55(d, 2H, J=6.8Hz)<br>7.49(d, 1H, J=8.7Hz)<br>7.28(d, 2H, J=6.8)<br>7.00(d, 1H, J=8.7Hz)<br>4.69(t, 2H, J=6.0Hz)<br>4.08(s, 3H)<br>3.99(s, 3H)<br>3.89(t, 2H, J=6.8Hz)<br>1.7–1.9(m, 2H)<br>1.3–1.5(m, 4H)<br>0.95(t, 3H, J=7.1Hz) | KBr<br>3264<br>2957<br>1668<br>1609<br>1579<br>1526<br>1286 | FAB+<br>410(M + H+)<br>(100) |
| 3-40 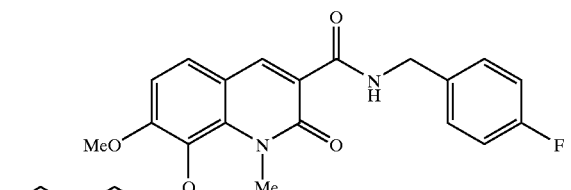 Colorless crystal/132–133 | CDCl3,300MHz<br>10.22(bt, 1H)<br>8.78(s, 1H)<br>7.48(d, 1H, J=8.7Hz)<br>7.3–7.4(m, 2H)<br>7.02(d, 1H, J=8.7Hz)<br>6.9–7.0(m, 3H)<br>4.64(d, 2H, J=5.8Hz)<br>4.00(s, 3H)<br>3.98(s, 3H)<br>3.87(t, 2H, J=6.9Hz)<br>1.7–1.9(m, 2H)<br>1.3–1.5(m, 4H)<br>0.94(t, 3H, J=6.9Hz) | KBr<br>3448<br>1688<br>1610<br>1579<br>1560<br>1528<br>1288 | FAB+<br>427(M + H+)<br>(100) |

TABLE 22

| Ex. No./structure/character/mp (° C.) | 1H NMR (δ) ppm | IR cm⁻¹ | MS |
|---|---|---|---|
| 3-41 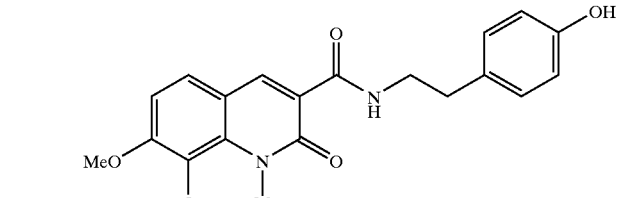 Colorless crystal/180–181 | CDCl3,300MHz<br>10.01(bt, 1H)<br>8.75(s, 1H)<br>7.46(d, 1H, J=8.8Hz)<br>7.08(d, 2H, J=8.4Hz)<br>6.73(d, 1H, J=8.8Hz)<br>6.79(d, 2H, J=8.4Hz)<br>6.90(bs, 1H)<br>4.00(s, 3H)<br>3.98(s, 3H)<br>3.86(t, 2H, J=6.8Hz)<br>3.68(q, 2H, J=7.2Hz)<br>2.86(t, 2H, J=7.2Hz)<br>1.7–1.9(m,2H)<br>1.3–1.5(m, 4H)<br>0.94(t, 3H, J=7.1Hz) | KBr<br>3246<br>2939<br>1672<br>1606<br>1536<br>1514<br>1500<br>1270 | FAB+<br>439(M + H+)<br>(100) |

TABLE 22-continued

| Ex. No./structure/character/mp (° C.) | 1H NMR (δ) ppm | IR cm$^{-1}$ | MS |
|---|---|---|---|
| 3-42 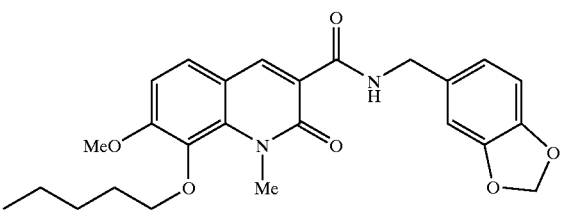 Colorless crystal/107–108 | CDCl3,300MHz<br>10.15(bt, 1H)<br>8.77(s, 1H)<br>7.47(d, 1H, J=8.8Hz)<br>6.98(d, 1H, J=8.8Hz)<br>6.87(d, 1H, J=1.5Hz)<br>6.84(dd, 1H, J=7.7, 1.5Hz)<br>6.75(d, 1H, J=7.7Hz)<br>5.92(s, 2H)<br>4.57(d, 2H, J=5.5Hz)<br>4.00(s, 3H)<br>3.98(s, 3H)<br>3.87(t, 2H, J=7.0Hz)<br>1.7–1.9(m, 2H)<br>1.3–1.5(m, 4H)<br>0.94(t, 3H, J=7.0Hz) | KBr<br>2930<br>1268<br>800 | FAB+<br>453(M + H+)<br>(100)<br>302(100) |
| 3-43 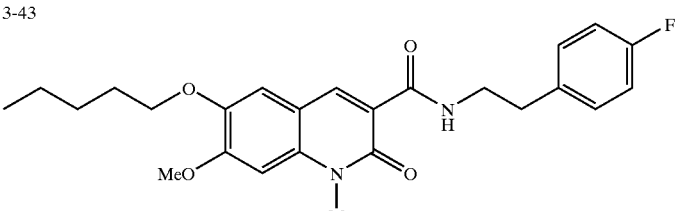 Colorless crystal/147–148 | CDCl3,300MHz<br>10.00(bt, 1H)<br>8.77(s, 1H)<br>7.2–7.3(m, 2H)<br>7.10(s, 1H)<br>6.99(t, 2H, J=8.6Hz)<br>6.77(s, 1H)<br>4.07(t, 2H, J=7.0Hz)<br>4.02(s, 3H)<br>3.77(s, 3H)<br>3.70(q, 2H, J=7.7Hz)<br>2.92(t, 2H, J=7.7Hz)<br>1.7–2.0(m, 2H)<br>1.3–1.6(m, 4H)<br>0.95(t,3H, J=6.9Hz) | KBr<br>2935<br>1672<br>1510<br>1426<br>1260 | FAB+<br>442(M + H+)<br>(100)<br>302(100) |

TABLE 23

| Ex. No./structure/character/mp (° C.) | 1H NMR (δ) ppm | IR cm$^{-1}$ | MS |
|---|---|---|---|
| 3-44 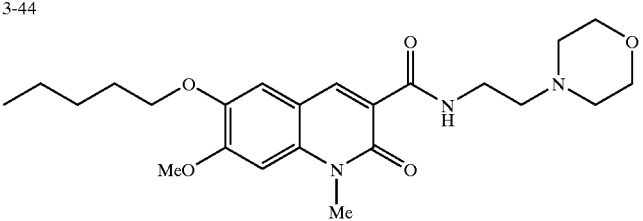 Colorless crystal/174–175 | CDCl3.300MHz<br>10.06(bt, 1H)<br>8.77(s, 1H)<br>7.10(s, 1H)<br>6.77(s, 1H)<br>4.07(t, 2H, J=7.0Hz)<br>4.03(s, 3H)<br>3.78(s, 3H)<br>3.6–3.7(m, 4H)<br>3.62(q, 2H, J=6.6Hz)<br>2.63(t, 2H, J=6.6Hz)<br>2.5–2.6(m, 4H)<br>1.8–2.0(m, 2H)<br>1.3–1.6(m, 4H)<br>0.95(t, 3H,J=7.0Hz) | KBr<br>2934<br>1672<br>1609<br>1543<br>1430<br>1397<br>1260<br>1171<br>1120 | FAB+<br>432(M + H+)<br>(100)<br>302(100) |
| 3-45 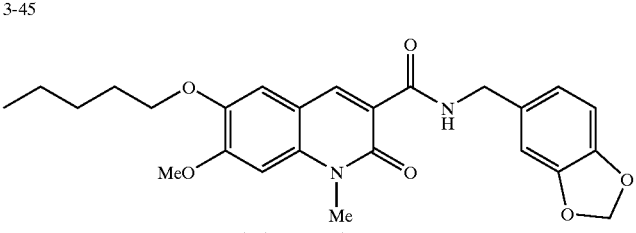 Colorless crystal/176–177 | CDCl3,300MHz<br>10.24(t, 1H, J=5.9Hz)<br>8.81(s, 1H)<br>7.11(s, 1H)<br>6.88(s, 1H)<br>6.84(d, 1H, J=8.1Hz)<br>6.78(s, 1H)<br>6.75(d, 1H, J=8.1Hz)<br>5.92(s, 1H)<br>4.58(d, 2H, J=5.9Hz)<br>4.07(t, 2H, J=7.0Hz)<br>4.02(s, 3H)<br>3.76(s, 3H)<br>1.8–2.0(m, 2H)<br>1.3–1.6(m, 4H)<br>0.95(t, 3H, J=7.0Hz) | KBr<br>3448<br>1671<br>1542<br>1251 | FAB+<br>453(M + H+)<br>(100)<br>302(100) |

TABLE 23-continued

| Ex. No./structure/character/mp (° C.) | 1H NMR (δ) ppm | IR cm⁻¹ | MS |
|---|---|---|---|
| 3-46<br>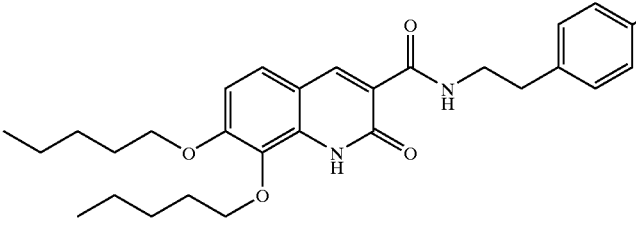<br>Colorless crystal/106–107 | CDCl3,300MHz<br>9.67(bt, 1H)<br>9.15(s, 1H)<br>8.85(s, 1H)<br>7.42(d, 1H, J=8.7Hz)<br>7.2–7.3(m, 2H)<br>7.00(t, 2H, J=8.4Hz)<br>6.91(d, 1H, J=8.7Hz)<br>4.15(t, 2H, J=7.2Hz)<br>4.12(t, 2H, J=6.6Hz)<br>3.70(q, 2H, J=7.2Hz)<br>2.92(t, 2H, J=7.2Hz)<br>1.7–1.9(m,4H)<br>1.3–1.6(m, 8H)<br>0.95(t, 3H, J=7.2Hz)<br>0.95(t, 3H, J=7.2Hz) | KBr<br>3286<br>1654<br>1520<br>1500 | FAB+<br>483(M + H+)<br>(100)<br>344(50) |

TABLE 24

| Ex. comp./structure/character/mp (° C.) | 1H NMR (δ) ppm | IR cm⁻¹ | MS |
|---|---|---|---|
| 3-47<br><br>Colorless crystal/241~242 | DMSO-d6,300MHz<br>11.22(bs, 1H)<br>10.10(t, 1H, J=5.8Hz)<br>9.66(s, 1H)<br>8.76(s, 1H)<br>7.45(d, 1H, J=8.8Hz)<br>7.14(d, 1H, J=8.8Hz)<br>6.91(s, 1H)<br>6.87(d, 1H, J=7.9Hz)<br>6.82(d, 1H, J=7.9Hz)<br>5.99(s, 2H)<br>4.45(d, 2H, J=5.8Hz)<br>3.91(s, 3H) | KBr<br>3161<br>1655<br>1268<br>1113<br>1039<br>934<br>802<br>521 | LCQ(+)<br>369<br>[M + H+]<br>(100) |
| 3-48<br>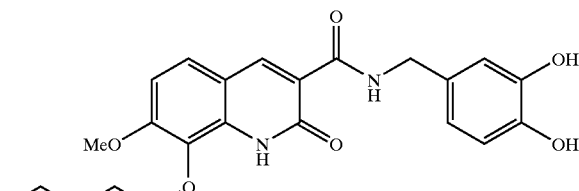<br>Colorless crystal/124~125 | DMSO-d6,300MHz<br>11.42(s, 1H)<br>9.96(t, 1H, J=5.7Hz)<br>8.86(s, 1H)<br>8.79(s, 1H)<br>8.75(s, 1H)<br>7.67(d, 1H, J=9.0Hz)<br>7.14(d, 1H, J=9.0Hz)<br>6.73(d, 1H, J=3.6Hz)<br>6.68(d, 1H, J=8.1Hz)<br>6.59(dd, 1H, J=8.1, 3.6 Hz)<br>4.38(d, 2H, J=5.7Hz)<br>3.99(t, 2H,J=6.9Hz)<br>3.93(s, 3H)<br>1.7–1.8(m, 2H)<br>1.3–1.4(m, 4H)<br>0.89(t, 3H, J=7.2Hz) | KBr<br>3246<br>1672<br>1626<br>1536<br>1260<br>1109 | FAB+<br>427<br>[M + H+]<br>(100) |
| 3-49<br>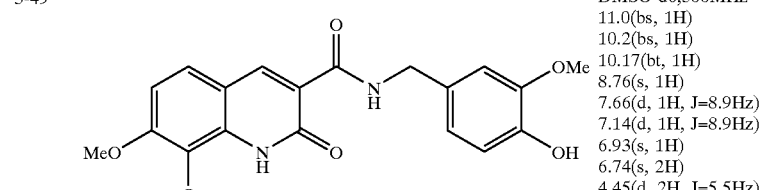<br>Colorless crystal/145~146 | DMSO-d6,300MHz<br>11.0(bs, 1H)<br>10.2(bs, 1H)<br>10.17(bt, 1H)<br>8.76(s, 1H)<br>7.66(d, 1H, J=8.9Hz)<br>7.14(d, 1H, J=8.9Hz)<br>6.93(s, 1H)<br>6.74(s, 2H)<br>4.45(d, 2H, J=5.5Hz)<br>3.98(t, 2H, J=6.8Hz)<br>3.91(s, 3H)<br>3.75(s, 3H)<br>1.7–1.9(m, 2H)<br>1.3–1.5(m, 4H)<br>0.88(t, 3H, J=7.0Hz) | KBr<br>3350<br>3193<br>2954<br>1920<br>1668<br>1627<br>1528<br>1464 | LCQ(−)<br>439<br>[M − H+]<br>(100) |

TABLE 25

| Ex. comp./structure/character/mp (° C.) | 1H NMR (δ) ppm | IR cm$^{-1}$ | MS |
|---|---|---|---|
| 3-50 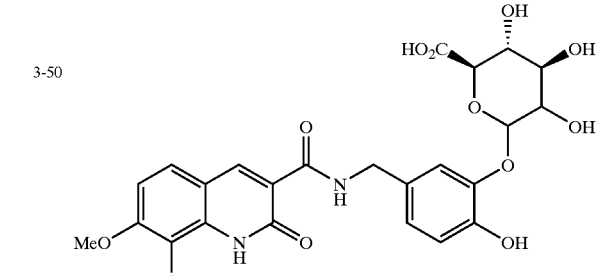 Colorless crystal/ | DMSO-d6,300MHz<br>11.45, 11.39(s, 1H)<br>9.9–10.1(t, 1H)<br>8.79, 8.79(s, 1H)<br>6.6–6.8(bs, 1H)<br>7.64(d, 1H, J=8.9Hz)<br>7.13(d, 1H, J=8.9Hz)<br>6.7–7.1(m, 3H)<br>5.63, 5.57(bs, 1H)<br>5.22(bs, 1H), 4.8–4.9(m, 1H, 4.44(bd, 2H)<br>3.98(t, 2H, J=6.9Hz)<br>3.93(s,3H)<br>3.82(d, 1H, J=9.6Hz)<br>3.3–3.5(m, 4H)<br>1.7–1.9(m, 2H)<br>1.3–1.5(m, 4H)<br>0.89(t, 3H, 7.2Hz) | KBr<br>3396<br>1666 | FAB+<br>603<br>[M + H+]<br>(100) |
| 3-51 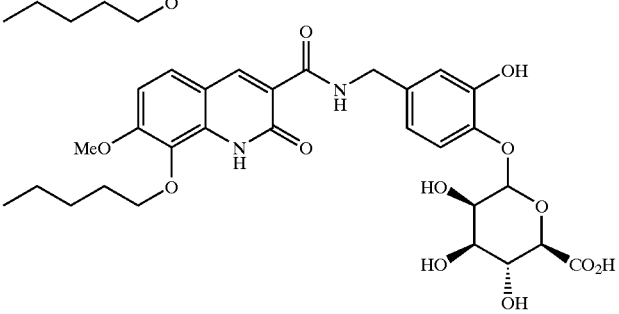 Colorless crystal/209~210 | DMSO-d6,300MHz<br>11.8(bs, 1H)<br>11.5(bs, 1H)<br>10.04(bt, 1H)<br>8.79(s, 1H)<br>7.70(d, 1H, J=8.9Hz)<br>7.14(d, 1H, J=8.9Hz)<br>6.91(s, 1H)<br>6.86(d, 1H, J=7.9Hz)<br>6.82(d, 1H, J=7.9Hz)<br>5.98(s, 2H)<br>4.46(d, 2H, J=5.9Hz)<br>3.99(t, 2H, J=6.5Hz)<br>3.93(s,3H)<br>2.27(t, 2H, J=7.2Hz)<br>1.7–1.9(m, 2H)<br>1.6–1.7(m, 2H) | KBr<br>3300<br>1730 | LCQ(+)<br>469<br>[M + H+]<br>(100) |
| 3-52 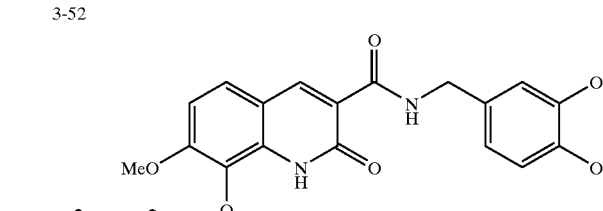 Colorless crystal/189~190 | DMSO-d6,300MHz<br>12.00(bs, 1H)<br>11.50(bs, 1H)<br>10.00(t, 1H, J=5.7Hz)<br>8.88(bs, 1H)<br>8.80(s, 1H)<br>7.70(d, 1H, J=8.9Hz)<br>7.14(d, 1H, J=8.9Hz)<br>6.93(s, 1H)<br>6.74(s, 2H)<br>4.45(d, 2H, J=5.7Hz)<br>3.98(t, 2H, J=6.6Hz)<br>3.96(s, 3H)<br>3.75(s,3H)<br>2.2–2.4(m, 2H)<br>1.7–1.8(m, 2H)<br>1.6–1.7(m, 2H) | KBr<br>3449<br>1707<br>1686<br>1626<br>1545<br>1499<br>1263 | LCQ(+)<br>471<br>[M + H+]<br>(100) |

TABLE 26

| Ex. comp./structure/character/mp (° C.) | 1H NMR (δ) ppm | IR cm⁻¹ | MS |
|---|---|---|---|
| 3-53 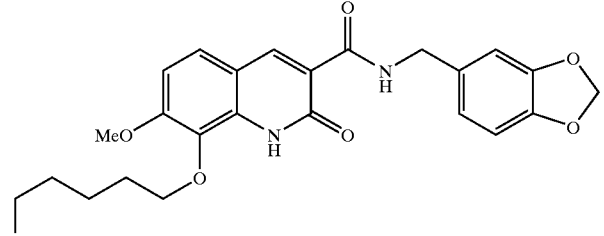 Colorless crystal/96~97 | DMSO-d6,300MHz<br>11.45(s, 1H)<br>10.04(t, 1H, J=5.9Hz)<br>8.79(s, 1H)<br>7.70(d, 1H, J=8.9Hz)<br>7.14(d, 1H, J=8.9Hz)<br>6.91(s, 1H)<br>6.87(d, 1H, J=7.9Hz)<br>6.82(d, 1H, J=7.9Hz)<br>5.99(s, 2H)<br>4.47(d, 2H, J=5.9Hz)<br>4.36(t, 2H, J=5.1Hz)<br>3.98(t, 2H,J=6.9Hz)<br>3.93(s, 3H)<br>3.3–3.4(m, 2H)<br>1.7–1.8(m, 2H)<br>1.4–1.5(m, 4H) | KBr<br>3300<br>2900<br>1550 | LCQ(+)<br>455<br>[M + H+]<br>(100) |
| 3-54 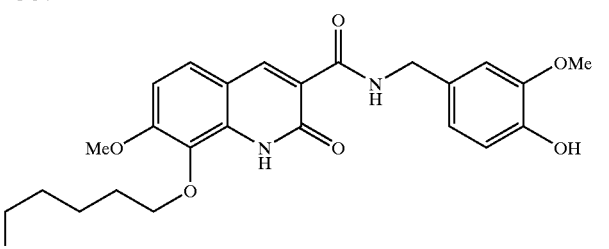 Colorless amorphous solid/ | DMSO-d6,300MHz<br>11.46(s, 1H)<br>10.00(t, 1H, J=5.7Hz)<br>8.88(s, 1H)<br>8.80(s, 1H)<br>7.70(d, 1H, J=8.9Hz)<br>7.14(d, 1H, J=8.9Hz)<br>6.93(s, 1H)<br>6.73(s, 1H)<br>4.45(d, 1H, J=5.7Hz)<br>4.36(t, 1H, J=5.3Hz)<br>3.98(t, 2H, J=6.8Hz)<br>3.93(s,3H)<br>3.74(s, 3H)<br>3.3–3.5(m, 2H)<br>1.7–1.9(m, 2H)<br>1.4–1.6(m, 4H) | KBr<br>3392<br>1554<br>1260<br>1110<br>1038<br>801 | LCQ(+)<br>457<br>[M + H+]<br>(100) |
| 3-55 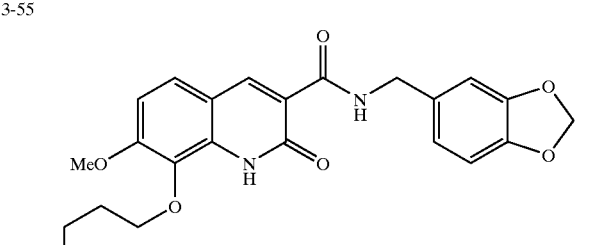 Colorless crystal/128~129 | DMSO-d6,300MHz<br>11.47(s, 1H), 10.04(t,<br>1H, J=6.0Hz)<br>8.79(s, 1H)<br>7.70(d, 1H, J=8.9Hz)<br>7.14(d, 1H, J=8.9Hz)<br>6.91(d, 1H, J=1.4Hz)<br>6.87(d, 1H, J=7.9Hz)<br>6.82(dd, 1H, J=7.9,<br>1.4Hz), 5.99(s, 2H)<br>4.47(d, 2H, J=6.0Hz)<br>4.43(d, 1H,J=4.7Hz)<br>3.99(t, 2H, J=6.9Hz)<br>3.93(s, 3H)<br>3.6–3.7(m, 1H)<br>1.7–1.9(m, 2H)<br>1.4–1.5(m, 2H)<br>1.07(d, 3H, J=6.2Hz) | KBr<br>3397<br>2965<br>1672<br>1623<br>1544<br>1501<br>1260 | LCQ(+)<br>455<br>[M + H+]<br>(100) |

TABLE 27

| Ex. comp./structure/character/mp (° C.) | 1H NMR (δ) ppm | IR cm⁻¹ | MS |
|---|---|---|---|
| 3-56 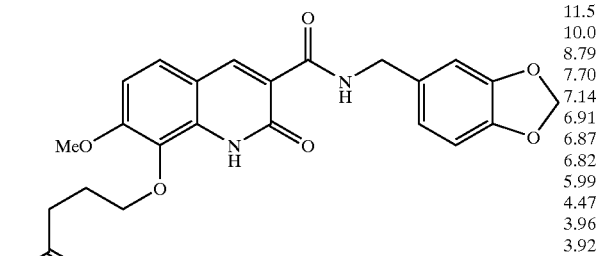 Colorless crystal/153~154 | DMSO-d6,300MHz<br>11.53(s, 1H)<br>10.04(t, 1H, J=5.9Hz)<br>8.79(s, 1H)<br>7.70(d, 1H, J=8.9Hz)<br>7.14(d, 1H, J=8.9Hz)<br>6.91(s, 1H)<br>6.87(d, 1H, J=7.9Hz)<br>6.82(d, 1H, J=7.9Hz)<br>5.99(s, 2H)<br>4.47(d, 2H, J=5.9Hz)<br>3.96(t, 2H, J=6.5Hz)<br>3.92(s, 3H)<br>2.64(t, 2H, J=7.2Hz)<br>2.13(s, 3H)<br>1.9–2.0(m, 2H) | KBr<br>3290<br>2895<br>1707<br>1672<br>1621<br>1538<br>1440<br>1371 | LCQ(+)<br>453<br>[M + H+]<br>(100) |

TABLE 27-continued

| Ex. comp./structure/character/mp (° C.) | 1H NMR (δ) ppm | IR cm$^{-1}$ | MS |
|---|---|---|---|
| 3-57<br>Colorless crystal/118~119 | DMSO-d6,400MHz<br>11.55(s, 1H)<br>10.02(bt, 1H)<br>8.78(s, 1H)<br>7.69(d, 1H, J=8.9Hz)<br>7.15(d, 1H, J=8.9Hz)<br>6.90(s, 1H)<br>6.87(d, 1H, J=8.0Hz)<br>6.82(d, 1H, J=8.0Hz)<br>5.98(s, 2H)<br>4.82(bs, 1H)<br>4.46(d, 2H, J=5.8Hz)<br>4.0–4.2(2H), 3.93(s, 3H), 3.58(bs, 1H)<br>1.8–2.0(m,1H)<br>1.6–1.8(m, 1H)<br>1.4–1.5(m, 2H)<br>0.88(t, 3H, J=7.4Hz) | KBr<br>3438<br>1626<br>1110<br>1802 | LCQ(+)<br>455<br>[M + H+]<br>(100) |
| 3-58<br>Colorless crystal/148~149 | DMSO-d6,300MHz<br>11.31(s, 1H)<br>10.01(bt, 1H)<br>8.81(s, 1H)<br>7.74(d, 1H, J=8.7Hz)<br>7.15(d, 1H, J=8.9Hz)<br>6.92(d, 1H, J=0.9Hz)<br>6.85(d, 1H, J=7.8Hz)<br>6.82(dd, 1H, J=7.8, 0.9Hz)<br>5.99(s, 2H)<br>4.46(d, 2H, J=5.7Hz)<br>4.15(d, 2H, J=6.0Hz)<br>3.93(s, 3H)<br>3.01(t, 2H, J=5.4Hz)<br>2.55(q, 2H, 6.9Hz)<br>0.97(t, 3H, J=6.9Hz) | KBr<br>3448<br>1676<br>1534<br>1259<br>1120<br>805 | LCQ(+)<br>453<br>[M + H+]<br>(100) |

TABLE 28

| Ex. comp./structure/character/mp (° C.) | 1H NMR (δ) ppm | IR cm$^{-1}$ | MS |
|---|---|---|---|
| 3-59<br>Colorless crystal/185~186 | DMSO-d6,300MHz<br>11.47(s, 1H)<br>10.00(t, 1H, J=6.0Hz)<br>8.81(s, 1H)<br>7.73(d, 1H, J=8.7Hz)<br>7.15(d, 1H, J=8.7Hz)<br>6.90(s, 1H)<br>6.87(d, 1H, J=7.8Hz)<br>6.81(d, 1H, J=7.8Hz)<br>5.99(s, 2H)<br>5.65(bd, 1H)<br>4.46(d, 2H, J=6.0Hz)<br>4.07(dd, 1H, J=9.9, 2.1Hz), 3.94(s, 3H)<br>3.80(bs, 1H)<br>3.6–3.7(m, 1H)<br>1.3–1.5(m, 4H)<br>0.89(t, 3H, J=6.6Hz) | KBr<br>3404<br>1666<br>1545<br>1264 | LCQ(+)<br>455<br>[M + H+]<br>(100) |
| 3-60<br>Colorless crystal/198~199 | CDCl3,300MHz<br>9.36(bs, 1H)<br>9.23(s, 1H)<br>8.88(s, 1H)<br>7.45(d, 1H, 9.0Hz)<br>6.94(d, 1H, 9.0Hz)<br>5.86(bs, 1H)<br>4.14(t, 2H, J=7.2Hz)<br>3.98(s, 3H)<br>1.7–1.9(m, 2H)<br>1.3–1.5(m, 4H)<br>0.95(t, 3H, J=6.9Hz) | KBr<br>3329<br>3163<br>2956<br>1687<br>1500<br>1370<br>1300 | FAB+<br>305<br>[M + H+]<br>(100) |

TABLE 29

| Ex. No./structure/character/mp (° C.) | 1H NMR (δ) ppm | IR cm$^{-1}$ | MS |
|---|---|---|---|
| 4-1 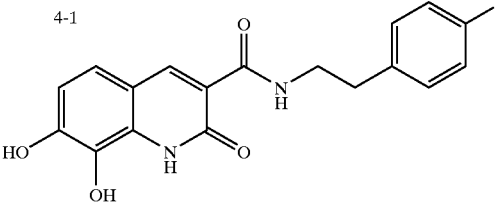<br>Pale yellow crystal/272–273 | DMSO-d6,300MHz<br>11.06(s, 1H)<br>10.30(s, 1H)<br>9.80(bt, 1H)<br>9.25(s, 1H)<br>8.65(s, 1H)<br>7.29(d, 1H, J=8.6Hz)<br>7.2–7.4(m, 2H)<br>7.1–7.2(m, 2H)<br>6.83(d, 1H, J=8.6Hz)<br>3.55(q, 2H, J=7.2Hz)<br>2.83(t, 2H, J=7.2Hz) | KBr<br>3236<br>1668<br>1510<br>1357<br>1220 | FAB+<br>343[M − H+]<br>(100) |
| 5-1 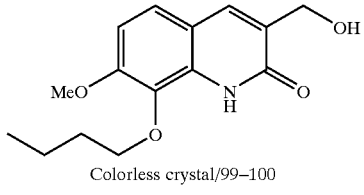<br>Colorless crystal/99–100 | CDCl3,300MHz<br>9.10(br s, 1H)<br>7.65(s, 1H)<br>7.26(d, J=8.0Hz, 1H)<br>6.86(d, J=8.0Hz, 1H)<br>4.65(s, 2H)<br>4.13(t, J=6.6Hz, 2H)<br>3.95(s, 3H)<br>1.80(m, 2H)<br>1.50(m, 2H)<br>0.99(t, J=7.3Hz, 3H) | KBr<br>3176<br>1651<br>1610<br>1509<br>1281<br>1111<br>1063 | (fab+, NBA)<br>278<br>260<br>(fab−, NBA)<br>276<br>199 |
| 5-2 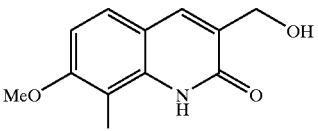<br>Colorless crystal/154–157 | CDCl3,300MHz<br>9.18(brs, 1H)<br>7.65(s, 1H)<br>7.26(d, 1HJ=8.4Hz)<br>6.87(d, 1H, J=8.7Hz)<br>4.65(s, 2H)<br>4.22(q, 2H, 6.9Hz)<br>3.95(s, 3H)<br>3.36(brs, 1H)<br>1.42(t, 3H, J=6.9Hz) | KBr<br>3434<br>1644<br>1510<br>1379<br>1283 | |

TABLE 30

| Ex. No./structure/character/mp (° C.) | 1H NMR (δ) ppm | IR cm$^{-1}$ | MS |
|---|---|---|---|
| 6-1 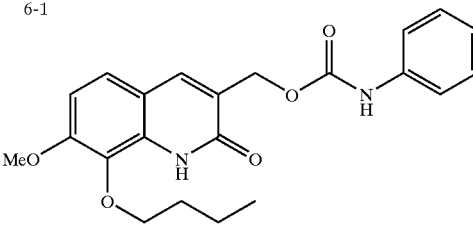<br>Colorless crystal/164–165 | CDCl3,300MHz<br>9.05(br s, 1H)<br>7.83(s, 1H)<br>7.33(dd, J=4.6, 8.9Hz, 2H)<br>7.26(d, J=8.8Hz, 1H)<br>6.99(t, J=8.8Hz, 2H)<br>6.86(br s, 1H)<br>6.85(d, J=8.8Hz, 1H)<br>5.21(s, 2H)<br>4.11(t, J=6.8Hz, 2H)<br>3.94(s, 3H)<br>1.79(m, 2H)<br>1.50(m, 2H)<br>0.99(t, J=7.7Hz, 3H) | KBr<br>3305<br>1706<br>1656<br>1611<br>1537<br>1509<br>1262<br>1219<br>1112<br>1077 | (fab+, NBA)<br>415<br>260<br>(fab−, NBA)<br>413<br>276<br>199 |
| 6-2 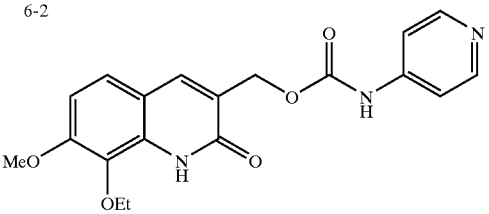<br>Colorless crystal/205(dec.) | DMSO-d6,300MHz<br>11.08(brs, 1H)<br>10.27(s, 1H)<br>8.39(d, 2H, J=6.2Hz)<br>7.94(s, 1H)<br>7.44(m, 3H)<br>7.02(d, 1H, J=8.8Hz)<br>5.06(s, 2H)<br>4.05(q, 2H, J=7.0Hz)<br>3.89(s, 3H)<br>1.31(t, 3H, J=7.0Hz) | KBr<br>2978<br>1745<br>1659<br>1609<br>1508<br>1251<br>1209 | (FAB+)<br>370(M + H+)<br>(50) |

TABLE 30-continued

| Ex. No./structure/character/mp (° C.) | 1H NMR (δ) ppm | IR cm$^{-1}$ | MS |
|---|---|---|---|
| 7-1 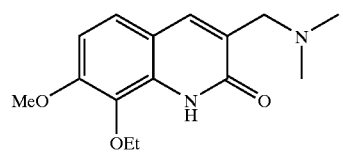<br>Colorless crystal/134–136 | CDCl3, 300MHz<br>9.03(brs, 1H)<br>7.75(s, 1H)<br>7.26(d, 1H, J=8.8Hz)<br>6.84(d, 1H, J=8.8Hz)<br>4.20(q, 2H, J=7.0Hz)<br>3.94(s, 3H)<br>3.47(s, 2H)<br>2.35(s, 6H)<br>1.41(t, 3H, J=7.0Hz) | KBr<br>2773<br>1644<br>1605<br>1285<br>1109 | FAB+<br>277(M + H+)<br>(100) |

TABLE 31

| Ex. No./structure/character/mp (° C.) | 1H NMR (δ) ppm | IR cm$^{-1}$ | MS |
|---|---|---|---|
| 7-2 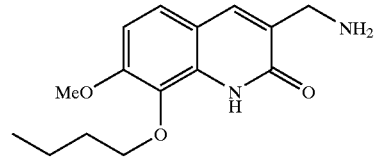<br>Colorless crystal/ | CDCl3, 300MHz<br>9.00(brs, 1H)<br>7.65(s, 1H)<br>7.24(d, J=8.7H)<br>6.83(d, J=8.7Hz, 1H)<br>4.12(t, J=6.9Hz, 2H)<br>3.93(s, 3H)<br>3.82(s, 2H)<br>1.80(m, 2H)<br>1.80(brs, 2H)<br>1.50(m, 2H)<br>0.99(t, J=7.3Hz, 3H) | | (fab+, NBA)<br>278<br>260<br>(fab−, NBA)<br>276<br>199 |
| 7-3 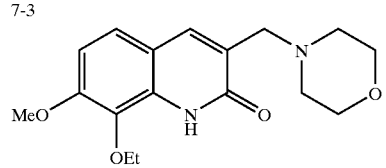<br>Colorless crystal/166–169 | CDCl3, 300MHz<br>9.03(brs, 1H)<br>7.78(brs, 1H)<br>7.27(d, 1H, J=8.8Hz)<br>6.85(d, 1H, J=8.8Hz)<br>4.20(q, 2H, J=7.0Hz)<br>3.94(s, 3H)<br>3.78(t, 4H, 4.8Hz)<br>3.56(brs, 2H)<br>1.41(t, 3H, J=7.0Hz) | KBr<br>2968<br>1656<br>1611<br>1280<br>1115 | FAB+<br>319(M + H+)<br>(100) |
| 8-1 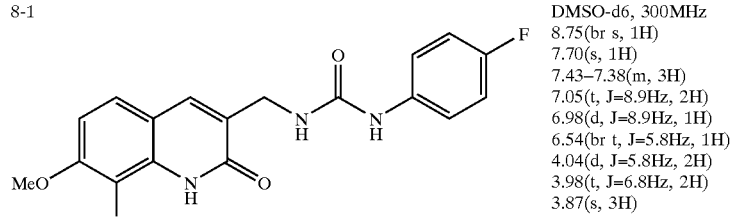<br>Colorless crystal/207–209 | DMSO-d6, 300MHz<br>8.75(br s, 1H)<br>7.70(s, 1H)<br>7.43–7.38(m, 3H)<br>7.05(t, J=8.9Hz, 2H)<br>6.98(d, J=8.9Hz, 1H)<br>6.54(br t, J=5.8Hz, 1H)<br>4.04(d, J=5.8Hz, 2H)<br>3.98(t, J=6.8Hz, 2H)<br>3.87(s, 3H)<br>1.75(m, 2H)<br>1.41(m, 2H)<br>0.93(t, J=7.3Hz, 3H) | KBr<br>3313<br>1659<br>1611<br>1577<br>1508<br>1281<br>1216<br>1113 | |

TABLE 32

| Ex. No./structure/character/mp (° C.) | 1H NMR (δ) ppm | IR cm⁻¹ | MS |
|---|---|---|---|
| 8-2<br>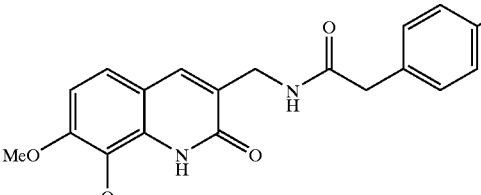<br>Colorless crystal/199–200 | DMSO-d6, 300MHz<br>10.72(br s, 1H)<br>9.24(br s, 1H)<br>8.27(t, J=5.9Hz, 1H)<br>7.41(s, 1H)<br>7.22(d, J=8.8Hz, 1H)<br>7.11(d, J=8.4Hz, 2H)<br>6.97(d, J=8.8Hz, 1H)<br>6.71(d, J=8.4Hz, 2H)<br>4.07(d, J=5.5Hz, 2H)<br>3.97(t, J=6.6Hz, 2H)<br>3.87(s, 3H)<br>3.38(s, 2H)<br>1.74(m, 2H)<br>1.41(m, 2H)<br>0.92(t, J=7.3Hz, 3H) | KBr<br>3387<br>1648<br>1609<br>1509<br>1278<br>1260<br>1108 | |

Pharmacological Experiment

[1] Binding assay (in vitro)

Membrane fractions of human central type cannabinoid receptor (human CB1-CHO, hereinafter called hCB1) and human peripheral type cannabinoid receptor (human CB2-CHO, hereinafter called hCB2) expressed in CHO cells were used as samples. The reference material (hCB1: 20 µg/ml, hCB2: 5 µg/ml), labeled ligand ([$^3$H]Win55212-2, 2 nM) and unlabeled ligand Win55212-2 or test compound were added to a 24-well round bottom plate, and the plate was incubated at 30° C. for 90 minutes. 50 mM Tris-HB55 containing 0.2% BSA was used as an assay buffer. After incubation, the mixture was filtered (Packard, Unifilter 24GF/B) and dried, and then a scintillation solution (Packard, Microsint-20) was added thereto to determine the radioactivity of the sample (Packard, Top count A9912V). Nonspecific binding was determined by the addition of excessive amount of Win55212-2 (10 µM), and specific binding was calculated by subtracting the nonspecific binding from total binding determined by the addition of the labeled ligand only. The test compound was dissolved in DMSO to make the final concentration in DMSO to be 0.1%. IC$_{50}$ value was determined from the proportion of the bound test compound in the specific binding, and K$_1$ value of the test compound was calculated from the IC$_{50}$ value and K$_d$ value of [$^3$H]Win55212-2. K$_1$ value for the central type receptors/K$_1$ value for peripheral type receptors (C/S) was also calculated as an indicator of the selectivity of the test compound for peripheral type receptors. Results are shown in Tables 33 to 36.

TABLE 33

| | Ki value (nM) | | |
|---|---|---|---|
| Example | Central type receptor (C) | Peripheral type receptor (S) | C/S |
| 1-2 | 3671 | 0.014 | 262202 |
| 1-4 | 1627 | 4.49 | 362 |
| 2-1 | 4330 | 8.90 | 487 |
| 2-2 | 3247 | 00.77 | 42172 |
| 2-4 | 905 | 0.032 | 28273 |
| 2-5 | 434 | 0.20 | 2170 |
| 2-6 | 770 | 0.13 | 5923 |
| 2-7 | 381 | 0.42 | 908 |
| 3-1 | 49 | 0.13 ± 0.05 | 372 |
| 3-5 | 3436 | 0.087 | 39497 |
| 3-6 | 609 | 0.020 | 30472 |
| 3-7 | 72 | 0.48 | 150 |
| 3-8 | 81 | 0.019 | 4275 |

TABLE 34

| | Ki value (nM) | | |
|---|---|---|---|
| Example | Central type receptor (C) | Peripheral type receptor (S) | C/S |
| 3-14 | 131 | 0.33 | 396 |
| 3-15 | 249 | 0.016 | 15580 |
| 3-16 | 208 | 0.010 | 20805 |
| 3-17 | 199 | 0.23 | 867 |
| 3-18 | 1751 | 7.10 | 247 |
| 3-19 | 49 | 0.18 | 272 |
| 3-20 | 78 | 0.41 | 191 |
| 3-21 | 162 | 0.97 | 167 |
| 3-22 | 135 | 0.20 | 675 |
| 3-23 | 39 | 0.20 | 194 |
| 3-25 | 444 | 1.29 | 344 |
| 3-26 | 648 | 0.23 | 2817 |
| 3-27 | 336 | 0.021 | 15990 |

TABLE 35

| | Ki value (nM) | | |
|---|---|---|---|
| Example | Central type receptor (C) | Peripheral type receptor (S) | C/S |
| 3-30 | 168 | 0.090 | 1862 |
| 3-31 | 159 | 0.16 | 995 |
| 3-32 | 2398 | 0.036 | 66604 |
| 3-33 | 273 | 1.06 | 258 |
| 3-34 | 172 | 0.011 | 15672 |
| 3-35 | 409 | 0.053 | 7713 |
| 3-36 | 183 | 0.021 | 8695 |
| 3-37 | 78 | 0.75 | 104 |

TABLE 35-continued

| | Ki value (nM) | | |
| --- | --- | --- | --- |
| Example | Central type receptor (C) | Peripheral type receptor (S) | C/S |
| 3-38 | 935 | 0.085 | 11002 |
| 3-40 | 703 | 2.13 | 330 |
| 3-41 | 62 | 0.35 | 176 |
| 3-42 | 315 | 0.22 | 1430 |
| 3-43 | 864 | 0.043 | 20093 |

TABLE 36

| | Ki value (nM) | | |
| --- | --- | --- | --- |
| Example | Central type receptor (C) | Peripheral type receptor (S) | C/S |
| 3-44 | 193 | 0.18 | 1075 |
| 3-45 | 381 | 0.032 | 11902 |
| 3-46 | 228 | 0.026 | 8776 |
| 5-1 | 686 | 0.45 | 1525 |
| 5-2 | 122 | 0.055 | 2219 |
| 6-1 | 703 | 0.045 | 15612 |
| 6-2 | 437 | 0.034 | 12866 |
| 7-1 | 3643 | 0.17 | 21432 |
| 7-3 | 666 | 0.062 | 10735 |
| 8-1 | 440 | 0.44 | 1000 |
| 8-2 | 727 | 0.27 | 2692 |

[2] Carrageenin-induced paw edema model (in vivo)

C57BL/6J mice (6 to 8 weeks of age) were used. The volume of the right hind paw before administration was measured (Unicom, Prethysumometter TK-101), and 2 hours later, the test compound dissolved in olive oil was administered orally at 10 ml/kg. After one hour of the administration, 50 µl of 1% solution of carrageenin in normal saline was administered intradermally at foot pad of the right hind paw. Three hours later, the volume of the right hind paw was measured and compared with the initial volume. Results are shown in Table 37.

TABLE 37

| Example | $ED_{50}$ (mg/kg; p.o.) | Example | $ED_{60}$ (mg/kg; p.o.) |
| --- | --- | --- | --- |
| 3-5 | <0.10 | 3-26 | 1.32 |
| 3-9 | 0.58 | 3-27 | 0.53 |
| 3-11 | 0.40 | 3-30 | 0.49 |
| 3-15 | 0.41 | 3-37 | 0.63 |
| 3-17 | 1.39 | 3-38 | 2.24 |
| 3-22 | 0.76 | 3-40 | 1.19 |

[3] The compounds of the invention were shown to significantly inhibit inflammation and hemorrhage in the pancreas, in the experiments using pancreatitis model induced by taurocholic acid in rats.

An example of formulation is shown below, but is not intended to limit the present invention.

Example of Formulation (a) The compound of Example 1-1: 10 g
(b) Lactose: 50 g
(c) Maize starch: 15 g
(d) Carboxymethylcellulose sodium: 44 g
(e) Magnesium stearate: 1 g All of (a), (b) and (c), and 30 g of (d) were kneaded with water, and the mixture was dried in vacuo and then granulated. To this granular powder, 14 g of (d) and 1 g of (e) were mixed, and the mixture was tabletted by a tablet maker to manufacture 1000 tablets containing 10 mg of (a) in a tablet.

Industrial Applicability

The compound [I] of the present invention and its pharmaceutically acceptable salts selectively act on cannabinoid receptors, particularly on peripheral type cannabinoid receptors, and have fewer side effects on the central nervous system, having great immunomodulating action, anti-inflammatory action and antiallergic action. Therefore, these compounds are useful as cannabinoid receptor (particularly peripheral cannabinoid receptors) regulator, immunomodulators, therapeutic agent for autoimmune diseases, anti-inflammatory agents, and antiallergic agents.

What is claimed is:

1. A cannabinoid receptor modulator comprising, as an active ingredient, 7-methoxy-2-oxo-8-pentyloxy-1,2-dihydroquinoline-3-carboxylic acid (3,4-methylenedioxybenzyl)amide, or a pharmaceutically acceptable salt thereof.

2. 7-Methoxy-2-oxo-8-pentyloxy-1,2-dihydroquinoline-3-carboxylic acid (3,4-methylenedioxybenzyl)amide, or a pharmaceutically acceptable salt thereof.

3. A pharmaceutical composition comprising, as an active ingredient, a compound of claim 2, or a pharmaceutically acceptable salt thereof.

4. A method of modulating a cannabinoid receptor in a subject, comprising the step of:

administering to a subject an effective amount of the pharmaceutical composition of claim 3, wherein said composition modulates a cannabinoid receptor within the subject.

5. A method of modulating a peripheral cannabinoid receptor in a subject, comprising the step of:

administering to a subject an effective amount of a pharmaceutical composition of claim 3, wherein said composition modulates a peripheral cannabinoid receptor within the subject.

6. A method of treating an autoimmune disease, allergy or inflammation in a subject, comprising the step of:

administering to a subject a therapeutically effective amount of a pharmaceutical composition of claim 3, wherein the composition treats the autoimmune disease, allergy or inflammation in the subject.

7. A method of treating inflammation in a subject, comprising the step of:

administering to a subject a therapeutically effective amount of a pharmaceutical composition of claim 3, wherein the composition treats inflammation in the subject.

* * * * *